(12) United States Patent
Berenzweig et al.

(10) Patent No.: US 10,842,407 B2
(45) Date of Patent: Nov. 24, 2020

(54) CAMERA-GUIDED INTERPRETATION OF NEUROMUSCULAR SIGNALS

(71) Applicant: Facebook Technologies, LLC, Menlo Park, CA (US)

(72) Inventors: Adam Berenzweig, Brooklyn, NY (US); Thomas Reardon, New York, NY (US); Christopher Osborn, Brooklyn, NY (US); Patrick Kaifosh, New York, NY (US); Brett Jurman, New York, NY (US); Daniel Wetmore, Brooklyn, NY (US)

(73) Assignee: Facebook Technologies, LLC, Menlo Park, CA (US)

( * ) Notice: Subject to any disclaimer, the term of this patent is extended or adjusted under 35 U.S.C. 154(b) by 0 days.

(21) Appl. No.: 16/557,427

(22) Filed: Aug. 30, 2019

(65) Prior Publication Data

US 2020/0069211 A1 Mar. 5, 2020

Related U.S. Application Data

(60) Provisional application No. 62/726,159, filed on Aug. 31, 2018.

(51) Int. Cl.
*A61B 5/0488* (2006.01)
*G06F 3/01* (2006.01)
(Continued)

(52) U.S. Cl.
CPC ........ *A61B 5/0488* (2013.01); *A61B 5/04001* (2013.01); *A61B 5/04004* (2013.01);
(Continued)

(58) Field of Classification Search
CPC .............. A61B 5/0488; A61B 5/04004; A61B 5/04012; A61B 5/6824; A61B 90/361;
(Continued)

(56) References Cited

U.S. PATENT DOCUMENTS 1,411,995 A 4/1922 Dull
3,580,243 A 5/1971 Johnson et al.
(Continued)

FOREIGN PATENT DOCUMENTS

CA 2902045 A1 8/2014
CA 2921954 A1 2/2015
(Continued)

OTHER PUBLICATIONS

PCT/US2017/043686, Oct. 6, 2017, International Search Report and Written Opinion.
(Continued)

*Primary Examiner* — Amandeep Saini
(74) *Attorney, Agent, or Firm* — FisherBroyles, LLP

(57) ABSTRACT

Computerized systems, methods, and computer-readable storage media storing code for implementing the methods are provided for training an inference model used to generate a musculoskeletal representation. One such system includes a processor programmed to: determine, based on information obtained from at least one image, position information describing a spatial relationship between two or more connected musculoskeletal segments of a user; determine, based on a plurality of neuromuscular signals, force information; associate the position information with the force information; train an inference model to output a musculoskeletal representation consistent with the position information and/or the force information when neuromuscular input signals provided to the inference model have at least one predetermined characteristic, to produce an updated inference model; and cause the updated inference model to be stored in a memory.

30 Claims, 12 Drawing Sheets

(51) Int. Cl.

| | |
|---|---|
| *A61B 5/00* | (2006.01) |
| *A61B 90/00* | (2016.01) |
| *A61B 5/04* | (2006.01) |
| *G06T 7/70* | (2017.01) |
| *G06N 20/00* | (2019.01) |
| *G06K 9/00* | (2006.01) |
| *G06K 9/62* | (2006.01) |
| *G06N 5/04* | (2006.01) |
| *G06T 19/00* | (2011.01) |
| *A61B 5/11* | (2006.01) |

(52) U.S. Cl.
CPC ........ *A61B 5/04012* (2013.01); *A61B 5/6824* (2013.01); *A61B 90/361* (2016.02); *G06F 3/011* (2013.01); *G06F 3/015* (2013.01); *G06K 9/00355* (2013.01); *G06K 9/6215* (2013.01); *G06N 5/04* (2013.01); *G06N 20/00* (2019.01); *G06T 7/70* (2017.01); *A61B 5/1107* (2013.01); *A61B 5/681* (2013.01); *A61B 5/7267* (2013.01); *A61B 2562/0219* (2013.01); *G06F 3/016* (2013.01); *G06F 3/017* (2013.01); *G06T 19/006* (2013.01); *G06T 2207/20081* (2013.01); *G06T 2207/30196* (2013.01)

(58) Field of Classification Search
CPC ... A61B 5/04001; A61B 5/681; A61B 5/7267; A61B 5/1107; A61B 2562/0219; G06F 3/011; G06F 3/017; G06T 19/006
USPC .......................................................... 382/128
See application file for complete search history.

(56) References Cited

U.S. PATENT DOCUMENTS

| | | |
|---|---|---|
| 3,620,208 A | 11/1971 | Higley |
| 3,880,146 A | 4/1975 | Everett et al. |
| 4,055,168 A | 10/1977 | Miller et al. |
| 4,602,639 A | 7/1986 | Hoogendoorn et al. |
| 4,705,408 A | 11/1987 | Jordi |
| 4,817,064 A | 3/1989 | Milles |
| 4,896,120 A | 1/1990 | Kamil |
| 5,003,978 A | 4/1991 | Dunseath, Jr. |
| D322,227 S | 12/1991 | Warhol |
| 5,081,852 A | 1/1992 | Cox |
| 5,251,189 A | 10/1993 | Thorp |
| D348,660 S | 7/1994 | Parsons |
| 5,445,869 A | 8/1995 | Ishikawa et al. |
| 5,482,051 A | 1/1996 | Reddy et al. |
| 5,605,059 A | 2/1997 | Woodward |
| 5,625,577 A | 4/1997 | Kunii et al. |
| 5,683,404 A | 11/1997 | Johnson |
| 6,005,548 A | 12/1999 | Latypov et al. |
| 6,009,210 A | 12/1999 | Kand |
| 6,032,530 A | 3/2000 | Hock |
| 6,184,847 B1 | 2/2001 | Fateh et al. |
| 6,238,338 B1 | 5/2001 | DeLuca et al. |
| 6,244,873 B1 | 6/2001 | Hill et al. |
| 6,377,277 B1 | 4/2002 | Yamamoto |
| D459,352 S | 6/2002 | Giovanniello |
| 6,411,843 B1 | 6/2002 | Zarychta |
| 6,487,906 B1 | 12/2002 | Hock |
| 6,510,333 B1 | 1/2003 | Licata et al. |
| 6,527,711 B1 | 3/2003 | Stivoric et al. |
| 6,619,836 B1 | 9/2003 | Silvant et al. |
| 6,658,287 B1 | 12/2003 | Litt et al. |
| 6,720,984 B1 | 4/2004 | Jorgensen et al. |
| 6,743,982 B2 | 6/2004 | Biegelsen et al. |
| 6,774,885 B1 | 8/2004 | Even-Zohar |
| 6,807,438 B1 | 10/2004 | Brun Del Re et al. |
| D502,661 S | 3/2005 | Rapport |
| D502,662 S | 3/2005 | Rapport |
| 6,865,409 B2 | 3/2005 | Getsla et al. |
| D503,646 S | 4/2005 | Rapport |
| 6,880,364 B1 | 4/2005 | Vidolin et al. |
| 6,927,343 B2 | 8/2005 | Watanabe et al. |
| 6,942,621 B2 | 9/2005 | Avinash et al. |
| 6,965,842 B2 | 11/2005 | Rekimoto |
| 6,972,734 B1 | 12/2005 | Ohshima et al. |
| 6,984,208 B2 | 1/2006 | Zheng |
| 7,022,919 B2 | 4/2006 | Brist et al. |
| 7,086,218 B1 | 8/2006 | Pasach |
| 7,089,148 B1 | 8/2006 | Bachmann et al. |
| D535,401 S | 1/2007 | Travis et al. |
| 7,173,437 B2 | 2/2007 | Hervieux et al. |
| 7,209,114 B2 | 4/2007 | Radley-Smith |
| D543,212 S | 5/2007 | Marks |
| 7,265,298 B2 | 9/2007 | Maghribi et al. |
| 7,271,774 B2 | 9/2007 | Puuri |
| 7,333,090 B2 | 2/2008 | Tanaka et al. |
| 7,351,975 B2 | 4/2008 | Brady et al. |
| 7,450,107 B2 | 11/2008 | Radley-Smith |
| 7,491,892 B2 | 2/2009 | Wagner et al. |
| 7,517,725 B2 | 4/2009 | Reis |
| 7,558,622 B2 | 7/2009 | Tran |
| 7,574,253 B2 | 8/2009 | Edney et al. |
| 7,580,742 B2 | 8/2009 | Tan et al. |
| 7,596,393 B2 | 9/2009 | Jung et al. |
| 7,618,260 B2 | 11/2009 | Daniel et al. |
| 7,636,549 B2 | 12/2009 | Ma et al. |
| 7,640,007 B2 | 12/2009 | Chen et al. |
| 7,660,126 B2 | 2/2010 | Cho et al. |
| 7,787,946 B2 | 8/2010 | Stahmann et al. |
| 7,805,386 B2 | 9/2010 | Greer |
| 7,809,435 B1 | 10/2010 | Ettare et al. |
| 7,844,310 B2 | 11/2010 | Anderson |
| 7,870,211 B2 | 1/2011 | Pascal et al. |
| 7,901,368 B2 | 3/2011 | Flaherty et al. |
| 7,925,100 B2 | 4/2011 | Howell et al. |
| 7,948,763 B2 | 5/2011 | Chuang |
| D643,428 S | 8/2011 | Janky et al. |
| D646,192 S | 10/2011 | Woode |
| 8,054,061 B2 | 11/2011 | Prance et al. |
| D654,622 S | 2/2012 | Hsu |
| 8,170,656 B2 | 5/2012 | Tan et al. |
| 8,179,604 B1 | 5/2012 | Prada Gomez et al. |
| 8,188,937 B1 | 5/2012 | Amafuji et al. |
| 8,190,249 B1 | 5/2012 | Gharieb et al. |
| D661,613 S | 6/2012 | Demeglio |
| 8,203,502 B1 | 6/2012 | Chi et al. |
| 8,207,473 B2 | 6/2012 | Axisa et al. |
| 8,212,859 B2 | 7/2012 | Tang et al. |
| 8,311,623 B2 | 11/2012 | Sanger |
| 8,351,651 B2 | 1/2013 | Lee |
| 8,355,671 B2 | 1/2013 | Kramer et al. |
| 8,389,862 B2 | 4/2013 | Arora et al. |
| 8,421,634 B2 | 4/2013 | Tan et al. |
| 8,427,977 B2 | 4/2013 | Workman et al. |
| D682,727 S | 5/2013 | Bulgari |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,467,270 B2 | 6/2013 | Gossweiler, III et al. |
| 8,469,741 B2 | 6/2013 | Oster et al. |
| 8,484,022 B1 | 7/2013 | Vanhoucke |
| D689,862 S | 9/2013 | Liu |
| 8,591,411 B2 | 11/2013 | Banet et al. |
| D695,454 S | 12/2013 | Moore |
| 8,620,361 B2 | 12/2013 | Bailey et al. |
| 8,624,124 B2 | 1/2014 | Koo et al. |
| 8,702,629 B2 | 4/2014 | Giuffrida et al. |
| 8,704,882 B2 | 4/2014 | Turner |
| 8,718,980 B2 | 5/2014 | Garudadri et al. |
| 8,744,543 B2 | 6/2014 | Li et al. |
| 8,754,862 B2 | 6/2014 | Zaliva |
| 8,777,668 B2 | 7/2014 | Ikeda et al. |
| D716,457 S | 10/2014 | Brefka et al. |
| D717,685 S | 11/2014 | Bailey et al. |
| 8,879,276 B2 | 11/2014 | Wang |
| 8,880,163 B2 | 11/2014 | Barachant et al. |
| 8,883,287 B2 | 11/2014 | Boyce et al. |
| 8,890,875 B2 | 11/2014 | Jammes et al. |

(56) References Cited

U.S. PATENT DOCUMENTS

| | | |
|---|---|---|
| 8,892,479 B2 | 11/2014 | Tan et al. |
| 8,895,865 B2 | 11/2014 | Lenahan et al. |
| 8,912,094 B2 | 12/2014 | Koo et al. |
| 8,922,481 B1 | 12/2014 | Kauffman et al. |
| 8,970,571 B1 | 3/2015 | Wong et al. |
| 8,971,023 B2 | 3/2015 | Olsson et al. |
| 9,018,532 B2 | 4/2015 | Wesselmann et al. |
| 9,037,530 B2 | 5/2015 | Tan et al. |
| 9,086,687 B2 | 7/2015 | Park et al. |
| 9,092,664 B2 | 7/2015 | Forutanpour et al. |
| D736,664 S | 8/2015 | Paradise et al. |
| 9,146,730 B2 | 9/2015 | Lazar |
| D741,855 S | 10/2015 | Park et al. |
| 9,170,674 B2 | 10/2015 | Forutanpour et al. |
| D742,272 S | 11/2015 | Bailey et al. |
| D742,874 S | 11/2015 | Cheng et al. |
| D743,963 S | 11/2015 | Osterhout |
| 9,182,826 B2 | 11/2015 | Powledge et al. |
| 9,211,417 B2 | 12/2015 | Heldman et al. |
| 9,218,574 B2 | 12/2015 | Phillipps et al. |
| D747,714 S | 1/2016 | Erbeus |
| 9,235,934 B2 | 1/2016 | Mandella et al. |
| 9,240,069 B1 | 1/2016 | Li |
| D750,623 S | 3/2016 | Park et al. |
| D751,065 S | 3/2016 | Magi |
| 9,278,453 B2 | 3/2016 | Assad |
| 9,299,248 B2 | 3/2016 | Lake et al. |
| D756,359 S | 5/2016 | Bailey et al. |
| 9,351,653 B1 | 5/2016 | Harrison |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,393,418 B2 | 7/2016 | Giuffrida et al. |
| 9,408,316 B2 | 8/2016 | Bailey et al. |
| 9,418,927 B2 | 8/2016 | Axisa et al. |
| 9,439,566 B2 | 9/2016 | Arne et al. |
| 9,459,697 B2 | 10/2016 | Bedikian et al. |
| 9,472,956 B2 | 10/2016 | Michaelis et al. |
| 9,477,313 B2 | 10/2016 | Mistry et al. |
| 9,483,123 B2 | 11/2016 | Aleem et al. |
| 9,529,434 B2 | 12/2016 | Choi et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 10,592,001 B2 | 3/2020 | Berenzweig et al. |
| 2002/0032386 A1 | 3/2002 | Snackner et al. |
| 2002/0077534 A1 | 6/2002 | DuRousseau |
| 2002/0094701 A1* | 7/2002 | Biegelsen ............ H01L 25/0655 439/32 |
| 2003/0036691 A1 | 2/2003 | Stanaland et al. |
| 2003/0051505 A1 | 3/2003 | Robertson et al. |
| 2003/0144586 A1 | 7/2003 | Tsubata |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0054273 A1 | 3/2004 | Finneran et al. |
| 2004/0068409 A1 | 4/2004 | Tanaka et al. |
| 2004/0073104 A1 | 4/2004 | Brun del Re et al. |
| 2004/0092839 A1 | 5/2004 | Shin et al. |
| 2004/0194500 A1 | 10/2004 | Rapport |
| 2004/0210165 A1 | 10/2004 | Marmaropoulos et al. |
| 2004/0243342 A1 | 12/2004 | Rekimoto |
| 2005/0005637 A1 | 1/2005 | Rapport |
| 2005/0012715 A1 | 1/2005 | Ford |
| 2005/0070227 A1 | 3/2005 | Shen et al. |
| 2005/0119701 A1 | 6/2005 | Lauter et al. |
| 2005/0177038 A1 | 8/2005 | Kolpin et al. |
| 2006/0037359 A1 | 2/2006 | Stinespring |
| 2006/0061544 A1 | 3/2006 | Min et al. |
| 2006/0121958 A1 | 6/2006 | Fung et al. |
| 2006/0129057 A1 | 6/2006 | Maekawa et al. |
| 2007/0009151 A1 | 1/2007 | Pittman et al. |
| 2007/0016265 A1 | 1/2007 | Davoodi et al. |
| 2007/0132785 A1 | 6/2007 | Ebersole, Jr. et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0051673 A1 | 2/2008 | Kong et al. |
| 2008/0052643 A1 | 2/2008 | Ike et al. |
| 2008/0103639 A1 | 5/2008 | Troy et al. |
| 2008/0103769 A1 | 5/2008 | Schultz et al. |
| 2008/0136775 A1 | 6/2008 | Conant |
| 2008/0214360 A1 | 9/2008 | Stirling et al. |
| 2008/0221487 A1 | 9/2008 | Zohar et al. |
| 2008/0262772 A1 | 10/2008 | Luinge et al. |
| 2009/0007597 A1 | 1/2009 | Hanevold |
| 2009/0027337 A1 | 1/2009 | Hildreth |
| 2009/0031757 A1 | 2/2009 | Harding |
| 2009/0040016 A1 | 2/2009 | Ikeda |
| 2009/0051544 A1 | 2/2009 | Niknejad |
| 2009/0079813 A1 | 3/2009 | Hildreth |
| 2009/0082692 A1 | 3/2009 | Hale et al. |
| 2009/0082701 A1* | 3/2009 | Zohar ............... A61B 5/103 600/595 |
| 2009/0102580 A1 | 4/2009 | Uchaykin |
| 2009/0112080 A1 | 4/2009 | Matthews |
| 2009/0124881 A1 | 5/2009 | Rytky |
| 2009/0189867 A1 | 7/2009 | Krah et al. |
| 2009/0251407 A1 | 10/2009 | Flake et al. |
| 2009/0318785 A1 | 12/2009 | Ishikawa et al. |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0041974 A1 | 2/2010 | Ting et al. |
| 2010/0063794 A1* | 3/2010 | Hernandez-Rebollar .................... G06K 9/00355 704/3 |
| 2010/0106044 A1 | 4/2010 | Linderman |
| 2010/0113910 A1 | 5/2010 | Brauers et al. |
| 2010/0228487 A1 | 9/2010 | Luethardt et al. |
| 2010/0249635 A1 | 9/2010 | Van Der Reijden |
| 2010/0280628 A1 | 11/2010 | Sankai |
| 2010/0292595 A1 | 11/2010 | Paul |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2010/0317958 A1 | 12/2010 | Bech et al. |
| 2011/0018754 A1 | 1/2011 | Tojima et al. |
| 2011/0077484 A1 | 3/2011 | Van Slyke et al. |

(56) References Cited

U.S. PATENT DOCUMENTS

| | | |
|---|---|---|
| 2011/0092826 A1 | 4/2011 | Lee et al. |
| 2011/0134026 A1 | 6/2011 | Kang et al. |
| 2011/0151974 A1 | 6/2011 | Deaguero |
| 2011/0166434 A1 | 7/2011 | Gargiulo |
| 2011/0172503 A1 | 7/2011 | Knepper et al. |
| 2011/0173204 A1 | 7/2011 | Murillo et al. |
| 2011/0173574 A1 | 7/2011 | Clavin et al. |
| 2011/0213278 A1 | 9/2011 | Horak et al. |
| 2011/0224556 A1 | 9/2011 | Moon et al. |
| 2011/0224564 A1 | 9/2011 | Moon et al. |
| 2011/0230782 A1 | 9/2011 | Bartol et al. |
| 2011/0248914 A1 | 10/2011 | Sherr |
| 2011/0313762 A1 | 12/2011 | Ben-David et al. |
| 2012/0029322 A1 | 2/2012 | Wartena et al. |
| 2012/0051005 A1 | 3/2012 | Vanfleteren et al. |
| 2012/0066163 A1 | 3/2012 | Balls et al. |
| 2012/0101357 A1 | 4/2012 | Hoskuldsson et al. |
| 2012/0157789 A1 | 6/2012 | Kangas et al. |
| 2012/0165695 A1 | 6/2012 | Kidmose et al. |
| 2012/0188158 A1 | 7/2012 | Tan et al. |
| 2012/0203076 A1 | 8/2012 | Fatta et al. |
| 2012/0209134 A1 | 8/2012 | Morita et al. |
| 2012/0265090 A1 | 10/2012 | Fink et al. |
| 2012/0265480 A1 | 10/2012 | Oshima |
| 2012/0283526 A1 | 11/2012 | Gommesen et al. |
| 2012/0293548 A1 | 11/2012 | Perez et al. |
| 2012/0302858 A1 | 11/2012 | Kidmose et al. |
| 2012/0323521 A1 | 12/2012 | De Foras et al. |
| 2013/0004033 A1 | 1/2013 | Trugenberger |
| 2013/0005303 A1 | 1/2013 | Song et al. |
| 2013/0020948 A1 | 1/2013 | Han et al. |
| 2013/0027341 A1 | 1/2013 | Mastandrea |
| 2013/0077820 A1 | 3/2013 | Marais et al. |
| 2013/0080794 A1 | 3/2013 | Hsieh |
| 2013/0123656 A1 | 5/2013 | Heck |
| 2013/0127708 A1 | 5/2013 | Jung et al. |
| 2013/0141375 A1 | 6/2013 | Ludwig et al. |
| 2013/0165813 A1 | 6/2013 | Chang et al. |
| 2013/0191741 A1 | 7/2013 | Dickinson et al. |
| 2013/0198694 A1 | 8/2013 | Rahman et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0265229 A1 | 10/2013 | Forutanpour et al. |
| 2013/0265437 A1 | 10/2013 | Thorn et al. |
| 2013/0271292 A1 | 10/2013 | McDermott |
| 2013/0312256 A1 | 11/2013 | Wesselmann et al. |
| 2013/0317382 A1 | 11/2013 | Le |
| 2013/0317648 A1 | 11/2013 | Assad |
| 2013/0332196 A1 | 12/2013 | Pinsker |
| 2014/0020945 A1 | 1/2014 | Hurwitz et al. |
| 2014/0028546 A1 | 1/2014 | Jeon et al. |
| 2014/0045547 A1 | 2/2014 | Singamsetty et al. |
| 2014/0049417 A1 | 2/2014 | Abdurrahman et al. |
| 2014/0052150 A1 | 2/2014 | Taylor et al. |
| 2014/0121471 A1 | 3/2014 | Walker |
| 2014/0122958 A1 | 3/2014 | Greenebrg et al. |
| 2014/0092009 A1 | 4/2014 | Yen et al. |
| 2014/0094675 A1 | 4/2014 | Luna et al. |
| 2014/0098018 A1 | 4/2014 | Kim et al. |
| 2014/0107493 A1 | 4/2014 | Yuen et al. |
| 2014/0142937 A1 | 5/2014 | Powledge et al. |
| 2014/0194062 A1 | 7/2014 | Palin et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0198944 A1 | 7/2014 | Forutanpour et al. |
| 2014/0223462 A1 | 8/2014 | Aimone et al. |
| 2014/0236031 A1 | 8/2014 | Banet et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0257141 A1 | 9/2014 | Giuffrida et al. |
| 2014/0277622 A1 | 9/2014 | Raniere |
| 2014/0278441 A1 | 9/2014 | Ton et al. |
| 2014/0285326 A1 | 9/2014 | Luna et al. |
| 2014/0297528 A1 | 10/2014 | Agrawal et al. |
| 2014/0299362 A1 | 10/2014 | Park et al. |
| 2014/0304665 A1 | 10/2014 | Holz |
| 2014/0310595 A1 | 10/2014 | Acharya et al. |
| 2014/0330404 A1 | 11/2014 | Abdelghani et al. |
| 2014/0334083 A1 | 11/2014 | Bailey |
| 2014/0334653 A1 | 11/2014 | Luna et al. |
| 2014/0337861 A1 | 11/2014 | Chang et al. |
| 2014/0340857 A1 | 11/2014 | Hsu et al. |
| 2014/0344731 A1 | 11/2014 | Holz |
| 2014/0349257 A1 | 11/2014 | Connor |
| 2014/0354528 A1 | 12/2014 | Laughlin et al. |
| 2014/0354529 A1 | 12/2014 | Laughlin et al. |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |
| 2014/0365163 A1 | 12/2014 | Jallon |
| 2014/0375465 A1 | 12/2014 | Fenuccio et al. |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0011857 A1 | 1/2015 | Henson et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057506 A1 | 2/2015 | Luna et al. |
| 2015/0057770 A1 | 2/2015 | Bailey et al. |
| 2015/0065840 A1 | 3/2015 | Bailey |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0094564 A1 | 4/2015 | Tashman et al. |
| 2015/0106052 A1 | 4/2015 | Balakrishnan et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0160621 A1 | 6/2015 | Yilmaz |
| 2015/0169074 A1 | 6/2015 | Ataee et al. |
| 2015/0182113 A1 | 7/2015 | Utter, II |
| 2015/0182130 A1 | 7/2015 | Utter, II |
| 2015/0182160 A1 | 7/2015 | Kim et al. |
| 2015/0182163 A1 | 7/2015 | Utter |
| 2015/0182164 A1 | 7/2015 | Utter, II |
| 2015/0182165 A1 | 7/2015 | Miller et al. |
| 2015/0186609 A1 | 7/2015 | Utter, II |
| 2015/0193949 A1 | 7/2015 | Katz et al. |
| 2015/0216475 A1 | 8/2015 | Luna et al. |
| 2015/0220152 A1 | 8/2015 | Tait et al. |
| 2015/0223716 A1 | 8/2015 | Korkala et al. |
| 2015/0230756 A1 | 8/2015 | Luna et al. |
| 2015/0234426 A1 | 8/2015 | Bailey et al. |
| 2015/0237716 A1 | 8/2015 | Su et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0309563 A1 | 10/2015 | Connor |
| 2015/0309582 A1 | 10/2015 | Gupta |
| 2015/0312175 A1 | 10/2015 | Langholz |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1* | 12/2015 | Connor .............. A61B 5/0492 600/301 |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0020500 A1 | 1/2016 | Matsuda |

(56) References Cited

U.S. PATENT DOCUMENTS

| | | |
|---|---|---|
| 2016/0026853 A1* | 1/2016 | Wexler ............... H04N 5/2254 382/103 |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0150636 A1 | 5/2016 | Otsubo |
| 2016/0156762 A1 | 6/2016 | Bailey et al. |
| 2016/0162604 A1 | 6/2016 | Xiaoli et al. |
| 2016/0187992 A1 | 6/2016 | Yamamoto et al. |
| 2016/0199699 A1 | 7/2016 | Klassen |
| 2016/0202081 A1 | 7/2016 | Debieuvre et al. |
| 2016/0207201 A1 | 7/2016 | Herr et al. |
| 2016/0235323 A1 | 8/2016 | Tadi et al. |
| 2016/0239080 A1 | 8/2016 | Marcolina et al. |
| 2016/0259407 A1* | 9/2016 | Schick ................. G06F 3/0219 |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0309249 A1 | 10/2016 | Wu et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188878 A1 | 7/2017 | Lee |
| 2017/0188980 A1 | 7/2017 | Ash |
| 2017/0197142 A1* | 7/2017 | Stafford ............... A63F 13/5255 |
| 2017/0259167 A1 | 9/2017 | Cook et al. |
| 2017/0262064 A1 | 9/2017 | Ofir et al. |
| 2017/0285756 A1* | 10/2017 | Wang .................. G06F 3/0346 |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1* | 10/2017 | Ito ....................... G06F 3/017 |
| 2017/0344706 A1 | 11/2017 | Torres et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0024641 A1* | 1/2018 | Mao ..................... G06T 7/251 382/103 |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0092599 A1 | 4/2018 | Kerth et al. |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0240459 A1 | 8/2018 | Weng et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0247650 A1 | 8/2019 | Tran |
| 2019/0324549 A1 | 10/2019 | Araki et al. |
| 2019/0348026 A1 | 11/2019 | Berenzweig et al. |
| 2019/0348027 A1 | 11/2019 | Berenzweig et al. |
| 2019/0357787 A1 | 11/2019 | Barachant et al. |
| 2019/0362557 A1 | 11/2019 | Lacey et al. |
| 2020/0069210 A1 | 3/2020 | Berenzweig et al. |
| 2020/0073483 A1 | 3/2020 | Berenzweig et al. |
| 2020/0097081 A1 | 3/2020 | Stone et al. |

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| CN | 110300542 A | 10/2019 |
| DE | 44 12 278 A1 | 10/1995 |
| EP | 0 301 790 A2 | 2/1989 |
| EP | 2198521 B1 | 6/2012 |
| EP | 2959394 A1 | 12/2015 |
| EP | 3104737 A1 | 12/2016 |
| EP | 3 487 395 A1 | 5/2019 |
| JP | H05-277080 A | 10/1993 |
| JP | 2005-095561 A | 4/2005 |
| JP | 2009-50679 A | 3/2009 |
| JP | 2010-520561 A | 6/2010 |
| JP | 2016-507851 A | 3/2016 |
| JP | 2017-509386 A | 4/2017 |
| KR | 10-2012-0094870 A | 8/2012 |
| KR | 10-2012-0097997 A | 9/2012 |
| KR | 2015-0123254 A | 11/2015 |
| KR | 2016-0121552 A | 10/2016 |
| KR | 10-2017-0107283 A | 9/2017 |
| KR | 10-1790147 B1 | 10/2017 |
| WO | WO 2008/109248 A2 | 9/2008 |
| WO | WO 2009/042313 A1 | 4/2009 |
| WO | WO 2010/104879 A2 | 9/2010 |
| WO | 2011/070554 A2 | 6/2011 |
| WO | WO 2012/155157 A1 | 11/2012 |
| WO | WO 2014/130871 A1 | 8/2014 |
| WO | WO 2014/186370 A1 | 11/2014 |
| WO | WO 2014/194257 A1 | 12/2014 |
| WO | WO 2014/197443 A1 | 12/2014 |
| WO | WO 2015/027089 A1 | 2/2015 |
| WO | WO 2015/073713 A1 | 5/2015 |
| WO | WO 2015/081113 A1 | 6/2015 |
| WO | WO 2015/123445 A1 | 8/2015 |
| WO | WO 2015/199747 A1 | 12/2015 |
| WO | WO 2016/041088 A1 | 3/2016 |
| WO | WO 2017/062544 A1 | 4/2017 |
| WO | WO 2017/092225 A1 | 6/2017 |
| WO | WO 2017/120669 A1 | 7/2017 |
| WO | WO 2017/172185 A1 | 10/2017 |
| WO | WO 2017/208167 A1 | 12/2017 |
| WO | 2018/022602 A1 | 2/2018 |

(56) References Cited

FOREIGN PATENT DOCUMENTS

| WO | 2019/099758 A1 | 5/2019 |
|---|---|---|
| WO | 2019/217419 A2 | 11/2019 |
| WO | 2020/047429 A1 | 3/2020 |
| WO | 2020/061440 A1 | 3/2020 |

OTHER PUBLICATIONS

PCT/US2017/043686, Feb. 7, 2019, International Preliminary Report on Patentability.
PCT/US2017/043693, Oct, 6, 2017, International Search Report and Written Opinion.
PCT/US2017/043693, Feb. 7, 2019, International Preliminary Report on Patentability.
PCT/US2017/043791, Oct. 5, 2017, International Search Report and Written Opinion.
PCT/US2017/043791, Feb. 7, 2019, International Preliminary Report on Patentability.
PCT/US2017/043792, Oct. 5, 2017, International Search Report and Written Opinion.
PCT/US2017/043792, Feb. 7, 2019, International Preiiminary Report on Patentability.
PCT/US2018/056768, Jan. 15, 2019, International Search Report and Written Opinion.
PCT/US2018/061409, Mar. 12, 2019, International Search Report and Written Opinion.
PCT/US2018/063215, Mar. 21, 2019, International Search Report and Written Opinion.
PCT/US2019/015134, May 15, 2019, International Search Report and Written Opinion.
PCT/US2019/015167, May 21, 2019, International Search Report and Written Opinion.
PCT/US2019/015174, May 21, 2019, International Search Report and Written Opinion.
PCT/US2019/015238, May 16, 2019, International Search Report and Written Opinion.
PCT/US2019/015183, May 3, 2019, International Search Report and Written Opinion.
PCT/US2019/015180, May 28, 2019, International Search Report and Written Opinion.
PCT/US2019/015244, May 16, 2019, International Search Report and Written Opinion.
PCT/US19/20065, May 16, 2019, International Search Report and Written Opinion.
PCT/US2019/031114, Aug. 6, 2019, Invitation to Pay Additional Fees.
PCT/US2019/028299, Aug. 9, 2019, International Search Report and Written Opinion.
PCT/US2019/034173, Sep. 18, 2019, International Search Report and Written Opinion.
PCT/US2019/037302, Oct. 11, 2019, International Search Report and Written Opinion.
PCT/US2019/049094, Oct. 24, 2019, Invitation to Pay Additional Fees.
PCT/US2019/042579, Oct. 31, 2019, International Search Report and Written Opinion.
PCT/US2019/046351, Nov. 7, 2019, International Search Report and Written Opinion.
International Search Report and Written Opinion for International Application No. PCT/US2017/043686 dated Oct. 6, 2017.
International Preliminary Report on Patentability for International Application No. PCT/US2017/043686 dated Feb. 7, 2019.
International Search Report and Written Opinion for International Application No. PCT/US2017/043693 dated Oct. 6, 2017.
International Preliminary Report on Patentability for International Application No. PCT/US2017/043693 dated Feb. 7, 2019.
International Search Report and Written Opinion for International Application No. PCT/US2017/043791 dated Oct. 5, 2017.
International Preliminary Report on Patentability for International Application No. PCT/US2017/043791 dated Feb. 7, 2019.
International Search Report and Written Opinion for International Application No. PCT/US2017/043792 dated Oct. 5, 2017.
International Preliminary Report on Patentability for International Application No. PCT/US2017/043792 dated Feb. 7, 2019.
International Search Report and Written Opinion for International Application No. PCT/US2018/056768 dated Jan. 15, 2019.
International Search Report and Written Opinion for International Application No. PCT/US2018/061409 dated Mar. 12, 2019.
International Search Report and Written Opinion for International Application No. PCT/US2018/063215 dated Mar. 21, 2019.
International Search Report and Written Opinion for International Application No. PCT/US2019/015134 dated May 15, 2019.
International Search Report and Written Opinion for International Application No. PCT/US2019/015167 dated May 21, 2019.
International Search Report and Written Opinion for International Application No. PCT/US2019/015174 dated May 21, 2019.
International Search Report and Written Opinion for International Application No. PCT/US2019/015238 dated May 16, 2019.
International Search Report and Written Opinion for International Application No. PCT/US2019/015183 dated May 3, 2019.
International Search Report and Written Opinion for International Application No. PCT/US2019/015180 dated May 28, 2019.
International Search Report and Written Opinion for International Application No. PCT/US2019/015244 dated May 16, 2019.
International Search Report and Written Opinion for International Application No. PCT/US19/20065 dated May 16, 2019.
Invitation to Pay Additional Fees for International Application No. PCT/US2019/031114 dated Aug. 6, 2019.
International Search Report and Written Opinion for International Application No. PCT/US2019/028299 dated Aug. 9, 2019.
International Search Report and Written Opinion for International Application No. PCT/US2019/034173 dated Sep. 18, 2019.
International Search Report and Written Opinion for International Application No. PCT/US2019/037302 dated Oct. 11, 2019.
Invitation to Pay Additional Fees for International Application No. PCT/US2019/049094 dated Oct. 24, 2019.
International Search Report and Written Opinion for International Application No. PCT/US2019/042579 dated Oct. 31, 2019.
International Search Report and Written Opinion for International Application No. PCT/US2019/046351 dated Nov. 7, 2019.
Arkenbout et al., "Robust Hand Motion Tracking through Data Fusion of 5DT Data Glove and Nimble VR Kinect Camera Measurements," Sensors, 2015, vol. 15, pp. 31644-31671.
Benko et al., "Enhancing Input On and Above the Interactive Surface with Muscle Sensing," The ACM International Conference on Interactive Tabletops and Surfaces, ITS '09, 2009, pp. 93-100.
Boyali et al., "Spectral Collaborative Representation based Classification for hand gestures recognition on electromyography signals," Biomedical Signal Processing and Control, 2016, vol. 24, pp. 11-18.
Cheng et al., "A Novel Phonology- and Radical-Coded Chinese Sign Language Recognition Framework Using Accelerometer and Surface Electromyography Sensors," Sensors, 2015, vol. 15, pp. 23303-23324.
Csapo et al., "Evaluation of Human-Myo Gesture Control Capabilities in Continuous Search and Select Operations," 7th IEEE International Conference on Cognitive Infocommunications, 2016, pp. 000415-000420.
Davoodi et al., "Development of a Physics-Based Target Shooting Game to Train Amputee Users of Multijoint Upper Limb Prostheses," Presence, Massachusetts Institute of Technology, 2012, vol. 21(1), pp. 85-95.
Delis et al., "Development of a Myoelectric Controller Based on Knee Angle Estimation," Biodevices 2009, International Conference on Biomedical Electronics and Devices Jan. 17, 2009, pp. 97-103.
Diener et al., "Direct conversion from facial myoelectric signals to speech using Deep Neural Networks," 2015 International Joint Conference on Neural Networks (IJCNN), Oct. 1, 2015, 7 pages.

(56) References Cited

OTHER PUBLICATIONS

Ding et al., "HMM with improved feature extraction-based feature parameters for identity recognition of gesture command operators by using a sensed Kinect-data stream," Neurocomputing, 2017, vol. 262, pp. 108-119.
Farina et al., "Man/machine interface based on the discharge timings of spinal motor neurons after targeted muscle reinnervation," Nature: Biomedical Engineering, 2017, vol. 1(25), pp. 1-12.
Favorskaya et al., "Localization and Recognition of Dynamic Hand Gestures Based on Hierarchy of Manifold Classifiers," International Archives of the Photogrammetry, Remote Sensing and Spatial Information Sciences, 2015, vol. XL-5/W6, pp. 1-8.
Gallina et al., "Surface EMG Biofeedback. Surface Electromyography: Physiology, Engineering, and Applications," John Wiley & Sons, Inc., edited by Merletti et al., 2016, pp. 485-500.
Gopura et al., "A Human Forearm and wrist motion assist exoskeleton robot with EMG-based fuzzy-neuro control," Proceedings of the 2nd IEEE/RAS-EMBS International Conference on Biomedical Robotics and Biomechatronics, Oct. 19-22, 2008, pp. 550-555.
Hauschild et al., "A Virtual Reality Environment for Designing and Fitting Neural Prosthetic Limbs," IEEE Transactions on Neural Systems and Rehabilitation Engineering, 2007, vol. 15(1), pp. 9-15.
Jiang, "Effective and Interactive Interpretation of Gestures by Individuals with Mobility Impairments," Purdue University Graduate School Thesis/Dissertation Acceptance, 2015, 24 pages.
Kawaguchi et al., "Estimation of Finger Joint Angles Based on Electromechanical Sensing of Wrist Shape," IEEE Transactions on Neural Systems and Rehabilitation Engineering, 2017, vol. 25(9), pp. 1409-1418.
Kim et al., "Real-Time Human Pose Estimation and Gesture Recognition from Depth Images Using Superpixels and SVM Classifier," Sensors, 2015, vol. 15, pp. 12410-12427.
Kipke et al., "Silicon-substrate Intracortical Microelectrode Arrays for Long-Term Recording of Neuronal Spike Activity in Cerebral Cortex," IEEE Transactions on Neural Systems and Rehabilitation Engineering, 2003, vol. 11(2), pp. 151-155.
Koerner, "Design and Characterization of the Exo-Skin Haptic Device: A Novel Tendon Actuated Textile Hand Exoskeleton," abstract of thesis for Drexel University Masters Degree, 2017, 5 pages.
Lee et al., "Motion and Force Estimation System of Human Fingers," Journal of Institute of Control, Robotics and Systems, 2011, vol. 17(10), pp. 1014-1020 (in Korean).
Li et al., "Motor Function Evaluation of Hemiplegic Upper-Extremities Using Data Fusion from Wearable Inertial and Surface EMG Sensors," Sensors, 2017, vol. 17(582), 17 pages.
Lopes et al., "Hand/arm gesture segmentation by motion using IMU and EMG sensing," Procedia Manufacturing, 2017, vol. 11, pp. 107-113.
Martin et al., "A Novel Approach of Prosthetic Arm Control using Computer Vision, Biosignals, and Motion Capture," IEEE Symposium on Computational Intelligence in Robotic Rehabilitation and Assistive Technologies (CIR2AT), 2014, 5 pages.
Mcintee, "A Task Model of Free-Space Movement-Based Gestures," Ph.D. Dissertation submitted to Graduate Faculty of North Carolina State University (Raleigh), 2016, 129 pages.
Mendes et al., "Sensor Fusion and Smart Sensor in Sports and Biomedical Applications," Sensors, 2016, vol. 16(1569), 31 pages.
Mohamed, "Homogeneous cognitive based biometrics for static authentication," Ph.D. Dissertation submitted to University of Victoria, Canada, 2010, 149 pages.
Naik et al., "Source Separation and Identification issues in bio signals: A solution using Blind source separation," chapter 4 of Recent Advances in Biomedical Engineering, Intech, 2009, 23 pages.
Naik et al., "Subtle Hand gesture identification for HCI using Temporal Decorrelation Source Separation BSS of surface EMG," Digital Image Computing Techniques and Applications, IEEE Computer Society, 2007, pp. 30-37.

Negro et al., "Multi-channel intramuscular and surface EMG decomposition by convolutive blind source separation," Journal of Neural Engineering, 2016, vol. 13, 17 pages.
Saponas et al., "Demonstrating the Feasibility of Using Forearm Electromyography for Muscle-Computer Interfaces," CHI 2008 Proceedings, Physiological Sensing for Input, 2008, pp. 515-524.
Saponas et al., "Enabling Always-Available Input with Muscle-Computer Interfaces," UIST '09, 2009,pp. 167-176.
Saponas et al., "Making Muscle-Computer Interfaces More Practical," CHI 2010, Brains and Brawn, 2010, pp. 851-854.
Sartori et al., "Neural Data-Driven Musculoskeletal Modeling for Personalized Neurorehabilitation Technologies," IEEE Transactions on Biomedical Engineering, 2016, vol. 63(5), pp. 879-893.
Sauras-Perez, "A Voice and Pointing Gesture Interaction System for Supporting Human Spontaneous Decisions in Autonomous Cars," Ph.D. Dissertation submitted to Clemson University, 2017, 174 pages.
Shen et al., "I am a Smartwatch and I can Track my User's Arm," MobiSys '16, 2016, 12 pages.
Son et al., "Evaluating the utility of two gestural discomfort evaluation methods," PLoS One, 2017, vol. 12(4), 21 pages.
Strbac et al., "Microsoft Kinect-Based Artificial Perception System for Control of Functional Electrical Stimulation Assisted Grasping," BioMed Research International, Hindawi Publishing Corporation, 2014, 13 pages.
Torres, "Myo Gesture Control Armband," PCMag, https://www.pcmag.com/article2/0,2817,2485462,00.asp, 2015, 9 pages.
Valero-Cuevas et al., "Computational Models for Neuromuscular Function," author manuscript submitted to IEEE Review of Biomedical Engineering, 2009, 52 pages.
Wodzinski et al., "Sequential Classification of Palm Gestures Based on A* Algorithm and MLP Neural Network for Quadrocopter Control," Metrol. Meas. Syst., 2017, vol. 24(2), pp. 265-276.
Xue et al., "Multiple Sensors Based Hand Motion Recognition Using Adaptive Directed Acyclic Graph," Applied Sciences, 2017, vol. 7(358), 14 pages.
Yang et al., "Surface EMG based handgrip force predictions using gene expression programming," Neurocomputing, 2016, vol. 207, pp. 568-579.
Final Office Action received for U.S. Appl. No. 16/577,207 dated Feb. 4, 2020, 76 pages.
Non-Final Office Action received for U.S. Appl. No. 15/974,430 dated May 16, 2019, 12 pages.
Final Office Action received for U.S. Appl. No. 15/974,430 dated Dec. 11, 2019, 30 pages.
Non-Final Office Action received for U.S. Appl. No. 15/974,384 dated May 16, 2019, 13 pages.
Notice of Allowance received for U.S. Appl. No. 15/974,384 dated Nov. 4, 2019, 39 pages.
Berenzweig et al., "Wearable Devices and Methods for Improved Speech Recognition", U.S. Appl. No. 16/785,680, filed Feb. 10, 2020, 67 pages.
Non-Final Office Action received for U.S. Appl. No. 15/974,454 dated Dec. 20, 2019, 41 pages.
Final Office Action received for U.S. Appl. No. 15/974,454 dated Apr. 9, 2020, 19 pages.
International Search Report and Written Opinion received for PCT Application Serial No. PCT/US2019/031114 dated Dec. 20, 2019, 18 pages.
Costanza et al., "EMG as a Subtle Input Interface for Mobile Computing", Mobile HCI 2004, LNCS 3160, edited by S. Brewster and M. Dunlop, Springer-Verlag Berlin Heidelberg, pp. 426-430, 2004.
Costanza et al., "Toward Subtle Intimate Interfaces for Mobile Devices Using an EMG Controller", CHI 2005, Proceedings of the SIGCHI Conference on Human Factors in Computing Systems, pp. 481-489, 2005.
Ghasemzadeh et al., "A Body Sensor Network With Electromyogram and Inertial Sensors: Multimodal Interpretation of Muscular Activities", IEEE Transactions on Information Technology in Biomedicine, vol. 14, No. 2, pp. 198-206, Mar. 2010.

(56) References Cited

OTHER PUBLICATIONS

Gourmelon et al., "Contactless sensors for Surface Electromyography", Proceedings of the 28th IEEE EMBS Annual International Conference, New York City, NY, Aug. 30-Sep. 3, 2006, pp. 2514-2517.

International Search Report and Written Opinion, dated May 16, 2014, for corresponding International Application No. PCT/US2014/017799, 9 pages.

International Search Report and Written Opinion, dated Aug. 21, 2014, for corresponding International Application No. PCT/US2014/037863, 10 pages.

International Search Report and Written Opinion, dated Nov. 21, 2014, for corresponding International Application No. PCT/US2014/052143, 9 pages.

International Search Report and Written Opinion, dated Feb. 27, 2015, for corresponding International Application No. PCT/US2014/067443, 10 pages.

International Search Report and Written Opinion, dated May 27, 2015, for corresponding International Application No. PCT/US2015/015675, 9 pages.

Morris et al., "Emerging Input Technologies for Always-Available Mobile Interaction", Foundations and Trends in Human-Computer Interaction 4(4):245-316, 2010. (74 total pages).

Naik et al., "Real-Time Hand Gesture Identification for Human Computer Interaction Based on ICA of Surface Electromyogram", IADIS International Conference Interfaces and Human Computer Interaction, 2007, 8 pages.

Picard et al., "Affective Wearables", Proceedings of the IEEE 1st International Symposium on Wearable Computers, SWC, Cambridge, MA, USA, Oct. 13-14, 1997, pp. 90-97.

Rekimoto, "Gesture Wrist and GesturePad: Unobtrusive Wearable Interaction Devices", ISWC '01 Proceedings of the 5th IEEE International Symposium on Wearable Computers, 2001, 7 pages.

Final Office Action received for U.S. Appl. No. 14/505,836 dated Jul. 28, 2017, 52 pages.

Sato et al., "Touche: Enhancing Touch Interaction on Humans, Screens, Liquids, and Everyday Objects", CHI'12, May 5-10, 2012, Austin, Texas.

Ueno et al., "A Capacitive Sensor System for Measuring Laplacian Electromyogram through Cloth: A Pilot Study", Proceedings of the 29th Annual International Conference of the IEEE EMBS, Cite Internationale, Lyon, France, Aug. 23-26, 2007.

Ueno et al., "Feasibility of Capacitive Sensing of Surface Electromyographic Potential through Cloth", Sensors and Materials 24(6):335-346, 2012.

Xiong et al., "A Novel HCI based on EMG and IMU", Proceedings of the 2011 IEEE International Conference on Robotics and Biomimetics, Phuket, Thailand, Dec. 7-11, 2011, 5 pages.

Zhang et al., "A Framework for Hand Gesture Recognition Based on Accelerometer and EMG Sensors", IEEE Transactions on Systems, Man, and Cybernetics—Part A: Systems and Humans, vol. 41, No. 6, pp. 1064-1076, Nov. 2011.

Non-Final Office Action received for U.S. Appl. No. 14/505,836 dated Jun. 30, 2016, 37 pages.

Xu et al., "Hand Gesture Recognition and Virtual Game Control Based on 3D Accelerometer and EMG Sensors", Proceedings of the 14th international conference on Intelligent user interfaces, Sanibel Island, Florida, Feb. 8-11, 2009, pp. 401-406.

Communication pursuant to Rule 164(1) EPC, dated Sep. 30, 2016, for corresponding EP Application No. 14753949.8, 7 pages.

Non-Final Office Action received for U.S. Appl. No. 14/505,836 dated Feb. 23, 2017, 54 pages.

Brownlee, "Finite State Machines (FSM): Finite state machines as a control technique in Artificial Intelligence (AI)", Jun. 2002, 12 pages.

International Search Report and Written Opinion for International Application No. PCT/US2019/015180 dated May 16, 2019.

Extended European Search Report received for EP Patent Application Serial No. 17835112.8 dated Feb. 5, 2020, 17 pages.

Extended European Search Report for European Application No. EP 17835111.0 dated Nov. 21, 2019.

Extended European Search Report for European Application No. EP 17835140.9 dated Nov. 26, 2019.

International Preliminary Report on Patentability received for PCT Application Serial No. PCT/US2014/017799 dated Sep. 3, 2015, 8 pages.

International Preliminary Report on Patentability received for PCT Application Serial No. PCT/US2014/037863 dated Nov. 26, 2015, 8 pages.

International Preliminary Report on Patentability received for PCT Application Serial No. PCT/US2014/052143 dated Mar. 3, 2016, 7 pages.

International Preliminary Report on Patentability received for PCT Application Serial No. PCT/US2014/067443 dated Jun. 9, 2016, 7 pages.

International Preliminary Report on Patentability received for PCT Application Serial No. PCT/US2015/015675 dated Aug. 25, 2016, 8 pages.

International Search Report and Written Opinion received for PCT Application Serial No. PCT/US2019/049094 dated Jan. 9, 2020, 27 pages.

Corazza et al., "A Markerless Motion Capture System to Study Musculoskeletal Biomechanics: Visual Hull and Simulated Annealing Approach", Annals of Biomedical Engineering, vol. 34, No. 6, Jul. 2006, pp. 1019-1029.

Non-Final Office Action received for U.S. Appl. No. 15/882,858 dated Oct. 30, 2019, 22 pages.

Non-Final Office Action received for U.S. Appl. No. 15/659,072 dated Apr. 30, 2019, 99 pages.

Final Office Action received for U.S. Appl. No. 15/659,072 dated Nov. 29, 2019, 36 pages.

Non-Final Office Action received for U.S. Appl. No. 16/353,998 dated May 24, 2019, 20 pages.

Final Office Action received for U.S. Appl. No. 16/353,998 dated Nov. 29, 2019, 33 pages.

International Search Report and Written Opinion for International Application No. PCT/US2019/052131 dated Dec. 6, 2019.

Al-Mashhadany, Inverse Kinematics Problem (IKP) of 6-DOF Manipulator Bgy Locally Recurrent Neural Networks (LRNNs). Management and Service Science (MASS). 2010 International Conference ON, IEEE. Aug. 24, 2010. 5 pages. ISBN: 978-1-4244-5325-2.

Marcard et al., Sparse Inertial Poser: Automatic 3D Human Pose Estimation from Sparse IMUs. Eurographics. 2017;36(2). 12 pages.

Wittevrongel et al., Spatiotemporal Beamforming: A Transparent and Unified Decoding Approach to Synchronous Visual Brain-Computer Interfacing. Frontiers in Neuroscience. 2017;11:1-12.

Zacharaki et al., Spike pattern recognition by supervised classification in low dimensional embedding space. Brain Informatics. 2016;3:73-8. DOI: 10.1007/s40708-016-0044-4.

Non-Final Office Action received for U.S. Appl. No. 16/557,342 dated Oct. 22, 2019, 16 pages.

Final Office Action received for U.S. Appl. No. 16/557,342 dated Jan. 28, 2020, 15 pages.

Non-Final Office Action received for U.S. Appl. No. 16/557,383 dated Dec. 23, 2019, 53 pages.

Non-Final Office Action received for U.S. Appl. No. 15/816,435 dated Jan. 22, 2020, 35 pages.

Non-Final Office Action received for U.S. Appl. No. 16/577,207 dated Nov. 19, 2019, 32 pages.

U.S. Appl. No. 14/505,836, filed Oct. 3, 2014.
U.S. Appl. No. 15/974,430, filed May 8, 2018.
U.S. Appl. No. 15/659,072, filed Jul. 25, 2017.
U.S. Appl. No. 15/816,435, filed Nov. 17, 2017.
U.S. Appl. No. 15/882,858, filed Jan. 29, 2018.
U.S. Appl. No. 16/353,998, filed Mar. 14, 2019.
U.S. Appl. No. 16/557,342, filed Aug. 30, 2019.
U.S. Appl. No. 16/557,383, filed Aug. 30, 2019.
U.S. Appl. No. 16/577,207, filed Sep. 20, 2019.

Final Office Action received for U.S. Appl. No. 15/882,858 dated Jun. 2, 2020, 127 pages.

Non-Final Office Action received for U.S. Appl. No. 15/659,072 dated Jun. 5, 2020, 59 pages.

(56) References Cited

OTHER PUBLICATIONS

Non-Final Office Action received for U.S. Appl. No. 16/353,998 dated May 26, 2020, 60 pages.
Non-Final Office Action received for U.S. Appl. No. 15/974,430 dated Apr. 30, 2020, 57 pages.
Final Office Action received for U.S. Appl. No. 16/557,383 dated Jun. 2, 2020, 66 pages.
Preinterview First Office Action received for U.S. Appl. No. 16/785,680 dated Jun. 24, 2020, 90 pages.
Non-Final Office Action received for U.S. Appl. No. 16/557,342 dated Jun. 15, 2020, 46 pages.

* cited by examiner

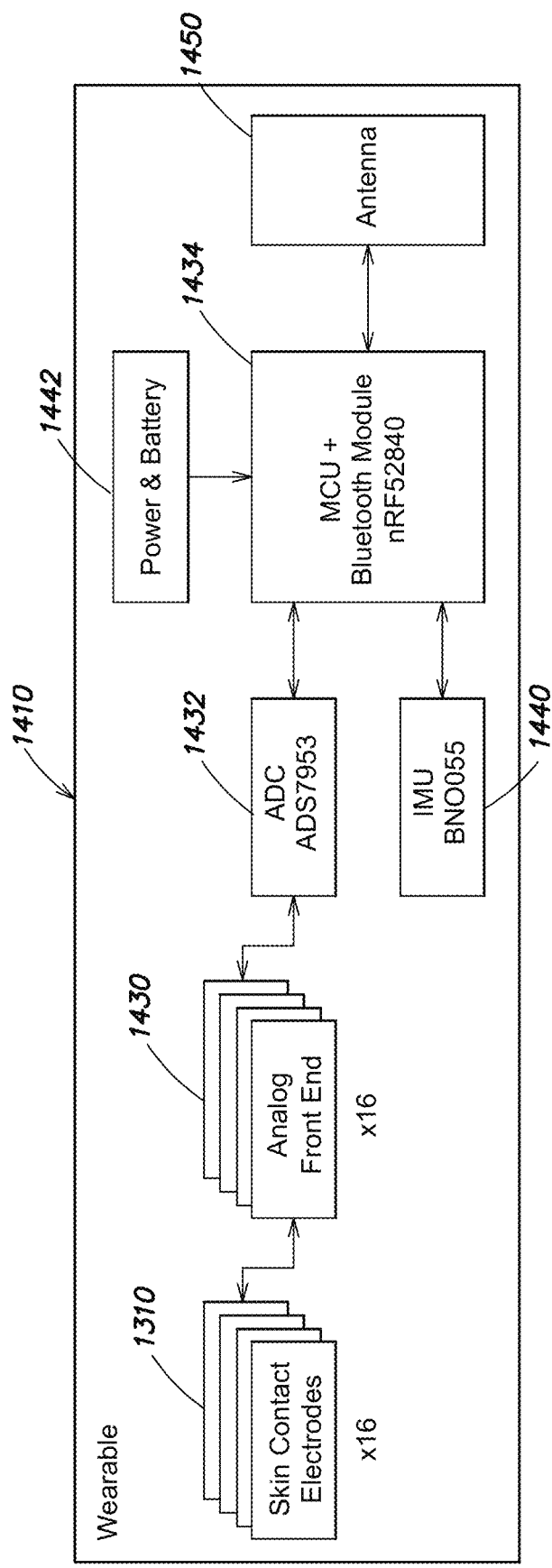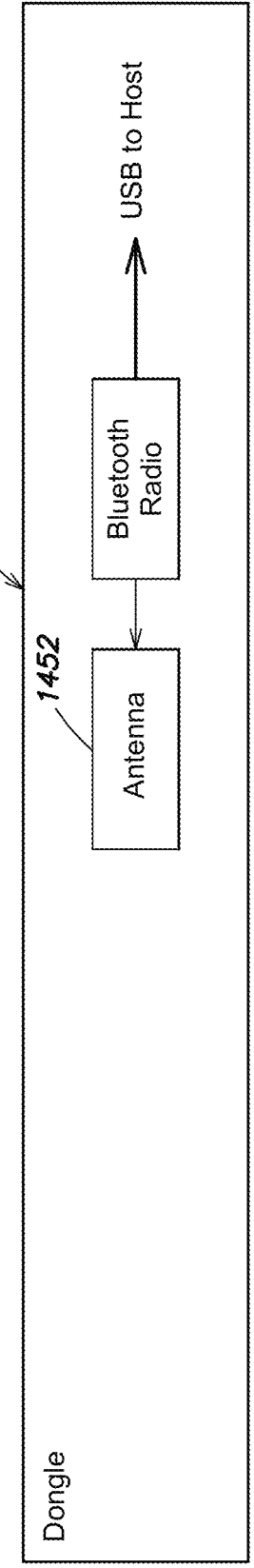
FIG. 14A
FIG. 14B

CAMERA-GUIDED INTERPRETATION OF NEUROMUSCULAR SIGNALS

CROSS-REFERENCE TO RELATED APPLICATIONS

This application claims the benefit under 35 U.S.C. § 119(e) of U.S. Provisional Patent Application Ser. No. 62/726,159, filed Aug. 31, 2018, entitled "CAMERA-GUIDED INTERPRETATION OF NEUROMUSCULAR SIGNALS", the entire contents of which are incorporated by reference herein.

FIELD OF THE INVENTION

The present technology relates to systems and methods that detect and interpret neuromuscular signals for use in performing functions in an augmented reality environment or a virtual reality environment, and that calibrate models used to interpret neuromuscular signals.

BACKGROUND

In some computer applications that generate musculoskeletal representations of a human body, it is desirable for the application to know the spatial positioning, orientation, and movement of a user's body to provide a realistic representation of body movement. For example, in an augmented reality (AR) environment or a virtual reality (VR) environment, tracking the spatial position of the user's hand enables the application to represent hand motion in the AR or VR environment, which allows the user to interact with (e.g., by grasping or manipulating) virtual objects within the AR or VR environment. Techniques have been developed for tracking movements of a user's body using wearable sensors, such as Inertial Measurement Units (IMUs), affixed to different parts of the user's body, to obtain position information and/or orientation information about the different parts of the user's body.

SUMMARY

According aspects of the technology described herein, a computerized system for using camera information to calibrate one or more inference models used to generate a musculoskeletal representation is provided. The system may comprise at least one camera configured to capture at least one image; a plurality of neuromuscular sensors configured to sense and record a plurality of neuromuscular signals from a user, wherein the plurality of neuromuscular sensors are arranged on one or more wearable devices structured to be worn by the user to obtain the plurality of neuromuscular signals; and at least one computer processor. The at least one processor may be programmed to calibrate one or more inference models by updating at least one parameter associated with the one or more inference models based, at least in part, on the plurality of neuromuscular signals and the at least one image.

In an aspect, the updating of the at least one parameter may include any one or any combination of: an updating of a routine for pre-processing the plurality of neuromuscular signals to calibrate the one or more inference models; an updating of a routine for pre-processing an image signal corresponding to the at least one image before the image signal is used to calibrate the one or more inference models; an updating of an architecture or architectures of the one or more inference models; an updating of a routine for post-processing an output of the one or more inference models; an updating of a selection routine for selecting the one or more inference models from a plurality of inference models; and an updating of a weight used for at least one of the one or more inference models.

In another aspect, the one or more inference models may be usable to generate a representation of any one or any combination of: a handstate, a still pose, and a dynamic gesture.

In an aspect, the at least one camera may comprise a camera disposed at a fixed location relative to the user.

In an aspect, the at least one camera may comprise a camera configured to be mounted on the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the updating of the at least one parameter associated with the one or more inference models may comprise training the one or more inference models to produce an output that is determined based, at least in part, on the at least one image when the plurality of neuromuscular signals or information derived from the plurality of neuromuscular signals, or both the plurality of neuromuscular signals and the information derived from the plurality of neuromuscular signals, is or are provided as input to the one or more inference models.

In an aspect, the computerized system may further comprise an extended reality (XR) system that generates an XR environment and displays a visual representation. The at least one computer processor may be further programmed to: detect, based at least in part on the at least one image, whether a gesture performed by the user matches a particular gesture; and, if the gesture performed by the user is detected to match the particular gesture, update the one or more inference models to incorporate neuromuscular data corresponding to the gesture performed by the user.

In a variation of this aspect, the at least one camera may comprise a camera attached to a head-mounted-display of the XR system.

In another variation of this aspect, the at least one computer processor may be further programmed to instruct the XR system to provide a visible prompt for the user to perform the particular gesture.

In another variation of this aspect, the at least one computer processor may be further programmed to instruct the XR system to provide an audible prompt for the user to perform the particular gesture.

In another variation of this aspect, the gesture may be performed by the user upon an instruction from an external source.

In another variation of this aspect, the gesture performed by the user may be detected to match the particular gesture when a similarity between the gesture performed by the user and the particular gesture is above a predetermined threshold.

In another variation of this aspect, the visual representation may be displayed on a display screen viewable by the user, and may comprise a visual representation of a hand.

In another variation of this aspect, the visual representation may be displayed on a display screen viewable by the user, and may comprise instructions to the user.

In another variation of this aspect, the prompt for the user to perform the particular gesture may be a visual representation of the particular gesture provided on a display screen viewable by the user.

In various variations of this aspect, the visual representation may be within the XR environment.

In a variation of this aspect, the particular gesture may be one of: a motion or dynamic gesture, and a pose or static gesture.

In a variation of this aspect, the at least one image may be captured by the at least one camera during performance of the gesture by the user, and the at least one computer processor may be further programmed to cause feedback to be provided to the user based, at least in part, on the at least one image captured during the performance of the gesture by the user. In one example, the feedback to be provided to the user may indicate whether a body part of the user necessary for the particular gesture to be performed is fully included in the at least one image captured during the performance of the gesture by the user. In another example, the feedback to be provided to the user may indicate whether a body part of the user necessary for the particular gesture to be performed is fully or partially occluded in the at least one image captured during the performance of the gesture by the user. In another example, the at least one computer processor may instruct the XR system to provide the feedback within the XR environment. In another example, the feedback may comprise one or more of: audible feedback, visible feedback, haptic feedback, and electrical stimulation feedback. For instance, the visible feedback may be a moving image or a still image showing a way to perform the particular gesture.

In an aspect, the at least one computer processor may be further programmed to determine whether the at least one image includes position information for at least two segments of a musculoskeletal representation. The updating of the at least one parameter associated with the one or more inference models may comprise updating the one or more inference models to incorporate neuromuscular data corresponding to the plurality of neuromuscular signals, when it is determined that the at least one image includes position information for at least two segments of the musculoskeletal representation.

In an aspect, the at least one computer processor may be further programmed to: detect based, at least in part, on the at least one image, whether a gesture performed by the user to perform a task within an extended reality (XR) environment generated by an XR system matches a stored gesture for performing the task; and, if the gesture performed by the user matches the stored gesture for performing the task, update the one or more inference models to incorporate neuromuscular data corresponding to the gesture performed by the user.

In a variation of this aspect, the gesture performed by the user may be detected to match the stored gesture when a similarity between the gesture performed by the user and the stored gesture is above a predetermined threshold.

In another variation of this aspect, the one or more inference models may be usable to generate a representation of any one or any combination of: a handstate, a still pose, and a dynamic gesture.

In an aspect, the at least one computer processor may be further programmed to determine, based on the at least one image, a user-specific skeletal geometry corresponding to the user. The updating of the at least one parameter associated with the one or more inference models may comprise updating the at least one parameter of the one or more inference models based on the determined user-specific skeletal geometry.

In a variation of this aspect, the user-specific skeletal geometry may comprise a length of at least one finger of the user.

In an aspect, the at least one camera may be configured to capture a plurality of images in a time series. The updating of the at least one parameter of the one or more inference models may be further based, at least in part, on the plurality of images captured in a time series.

According aspects of the technology described herein, a method of a computerized system for using camera information to calibrate one or more inference models used to generate a musculoskeletal representation is provided. The method may comprise: receiving, by at least one computer processor, one or both of: at least one image captured by at least one camera and information derived from the at least one image; receiving, by the at least one computer processor, one or both of: a plurality of neuromuscular signals from a user and information derived from the plurality of neuromuscular signals, the plurality of neuromuscular signals being sensed and recorded by plurality of neuromuscular sensors arranged on one or more wearable devices worn by the user; and calibrating, by the at least one processor, one or more inference models by updating at least one parameter associated with the one or more inference models based, at least in part, on the plurality of neuromuscular signals and the at least one image.

In an aspect, the updating of the at least one parameter may include any one or any combination of: an updating of a routine for pre-processing the plurality of neuromuscular signals to calibrate the one or more inference models; an updating of a routine for pre-processing an image signal corresponding to the at least one image before the image signal is used to calibrate the one or more inference models; an updating of an architecture or architectures of the one or more inference models; an updating of a routine for post-processing an output of the one or more inference models; an updating of a selection routine for selecting the one or more inference models from a plurality of inference models; and an updating of a weight used for at least one of the one or more inference models.

In an aspect, the one or more inference models may be usable to generate a representation of any one or any combination of: a handstate, a still pose, and a dynamic gesture.

In an aspect, the at least one camera may comprise a camera disposed at a fixed location relative to the user.

In an aspect, the at least one camera may comprise a camera configured to be mounted on the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the updating of the at least one parameter associated with the one or more inference models may comprise training the one or more inference models to produce an output that is determined based, at least in part, on the at least one image when the plurality of neuromuscular signals or information derived from the plurality of neuromuscular signals, or both the plurality of neuromuscular signals and the information derived from the plurality of neuromuscular signals, is or are provided as input to the one or more inference models.

In an aspect, the method may further comprise: detecting, by the at least one processor, based at least in part on the at least one image, whether a gesture performed by the user matches a particular gesture; and, if the gesture performed by the user is detected to match the particular gesture, updating the one or more inference models to incorporate neuromuscular data corresponding to the gesture performed by the user. The at least one processor may be in communication with an extended reality (XR) system that generates an XR environment and displays a visual representation.

In a variation of this aspect, the at least one camera may comprise a camera attached to a head-mounted-display of the XR system.

In another variation of this aspect, the method may further comprise instructing, by the at last one processor, the XR system to provide a visible prompt for the user to perform the particular gesture.

In another variation of this aspect, the method may further comprise instructing, by the at least one processor, the XR system to provide an audible prompt for the user to perform the particular gesture.

In a variation of some of the aspects, the gesture may be performed by the user upon an instruction from an external source.

In a variation of some of the aspects, the gesture performed by the user may be detected to match the particular gesture when a similarity between the gesture performed by the user and the particular gesture is above a predetermined threshold.

In a variation of some of the aspects, the visual representation may be displayed on a display screen viewable by the user, and may comprise a visual representation of a hand.

In a variation of some of the aspects, the visual representation may be displayed on a display screen viewable by the user, and may comprise instructions to the user.

In a variation of some of the aspects, the prompt for the user to perform the particular gesture may be a visual representation of the particular gesture provided on a display screen viewable by the user.

In a variation of some of the aspects, the visual representation may be within the XR environment.

In a variation of some of the aspects, the particular gesture may be one of: a motion or dynamic gesture, and a pose or static gesture.

In a variation of some of the aspects, the at least one image may be captured by the at least one camera during performance of the gesture by the user. The method may further comprise the at least one processor causing feedback to be provided to the user based, at least in part, on the at least one image captured during the performance of the gesture by the user.

In a variation of some of the aspects, the feedback to be provided to the user may indicate whether a body part of the user necessary for the particular gesture to be performed is fully included in the at least one image captured during the performance of the gesture by the user.

In a variation of some of the aspects, the feedback to be provided to the user may indicate whether a body part of the user necessary for the particular gesture to be performed is fully or partially occluded in the at least one image captured during the performance of the gesture by the user.

In a variation of some of the aspects, the at least one computer processor may cause the XR system to provide the feedback within the XR environment.

In a variation of some of the aspects, the feedback may comprise one or more of: audible feedback, visible feedback, haptic feedback, and electrical stimulation feedback.

In a further variation, the visible feedback may be a moving image or a still image showing a way to perform the particular gesture.

In an aspect, the method may further comprise determining, by the at least one computer processor, whether the at least one image includes position information for at least two segments of a musculoskeletal representation. The updating of the at least one parameter associated with the one or more inference models may comprise updating the one or more inference models to incorporate neuromuscular data corresponding to the plurality of neuromuscular signals, when it is determined that the at least one image includes position information for at least two segments of the musculoskeletal representation.

In an aspect, the method may further comprise: detecting, by the at least one processor, based at least in part on the at least one image, whether a gesture performed by the user to perform a task within an extended reality (XR) environment generated by an XR system matches a stored gesture for performing the task; and, if the gesture performed by the user matches the stored gesture for performing the task, updating, by the at least one processor, the one or more inference models to incorporate neuromuscular data corresponding to the gesture performed by the user.

In a variation of this aspect, the gesture performed by the user may be detected to match the stored gesture when a similarity between the gesture performed by the user and the stored gesture is above a predetermined threshold.

In another variation of this aspect, the one or more inference models may be usable to generate a representation of any one or any combination of: a handstate, a still pose, and a dynamic gesture.

In an aspect, the method may further comprise: determining, by the at least one computer processor, based on the at least one image, a user-specific skeletal geometry corresponding to the user. The updating of the at least one parameter associated with the one or more inference models may comprise updating the at least one parameter of the one or more inference models based on the determined user-specific skeletal geometry.

In a variation of this aspect, the user-specific skeletal geometry may comprise a length of at least one finger of the user.

In an aspect, the at least one camera may be configured to capture a plurality of images in a time series. The updating of the at least one parameter of the one or more inference models may be further based, at least in part, on the plurality of images captured in a time series.

According aspects of the technology described herein, a non-transitory computer-readable storage medium storing code that, when executed by at least one computer, causes the at least one computer to perform a method for using camera information to calibrate one or more inference models used to generate a musculoskeletal representation is provided. The method may comprise: receiving one or both of: at least one image captured by at least one camera and information derived from the at least one image; receiving one or both of: a plurality of neuromuscular signals from a user and information derived from the plurality of neuromuscular signals, the plurality of neuromuscular signals being sensed and recorded by plurality of neuromuscular sensors arranged on one or more wearable devices worn by the user; and calibrating one or more inference models by updating at least one parameter associated with the one or more inference models based, at least in part, on the plurality of neuromuscular signals and the at least one image.

In an aspect, the updating of the at least one parameter includes any one or any combination of: an updating of a routine for pre-processing the plurality of neuromuscular signals to calibrate the one or more inference models, an updating of a routine for pre-processing an image signal corresponding to the at least one image before the image signal is used to calibrate the one or more inference models, an updating of an architecture or architectures of the one or more inference models, an updating of a routine for post-processing an output of the one or more inference models, an updating of a selection routine for selecting the one or more inference models from a plurality of inference models, and an updating of a weight used for at least one of the one or more inference models.

In an aspect, the one or more inference models may be usable to generate a representation of any one or any combination of: a handstate, a still pose, and a dynamic gesture.

In an aspect, the at least one camera may comprise a camera disposed at a fixed location relative to the user.

In an aspect, the at least one camera may comprise a camera configured to be mounted on the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the updating of the at least one parameter associated with the one or more inference models may comprise training the one or more inference models to produce an output that is determined based, at least in part, on the at least one image when the plurality of neuromuscular signals or information derived from the plurality of neuromuscular signals, or both the plurality of neuromuscular signals and the information derived from the plurality of neuromuscular signals, is or are provided as input to the one or more inference models.

In an aspect, the at least one computer may be in communication with an extended reality (XR) system that generates an XR environment and displays a visual representation. The method may further comprise: detecting, based at least in part on the at least one image, whether a gesture performed by the user matches a particular gesture; and, if the gesture performed by the user is detected to match the particular gesture, updating the one or more inference models to incorporate neuromuscular data corresponding to the gesture performed by the user.

In a variation of this aspect, the at least one camera may comprise a camera attached to a head-mounted-display of the XR system.

In another variation of this aspect, the method may further comprise instructing the XR system to provide a visible prompt for the user to perform the particular gesture.

In another variation of this aspect, the method may further comprise instructing the XR system to provide an audible prompt for the user to perform the particular gesture.

In another variation of this aspect, the gesture may be performed by the user upon an instruction from an external source.

In another variation of this aspect, the gesture performed by the user may be detected to match the particular gesture when a similarity between the gesture performed by the user and the particular gesture is above a predetermined threshold.

In another variation of this aspect, the visual representation may be displayed on a display screen viewable by the user, and may comprise a visual representation of a hand.

In another variation of this aspect, the visual representation may be displayed on a display screen viewable by the user, and may comprise instructions to the user.

In another variation of this aspect, the prompt for the user to perform the particular gesture may be a visual representation of the particular gesture provided on a display screen viewable by the user.

In a variation of some of the aspects, the visual representation may be within the XR environment.

In a variation of some of the aspects, the particular gesture may be one of: a motion or dynamic gesture, and a pose or static gesture.

In a variation of some of the aspects, the at least one image may be captured by the at least one camera during performance of the gesture by the user. The method may further comprise causing feedback to be provided to the user based, at least in part, on the at least one image captured during the performance of the gesture by the user.

In a variation of some of the aspects, the feedback to be provided to the user may indicate whether a body part of the user necessary for the particular gesture to be performed is fully included in the at least one image captured during the performance of the gesture by the user.

In a variation of some of the aspects, the feedback to be provided to the user may indicate whether a body part of the user necessary for the particular gesture to be performed is fully or partially occluded in the at least one image captured during the performance of the gesture by the user.

In a variation of some of the aspects, the feedback may be caused to be provided within the XR environment.

In a variation of some of the aspects, the feedback may comprise one or more of: audible feedback, visible feedback, haptic feedback, and electrical stimulation feedback. In a further variation, the visible feedback may be a moving image or a still image showing a way to perform the particular gesture.

In an aspect, the method may further comprise determining whether the at least one image includes position information for at least two segments of a musculoskeletal representation. The updating of the at least one parameter associated with the one or more inference models may comprise updating the one or more inference models to incorporate neuromuscular data corresponding to the plurality of neuromuscular signals, when it is determined that the at least one image includes position information for at least two segments of the musculo skeletal representation.

In an aspect, the method may further comprise: detecting based at least in part on the at least one image, whether a gesture performed by the user to perform a task within an extended reality (XR) environment generated by an XR system matches a stored gesture for performing the task; and, if the gesture performed by the user matches the stored gesture for performing the task, updating, by the at least one processor, the one or more inference models to incorporate neuromuscular data corresponding to the gesture performed by the user.

In a variation of the aspect, the gesture performed by the user may be detected to match the stored gesture when a similarity between the gesture performed by the user and the stored gesture is above a predetermined threshold.

In a variation of the some of the aspects, the one or more inference models may be usable to generate a representation of any one or any combination of: a handstate, a still pose, and a dynamic gesture.

In an aspect, the method may further comprise determining, based on the at least one image, a user-specific skeletal geometry corresponding to the user. The updating of the at least one parameter associated with the one or more inference models may comprise updating the at least one parameter of the one or more inference models based on the determined user-specific skeletal geometry.

In a variation of this aspect, the user-specific skeletal geometry may comprise a length of at least one finger of the user.

In an aspect, the at least one camera may be configured to capture a plurality of images in a time series. The updating of the at least one parameter of the one or more inference models may be further based, at least in part, on the plurality of images captured in a time series.

According aspects of the technology described herein, a computerized system for providing dynamically-updated musculoskeletal information is provided. The system may comprise: at least one camera configured to capture at least one image; a plurality of neuromuscular sensors configured to sense and record a plurality of neuromuscular signals from a user, wherein the plurality of neuromuscular sensors are arranged on one or more wearable devices structured to be worn by the user to obtain the plurality of neuromuscular signals; and at least one computer processor. The at least one processor may be programmed to: provide, as an input to a trained inference model, information based on the plurality of neuromuscular signals and information based on the at least one image; determine, based on an output of the trained inference model, position information describing a spatial relationship between two or more connected musculoskeletal segments of the user, or force information describing a force exerted by at least one musculoskeletal segment of the user, or both the position information and the force information; and output the position information, or the force information, or both the position information and the force information.

In an aspect, the position information may be musculoskeletal position information that may include any one or any combination of: a handstate, a likelihood of a handstate, a still pose, a likelihood of a still pose, a dynamic gesture, and a likelihood of a dynamic gesture.

In an aspect, the at least one computer processor may be further programmed to: determine a first quality of the plurality of neuromuscular signals, or a second quality of the at least one image, or both the first quality and the second quality, and weight the plurality of neuromuscular signals, or the at least one image, or both the plurality of neuromuscular signals and the at least one image based on one or both of the first quality and the second quality, to determine the information based on the plurality of neuromuscular signals and the at least one image.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the at least one computer processor may be further programmed to determine the first quality in response to a determination that the second quality is greater than a threshold value.

In an aspect, the two or more connected musculoskeletal segments may include a forearm rigid segment connected via a wrist joint to a plurality of rigid segments for a hand. The plurality of neuromuscular sensors may include a plurality of electromyography (EMG) sensors. The at least one computer processor may be further programmed to: determine the position information for the plurality of rigid segments in the hand based, at least in part, on the plurality of neuromuscular signals output from the plurality of EMG sensors; and determine the position information for the forearm rigid segment based, at least in part, on the at least one image captured by the at least one camera.

In an aspect, a wrist of the user, a hand connected to the wrist, and fingers of the hand may be captured by the at least one image. The two or more connected musculoskeletal segments may include the wrist, the hand, and the fingers of the user. The at least one computer processor may be programmed to determine at least one of the position information and the force information for the plurality of rigid segments in the hand based, at least in part, on the plurality of neuromuscular signals and the at least one image captured by the at least one camera.

In a variation of this aspect, the at least one camera may capture the at least one image while the plurality of neuromuscular signals are sensed and recorded. The one or more wearable devices may be worn on a wrist of the user or a forearm of the user when the plurality of neuromuscular signals are sensed and recorded. The at least one computer processor may be programmed to determine any one or any combination of: a handstate, a dynamic gesture, and a still pose of the user based, at least in part, on the plurality of neuromuscular signals and the at least one image captured by the at least one camera.

In a variation of some of the aspects, the computerized system may further comprise at least one inertial measurement unit (IMU) sensor. The at least one computer processor may be further programmed to determine the position information for the forearm rigid segment further based, at least in part, on IMU signals output from the at least one IMU sensor. In a further variation, the at least one computer processor may be programmed to: determine an initial position of the forearm rigid segment based, at least in part, on the IMU signals output from the at least one IMU sensor; and adjust the initial position information for the forearm rigid segment based, at least in part, on the at least one image captured by the at least one camera.

In an aspect, the one or more wearable devices may include at least one positional marker included thereon. The position information may be determined based, at least in part, on the at least one positional marker captured in the at least one image.

In an aspect, the trained inference model may be trained: to determine the position information based, at least in part, on the at least one image; and to determine the force information based on the plurality of neuromuscular signals.

In a variation of this aspect, the trained inference model may be trained to determine the position information based only on the at least one image.

In another variation of this aspect, the trained inference model may determine the position information by determining, based on the at least one image, that at least two of the connected musculoskeletal segments of the user are touching. The trained inference model may determine the force information by determining, based on the plurality of neuromuscular signals, a force applied between the at least two of the connected musculoskeletal segments of the user that are touching.

In various further variations, the at least two of the connected musculoskeletal segments of the user may comprise a thumb of the user and at least one other finger of the user. The trained inference model may determine, based on the at least one image, that the thumb of the user and the at least one other finger of the user are touching. The trained inference model may determine a force applied between the thumb of the user and the at least one other finger of the user. The trained inference model may further determine, based on the at least one image, that tips of the thumb of the user and the at least one other finger of the user are touching.

In an aspect, the at least one computer processor may be further programmed to: determine, based on the at least one image, a position of a hand of the user relative to a physical object or a virtual object; and determine the position information, or the force information, or both the position information and the force information based, at least in part, on the position of the hand of the user relative to the physical object or the virtual object.

In a variation of this aspect, the at least one computer processor may be programmed to: determine from the at least one image that the user is grasping the physical object or the virtual object; and determine the force information solely based on the plurality of neuromuscular signals.

In another variation of this aspect, the physical object may have a pliable surface. The at least one computer processor may be programmed to: determine the user is grasping the physical object based on a deformation in the pliable surface captured in the at least one image; and determine the force information based on one or both of: the plurality of neuromuscular signals and the deformation in the pliable surface captured in the at least one image.

In a variation of some of the aspects, the at least one image may include any one or any combination of: an image produced by visible light, an image produced by infrared light, an image produced by light of a predetermined range of wavelengths, and an image produced by light of two or more different predetermined ranges of wavelengths.

In a variation of some of the aspects, the information based on the plurality of neuromuscular signals may comprise one or both of: the plurality of neuromuscular signals and information derived from the plurality of neuromuscular signals.

In a variation of some of the aspects, the information based on the at least one image may comprise one or both of: an image signal of the at least one image and information derived from the image signal of the at least one image.

In a variation of some of the aspects, the physical object may be a surface. The at least one computer processor may be further programmed to determine the force information based, at least in part, on a position of at least a portion of the hand relative to the surface.

In a variation of some of the aspects, wherein the virtual object may be a virtual object displayed in an extended reality (XR) environment generated by an XR system. The at least one computer processor may be further programmed to determine the position information based on whether the hand of the user is touching the virtual object in the XR environment.

According aspects of the technology described herein, a method of a computerized system for providing dynamically-updated musculoskeletal information is provided. The method may comprise: receiving, by at least one processor, at least one image captured by at least one camera; receiving, by the at least one processor, a plurality of neuromuscular signals sensed and recorded by a plurality of neuromuscular sensors configured to sense and record a plurality of neuromuscular signals from a user, wherein the plurality of neuromuscular sensors are arranged on one or more wearable devices structured to be worn by the user to obtain the plurality of neuromuscular signals; providing, by the at least one processor, as an input to a trained inference model, information based on the plurality of neuromuscular signals and information based on the at least one image; determining, by the at least one processor, based on an output of the trained inference model, position information describing a spatial relationship between two or more connected musculoskeletal segments of the user, or force information describing a force exerted by at least one musculoskeletal segment of the user, or both the position information and the force information; and outputting, by the at least one processor, the position information, or the force information, or both the position information and the force information.

In an aspect, the position information may be musculoskeletal position information that includes any one or any combination of: a handstate, a likelihood of a handstate, a still pose, a likelihood of a still pose, a dynamic gesture, and a likelihood of a dynamic gesture.

In an aspect, the method may further comprise: determining, by the at least one processor, a first quality of the plurality of neuromuscular signals, or a second quality of the at least one image, or both the first quality and the second quality; and weighting, by the at least one processor, the plurality of neuromuscular signals, or the at least one image, or both the plurality of neuromuscular signals and the at least one image based on one or both of the first quality and the second quality, to determine the information based on the plurality of neuromuscular signals and the at least one image.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the method may further comprise determining, by the at least one processor, the first quality in response to a determination that the second quality is greater than a threshold value.

In an aspect, the two or more connected musculoskeletal segments may include a forearm rigid segment connected via a wrist joint to a plurality of rigid segments for a hand. The plurality of neuromuscular sensors may include a plurality of electromyography (EMG) sensors. The method may further comprise: determining, by the at least one processor, the position information for the plurality of rigid segments in the hand based, at least in part, on the plurality of neuromuscular signals output from the plurality of EMG sensors; and determining the position information for the forearm rigid segment based, at least in part, on the at least one image captured by the at least one camera.

In an aspect, a wrist of the user, a hand connected to the wrist, and fingers of the hand may be captured by the at least one image. The two or more connected musculoskeletal segments may include the wrist, the hand, and the fingers of the user. The method may further comprise determining, by the at least one processor, at least one of the position information and the force information for the plurality of rigid segments in the hand based, at least in part, on the plurality of neuromuscular signals and the at least one image captured by the at least one camera.

In a variation of this aspect, the at least one camera may capture the at least one image while the plurality of neuromuscular signals are sensed and recorded. The one or more wearable devices may be worn on a wrist of the user or a forearm of the user when the plurality of neuromuscular signals are sensed and recorded. The method may further comprise determining, by the at least one processor, any one or any combination of: a handstate, a dynamic gesture, and a still pose of the user based, at least in part, on the plurality of neuromuscular signals and the at least one image captured by the at least one camera.

In a variation of some of the aspect, the method may further comprise: receiving, by the at least one processor, inertial measurement unit (IMU) signals sensed and recorded by at least one IMU sensor; and determining, by the at least one processor, the position information for the forearm rigid segment further based, at least in part, on the IMU signals. In a further variation, the method may comprise: determining, by the at least one processor, an initial position of the forearm rigid segment based, at least in part, on the IMU signals; and adjusting the initial position information for the forearm rigid segment based, at least in part, on the at least one image captured by the at least one camera.

In an aspect, the one or more wearable devices may include at least one positional marker included thereon. The position information may be determined based, at least in part, on the at least one positional marker captured in the at least one image.

In an aspect, the trained inference model may be trained: to determine the position information based, at least in part, on the at least one image; and to determine the force information based on the plurality of neuromuscular signals.

In a variation of this aspect, the trained inference model may be trained to determine the position information based only on the at least one image.

In another variation of this aspect, the trained inference model may determine the position information by determining, based on the at least one image, that at least two of the connected musculoskeletal segments of the user are touching. The trained inference model may determine the force information by determining, based on the plurality of neuromuscular signals, a force applied between the at least two of the connected musculoskeletal segments of the user that are touching.

In a variation of some of the aspects, the at least two of the connected musculoskeletal segments of the user may comprise a thumb of the user and at least one other finger of the user. The trained inference model may determine, based on the at least one image, that the thumb of the user and the at least one other finger of the user are touching. The trained inference model may determine a force applied between the thumb of the user and the at least one other finger of the user. In a further variation, the trained inference model may determine, based on the at least one image, that tips of the thumb of the user and the at least one other finger of the user are touching.

In an aspect, the method may further comprise: determining, by the at least one processor based on the at least one image, a position of a hand of the user relative to a physical object or a virtual object; and determining, by the at least one processor, the position information, or the force information, or both the position information and the force information based, at least in part, on the position of the hand of the user relative to the physical object or the virtual object.

In a variation of this aspect, the method may further comprise: determining, by the at least one processor, based on the at least one image, that the user is grasping the physical object or the virtual object; and determining, by the at least one processor, the force information solely based on the plurality of neuromuscular signals.

In another variation of this aspect, the physical object may have a pliable surface. The method may further comprise: determining, by the at least one processor, whether the user is grasping the physical object based on a deformation in the pliable surface captured in the at least one image; and determining, by the at least one processor, the force information based on one or both of: the plurality of neuromuscular signals and the deformation in the pliable surface captured in the at least one image.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the information based on the plurality of neuromuscular signals may comprise one or both of: the plurality of neuromuscular signals and information derived from the plurality of neuromuscular signals.

In an aspect, the information based on the at least one image may comprise one or both of: an image signal of the at least one image and information derived from the image signal of the at least one image.

In a variation of some of the aspects, the physical object may be a surface. The method may further comprise: determining, by the at least one processor, the force information based, at least in part, on a position of at least a portion of the hand relative to the surface.

In a variation of some of the aspects, the virtual object may be a virtual object displayed in an extended reality (XR) environment generated by an XR system. The method may further comprise determining, by the at least one processor, the position information based on whether the hand of the user is touching the virtual object in the XR environment.

According aspects of the technology described herein, a non-transitory computer-readable storage medium storing code that, when executed by at least one computer, causes the at least one computer to perform a method for providing dynamically-updated musculoskeletal information is provided. The method may comprise: receiving at least one image captured by at least one camera; receiving a plurality of neuromuscular signals sensed and recorded by a plurality of neuromuscular sensors configured to sense and record a plurality of neuromuscular signals from a user, wherein the plurality of neuromuscular sensors are arranged on one or more wearable devices structured to be worn by the user to obtain the plurality of neuromuscular signals; providing, as an input to a trained inference model, information based on the plurality of neuromuscular signals and information based on the at least one image; determining, based on an output of the trained inference model, position information describing a spatial relationship between two or more connected musculoskeletal segments of the user, or force information describing a force exerted by at least one musculoskeletal segment of the user, or both the position information and the force information; and outputting the position information, or the force information, or both the position information and the force information.

In an aspect, the position information may be musculoskeletal position information that may include any one or any combination of: a handstate, a likelihood of a handstate, a still pose, a likelihood of a still pose, a dynamic gesture, and a likelihood of a dynamic gesture.

In an aspect, the method may further comprise: determining a first quality of the plurality of neuromuscular signals, or a second quality of the at least one image, or both the first quality and the second quality; and weighting the plurality of neuromuscular signals, or the at least one image, or both the plurality of neuromuscular signals and the at least one image based on one or both of the first quality and the second quality, to determine the information based on the plurality of neuromuscular signals and the at least one image.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the method may further comprise determining the first quality in response to a determination that the second quality is greater than a threshold value.

In an aspect, the two or more connected musculoskeletal segments may include a forearm rigid segment connected via a wrist joint to a plurality of rigid segments for a hand. The plurality of neuromuscular sensors may include a plurality of electromyography (EMG) sensors. The method may further comprise: determining the position information for the plurality of rigid segments in the hand based, at least in part, on the plurality of neuromuscular signals output from the plurality of EMG sensors; and determining the position information for the forearm rigid segment based, at least in part, on the at least one image captured by the at least one camera.

In an aspect, a wrist of the user, a hand connected to the wrist, and fingers of the hand may be captured by the at least one image. The two or more connected musculoskeletal segments may include the wrist, the hand, and the fingers of the user. The method may further comprise determining at least one of the position information and the force information for the plurality of rigid segments in the hand based, at least in part, on the plurality of neuromuscular signals and the at least one image captured by the at least one camera.

In a variation of this aspect, the at least one camera may capture the at least one image while the plurality of neuromuscular signals are sensed and recorded. The one or more wearable devices may be worn on a wrist of the user or a forearm of the user when the plurality of neuromuscular signals are sensed and recorded. The method may further comprise determining any one or any combination of: a handstate, a dynamic gesture, and a still pose of the user based, at least in part, on the plurality of neuromuscular signals and the at least one image captured by the at least one camera.

In a variation of some of the aspects, the method may further comprise: receiving inertial measurement unit (IMU) signals sensed and recorded by at least one IMU sensor; and determining the position information for the forearm rigid segment further based, at least in part, on the IMU signals. In a further variation, the method may comprise: determining an initial position of the forearm rigid segment based, at least in part, on the IMU signals; and adjusting the initial position information for the forearm rigid segment based, at least in part, on the at least one image captured by the at least one camera.

In an aspect, the one or more wearable devices may include at least one positional marker included thereon. The position information may be determined based, at least in part, on the at least one positional marker captured in the at least one image.

In an aspect, the trained inference model may be trained: to determine the position information based, at least in part, on the at least one image; and to determine the force information based on the plurality of neuromuscular signals.

In a variation of this aspect, the trained inference model may be trained to determine the position information based only on the at least one image.

In another variation of this aspect, the trained inference model may determine the position information by determining, based on the at least one image, that at least two of the connected musculoskeletal segments of the user are touching. The trained inference model may determine the force information by determining, based on the plurality of neuromuscular signals, a force applied between the at least two of the connected musculoskeletal segments of the user that are touching.

In a variation of some of the aspects, the at least two of the connected musculoskeletal segments of the user may comprise a thumb of the user and at least one other finger of the user. The trained inference model may determine, based on the at least one image, that the thumb of the user and the at least one other finger of the user are touching. The trained inference model may determine a force applied between the thumb of the user and the at least one other finger of the user. In a further variation, the trained inference model may determine, based on the at least one image, that tips of the thumb of the user and the at least one other finger of the user are touching.

In an aspect, the method may further comprise: determining, based on the at least one image, a position of a hand of the user relative to a physical object or a virtual object; and determining the position information, or the force information, or both the position information and the force information based, at least in part, on the position of the hand of the user relative to the physical object or the virtual object.

In a variation of this aspect, the method may further comprise: determining, based on the at least one image, that the user is grasping the physical object or the virtual object; and determining the force information solely based on the plurality of neuromuscular signals.

In another variation of this aspect, the physical object may have a pliable surface. The method may further comprise: determining whether the user is grasping the physical object based on a deformation in the pliable surface captured in the at least one image; and determining the force information based on one or both of: the plurality of neuromuscular signals and the deformation in the pliable surface captured in the at least one image.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the information based on the plurality of neuromuscular signals may comprise one or both of: the plurality of neuromuscular signals and information derived from the plurality of neuromuscular signals.

In an aspect, the information based on the at least one image may comprise one or both of: an image signal of the at least one image and information derived from the image signal of the at least one image.

In a variation of some of the aspects, the physical object may be a surface. The method may further comprise determining the force information based, at least in part, on a position of at least a portion of the hand relative to the surface.

In a variation of some of the aspects, the virtual object may be a virtual object displayed in an extended reality (XR) environment generated by an XR system. The method may further comprise determining the position information based on whether the hand of the user is touching the virtual object in the XR environment.

According aspects of the technology described herein, a computerized system for training an inference model used to generate a musculoskeletal representation is provided. The system may comprise a plurality of neuromuscular sensors configured to sense and record a plurality of neuromuscular signals from a user, wherein the plurality of neuromuscular sensors are arranged on one or more wearable devices structured to be worn by the user to obtain the plurality of neuromuscular signals; at least one camera configured to capture at least one image while the plurality of neuromuscular signals are sensed and recorded; and at least one computer processor. The at least one computer processor may be programmed to: determine, based on information obtained from the at least one image, position information describing a spatial relationship between two or more connected musculoskeletal segments of the user; determine, based on the plurality of neuromuscular signals, force information; associate the position information with the force information; train an inference model to output a musculoskeletal representation consistent with the position information, or the force information, or the position information and the force information when neuromuscular input signals provided to the inference model have at least one predetermined characteristic, to produce an updated inference model; and cause the updated inference model to be stored in a memory.

In an aspect, the at least one computer processor may determine the position information based on the information obtained from the at least one image and information obtained from the plurality of neuromuscular signals.

In an aspect, the at least one image may comprise a series of time-sequenced images forming a video.

In an aspect, the musculoskeletal representation may correspond to any one or any combination of: a handstate of the user, a still pose of the user, and a dynamic gesture of the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the at least one computer processor may be programmed to: determine a first quality of the plurality of neuromuscular signals, or a second quality of the at least one image, or both the first quality and the second quality; and weight the plurality of neuromuscular signals, or the at least one image, or both the plurality of neuromuscular signals and the at least one image based on one or both of the first quality and the second quality, to train the inference model.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the at least one computer processor may be further programmed to determine the first quality in response to a determination that the second quality is greater than a threshold value.

In an aspect, the at least one predetermined characteristic may comprise any one or any combination of: a presence of an artifact of the neuromuscular input signals, a presence of a plurality of artifacts of the neuromuscular input signals, a relative position of a plurality of artifacts of the neuromuscular input signals, a range of amplitudes of the neuromuscular input signals, and a periodic frequency of artifacts of the neuromuscular input signals.

In an aspect, the computerized system may further comprise at least one inertial measurement unit (IMU) sensor. The at least one computer processor may be further programmed to determine the position information based, at least in part, on IMU signals output from the at least one IMU sensor.

In an aspect, the one or more wearable devices may include at least one positional marker included thereon. The position information may be determined based, at least in part, on the at least one positional marker captured in the at least one image.

According aspects of the technology described herein, method of a computerized system for training an inference model used to generate a musculoskeletal representation is provided. The method may comprise: receiving, by at least one processor, a plurality of neuromuscular signals of a user, the plurality of neuromuscular signals being sensed and recorded by a plurality of neuromuscular sensors arranged on one or more wearable devices worn by the user; receiving, by the at least one processor, at least one image captured by at least one camera while the plurality of neuromuscular signals are sensed and recorded; determining, by the at least one processor based on information obtained from the at least one image, position information describing a spatial relationship between two or more connected musculoskeletal segments of the user; determining, by the at least one processor based on the plurality of neuromuscular signals, force information; associating, by the at least one processor, the position information with the force information; training, by the at least one processor, an inference model to output a musculoskeletal representation consistent with the position information, or the force information, or the position information and the force information when neuromuscular input signals provided to the inference model have at least one predetermined characteristic, to produce an updated inference model; and causing, by the at least one processor, the updated inference model to be stored in a memory.

In an aspect, the method may further comprise determining, by the at least one processor, the position information based on the information obtained from the at least one image and information obtained from the plurality of neuromuscular signals.

In an aspect, the at least one image may comprise a series of time-sequenced images forming a video.

In an aspect, the musculoskeletal representation may correspond to any one or any combination of: a handstate of the user, a still pose of the user, and a dynamic gesture of the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the method may further comprise: determining, by the at least one processor, a first quality of the plurality of neuromuscular signals, or a second quality of the at least one image, or both the first quality and the second quality; and weighting, by the at least one processor, the plurality of neuromuscular signals, or the at least one image, or both the plurality of neuromuscular signals and the at least one image based on one or both of the first quality and the second quality, to train the inference model.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the method may further comprise determining, by the at least one processor, the first quality in response to a determination that the second quality is greater than a threshold value.

In an aspect, the at least one predetermined characteristic may comprise any one or any combination of: a presence of an artifact of the neuromuscular input signals, a presence of a plurality of artifacts of the neuromuscular input signals, a relative position of a plurality of artifacts of the neuromuscular input signals, a range of amplitudes of the neuromuscular input signals, and a periodic frequency of artifacts of the neuromuscular input signals.

In an aspect, the method may further comprise: receiving, by the at least one processor, inertial measurement unit (IMU) signals output from at least one IMU sensor; and determining, by the at least one processor, the position information based, at least in part, on the IMU signals output from the at least one IMU sensor.

In an aspect, the one or more wearable devices may include at least one positional marker included thereon. The position information may be determined based, at least in part, on the at least one positional marker captured in the at least one image.

According aspects of the technology described herein, a non-transitory computer-readable storage medium storing code that, when executed by at least one computer, causes the at least one computer to perform a method for training an inference model used to generate a musculoskeletal representation is provided. The method may comprise: receiving a plurality of neuromuscular signals of a user, the plurality of neuromuscular signals being sensed and recorded by a plurality of neuromuscular sensors arranged on one or more wearable devices worn by the user; receiving at least one image captured by at least one camera while the plurality of neuromuscular signals are sensed and recorded; determining, based on information obtained from the at least one image, position information describing a spatial relationship between two or more connected musculoskeletal segments of the user; determining, based on the plurality of neuromuscular signals, force information; associating the position information with the force information; training an inference model to output a musculoskeletal representation consistent with the position information, or the force information, or the position information and the force information when neuromuscular input signals provided to the inference model have at least one predetermined characteristic, to produce an updated inference model; and causing the updated inference model to be stored in a memory.

In an aspect, the method may further comprise determining the position information based on the information obtained from the at least one image and information obtained from the plurality of neuromuscular signals.

In an aspect, the at least one image may comprise a series of time-sequenced images forming a video.

In an aspect, the musculoskeletal representation may correspond to any one or any combination of: a handstate of the user, a still pose of the user, and a dynamic gesture of the user.

In an aspect, the at least one image may include any one or any combination of: an image produced by visible light, an image produced by infrared light, an image produced by light of a predetermined range of wavelengths, and an image produced by light of two or more different predetermined ranges of wavelengths.

In an aspect, the method may further comprise: determining a first quality of the plurality of neuromuscular signals, or a second quality of the at least one image, or both the first quality and the second quality; and weighting the plurality of neuromuscular signals, or the at least one image, or both the plurality of neuromuscular signals and the at least one image based on one or both of the first quality and the second quality, to train the inference model.

In a variation of this aspect, the first quality of the plurality of neuromuscular signals may be determined by determining whether at least one of the plurality of neuromuscular signals includes at least one signal artifact.

In another variation of this aspect, the second quality of the at least one image may be determined by determining whether a hand of the user is fully included in a field of view of the at least one camera, or whether the hand is fully occluded from the field of view of the at least one camera, or whether at least a portion of the hand of the user is occluded from the field of view of the at least one camera.

In another variation of this aspect, the method may further comprise determining the first quality in response to a determination that the second quality is greater than a threshold value.

In an aspect, the at least one predetermined characteristic may comprise any one or any combination of: a presence of an artifact of the neuromuscular input signals, a presence of a plurality of artifacts of the neuromuscular input signals, a relative position of a plurality of artifacts of the neuromuscular input signals, a range of amplitudes of the neuromuscular input signals, and a periodic frequency of artifacts of the neuromuscular input signals.

In an aspect, the method may further comprise: receiving inertial measurement unit (IMU) signals output from at least one IMU sensor; and determining the position information based, at least in part, on the IMU signals output from the at least one IMU sensor.

In an aspect, the one or more wearable devices may include at least one positional marker included thereon. The position information may be determined based, at least in part, on the at least one positional marker captured in the at least one image.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIGS. 14A and 14B schematically illustrate components of a computer-based system in which some embodiments of the technology described herein are implemented. FIG. 14A illustrates a wearable portion of the computer-based system, and FIG. 14B illustrates a dongle portion connected to a computer, wherein the dongle portion is configured to communicate with the wearable portion.

DETAILED DESCRIPTION

Figure 1:
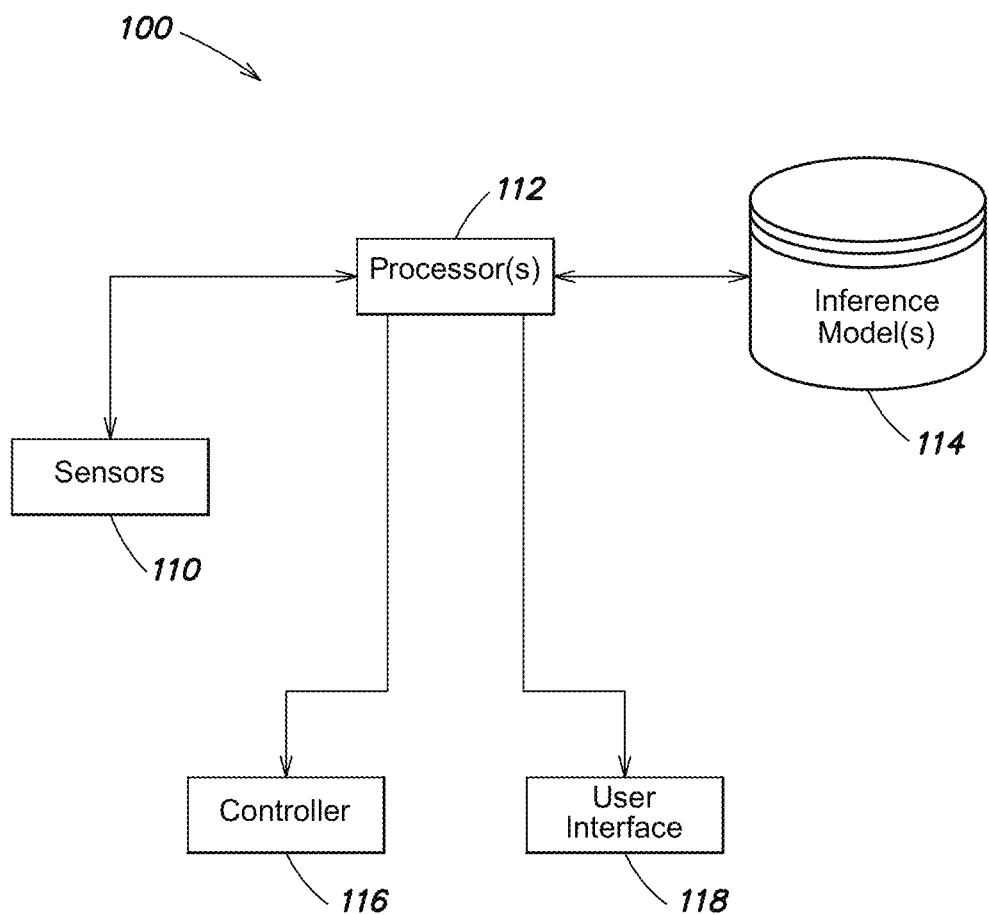
FIG. 1 is a schematic diagram of a computer-based system for processing sensor data, such as signals obtained from neuromuscular sensors, in accordance with some embodiments of the technology described herein.

Some embodiments are directed to coupling a system that senses neuromuscular signals via neuromuscular sensors with a system that performs extended reality (XR) functions. As will be appreciated, XR functions may include augmented reality (AR) functions, virtual reality (VR) functions, mixed reality (MR) functions, and the like. In particular, a system that senses neuromuscular signals for the purpose of determining a position of a body part (e.g., a hand, an arm, etc.) may be used in conjunction with an XR system to provide an improved XR experience for a user. For instance, information gained within both systems may be used to improve the overall XR experience. In embodiments where a musculoskeletal representation associated with the body part is generated based on sensor data, a camera in an XR system may capture data that is used to improve the accuracy of a model of the musculoskeletal representation and/or may be used to calibrate the model. Further, in another implementation, sensor data may provide muscle activation information, which may be visualized and displayed to a user in an XR environment. In yet another implementation, display information in the XR environment may be used as feedback to the user to permit the user to more accurately control his/her musculoskeletal input (e.g., movement input) to the system. Further, control features may be provided that permit neuromuscular signals to control XR system elements, including operation of the XR system itself.

The inventors recognize that neither cameras nor neuromuscular sensors are by themselves ideal input systems. Cameras such as those provided by an XR system may provide good positional information (relative both to other skeletal segments and to external objects) when joint segments are clearly within view, but may be limited by field of view restrictions and occlusion, and may be ill-suited for measuring forces. At the same time, measurements of signals by neuromuscular sensors (e.g., electromyography (EMG) signals or another modality of neuromuscular signal as described herein) may, on their own, be insufficient for distinguishing between forces that a user is applying against himself/herself versus forces that he/she applies to an external object, and such signals may not provide sufficiently accurate information about skeletal geometry, for example finger lengths. According to some embodiments, it is appreciated that it would be beneficial to increase the accuracy of XR systems and neuromuscular-sensor-based systems to provide more accurate and more realistic user experiences.

As will be appreciated, an inference model may involve a generalized skeletal geometry for a type of user (e.g., a typical adult male, a typical child, a typical adult female) or may involve a user-specific skeletal geometry for a particular user (e.g., Jane Miller, Henry Smith).

According to some embodiments, a system is configured to use camera information to improve interpretation of neuromuscular signals and their relationship to movement and force generation. For example, inside-out cameras and/or other camera systems associated with XR systems may be used in association with neuromuscular signals to more accurately represent the position of segments of a user's body, movement of a user's body, and/or representations of force exerted by segments of a user's body. For example, camera information, such as images, video, time series of images, etc., may be used to calibrate neuromuscular systems by providing ground truth labels for data from neuromuscular signals. In one implementation, a system may perform a calibration operation using prompts (e.g., hand gestures, verbal information provided visually or audibly (e.g., words (e.g., "fist") or phrases (e.g., "make a thumbs up gesture")) provided to a user through an XR display or other screen (which may include a smartphone, smartwatch, tablet computer, laptop, desktop computer, AR display, VR display, etc.), where the user is asked to match his/her hand posture to that of a projected hand on the XR display, with the camera optionally assisting with detection of when a match occurs. Further, other types of camera data may be used to calibrate a neuromuscular system, such as calibrating a geometric model of skeletal geometry using camera data. For instance, finger lengths of a geometric model may be verified and/or corrected using camera data. In another example, camera information may be used to determine that two or more parts of a user's body are touching (e.g. the tips of the thumb and index finger touching in a 'pinch' pose). In such a case, images may be processed to automatically identify one or more parts of a user's body (i.e. hand, fingers, and/or wrist) and determine the relative position of the parts of a user's body. For example, the processed camera information may be translated to quaternions or another mathematical framework for representing the segments and joints of a part of a user's body.

In some embodiments, neuromuscular signals, camera data, or both may be used to provide a real-time determination of musculoskeletal representations or gestures. For instance, as neuromuscular (e.g., EMG) and IMU information may be used to determine a more accurate musculoskeletal representation, other data such as camera data may be used to create an even more accurate and consistent representation. Further, it is appreciated that multiple signals can be used, including, but not limited to, signals from one or more cameras, neuromuscular signals from one or more devices, among other types of sensor data, to determine real-time musculoskeletal representations. Other data, such as IMU data and/or camera data, may be used to train and improve an inference model for musculoskeletal representation as well as improve the real-time representation of skeletal position. As will be appreciated, an inference model may be a model that utilizes statistical inference based on a probability distribution to deduce a result; in this regard, an inference model may comprise a statistical model.

As used herein, the term "gestures" refers to a static or dynamic configuration of one or more body parts including the position of the one or more body parts and forces associated with the configuration. For example, gestures include discrete gestures, such as placing or pressing the palm of a hand down on a solid surface or grasping a ball, continuous gestures, such as waving a finger back and forth, grasping and throwing a ball, or a combination of discrete and continuous gestures. Gestures may include covert gestures that are imperceptible to another person, such as slightly tensing a joint by co-contracting opposing muscles or using sub-muscular activations. Gestures may be defined by an application configured to prompt a user to perform the gestures or, alternatively, gestures may be arbitrarily defined by a user. The gestures performed by the user may include symbolic gestures (e.g., gestures mapped to other gestures, interactions, or commands, for example, based on a gesture vocabulary that specifies the mapping). In some cases, hand and arm gestures may be symbolic and used to communicate according to cultural standards.

In some embodiments, a system may combine neuromuscular signals and camera data (e.g., camera signals or image signals from a camera) to infer or reconstruct the position of segments (i.e., skeletal segments) of the user's body. The system may be adapted to adjust a level of influence given to each signal based on the quality of that signal. In the case of a camera signal (e.g., an image signal from a camera), there may be field of view or occlusion restrictions that cause the signal to be unreliable or inaccurate. In the case of neuromuscular signals such as a signal from an EMG sensor, there may be EMG artifacts produced that cause the EMG signal to be unreliable (or other artifacts present in neuromuscular signals derived from an alternative modality of neuromuscular signal, as described below). In such cases, the system may be configured to assess a quality level of each of the signals to determine whether either or both should be used (e.g., to determine a handstate or gesture). The system may also use weighting or another combining method to adjust the degree to which a signal is used between the different types of signal sources (e.g., the different sensor types). Also, when confidence in a particular signal source is high, the signal from that source may be used to train and/or correct another source or model. For instance, a quality of the neuromuscular signals may be assessed in cases where the hand is in clear view of the camera, and a retraining of the handstate model may be performed.

In some embodiments, a system may include a first inference model for generating a musculoskeletal representation based on neuromuscular signals and a second model for generating a musculoskeletal representation based on camera input (i.e., input obtained from a camera). The system may be configured to transition between the use of the first inference model and the use of the second inference model for representing a user's handstate based, at least in part, on information associated with the camera input, such as whether all or a portion of the user's hand is within the camera's field of view. For example, when the user's hand (or another portion of the user's body) is within the camera's field of view, the second inference model may be used to determine the position of the segments of the user's hand, whereas when the user's hand is completely or partially outside the camera's field of view (including cases wherein the user's body is completely or partially occluded), the first inference model may be used to determine the position of the segments of the user's hand representing the handstate. As an alternative implementation, a single inference model that receives both neuromuscular signals and camera input may be used, and the contribution of the inputs may be weighted, as described above. In instances in which the user's hand is out of the field of view of the camera, the camera-input weight may be set to zero or some other small value to reflect the unreliability of the camera input for estimating position information when the user's hand is out of the camera's field of view.

In some embodiments, data from one or more cameras may be used to determine the position of an arm, a hand, a forearm, or another part of the user's body. Also, camera data may be used to combat drift in an IMU-based estimate of forearm position, with the IMU information being used to measure forearm orientation and the neuromuscular signals being used to determine hand and wrist configuration and forces. In this embodiment, positional tracking reference marks on a band of neuromuscular sensors (e.g., a band of EMG sensors) may be used, especially when the camera is used to refine the IMU-based system for tracking one or more position(s) of articulated rigid bodies. As will be appreciated, data from a single camera may be used or data from two or more cameras may be used.

According to some embodiments, camera data may be used for determining whether an object (e.g., a hand, finger, or another physical object) is subjected to a force. For instance, camera data may be used to distinguish between whether someone is moving freely or pressing against object(s) and/or surface(s) (which may include another part of the user's body), determine which object(s) and/or surfaces is or are being interacted with, which position(s) on the surface(s) and/or object(s) are being touched, and can assist with estimating a skeletal configuration, position, and/or force. It is appreciated that although camera data can be used to determine whether a force is being applied, camera data is not particularly suited to determining a magnitude of the force(s) applied. To this end, other input signals (e.g., neuromuscular signals) can be used to determine an amount of force applied and also assist with determining the skeletal configuration and/or position.

When an XR user is applying self force(s) against the user's own body (e.g., the user is pinching his or her own arm), the camera can assist with determining the skeletal configuration and/or position (e.g. which joint segments are involved in touching the arm), and the neuromuscular sensors can be used to determine the intensity of the force. In this way, a more accurate representation of the arm position(s) and/or the hand position(s) and force(s) can be constructed. Further, it is more generally appreciated that the physical context as determined by the cameras could inform priors for estimating the musculoskeletal representation from neuromuscular signals, for example if users are more likely to perform certain movements in specific environments.

Some embodiments are directed to predicting information about the position and movements of portions of a user's arm and/or hand, which may be represented as a multi-segment articulated rigid body system with joints connecting the multiple segments of the rigid body system. For example, in the case of a hand movement, signals sensed and recorded by wearable neuromuscular sensors placed at locations on the user's body (e.g., the user's arm and/or wrist) may be provided as input to an inference model trained to predict estimates of the position (e.g., absolute position, relative position, orientation) and the force(s) associated with a plurality of rigid segments in a computer-based musculoskeletal representation associated with a hand when the user performs one or more hand movements. The combination of position information and force information associated with segments of a musculoskeletal representation associated with a hand is colloquially referred to herein as a "handstate" of the musculoskeletal representation. As a user performs different movements, a trained inference model interprets neuromuscular signals recorded by the wearable neuromuscular sensors into position and force estimates (handstate information) that are used to update the musculoskeletal representation. Because the neuromuscular signals are continuously sensed and recorded, the musculoskeletal representation is updated in real time and a visual representation of a hand (e.g., within an extended reality environment) may be rendered based on the current handstate estimates. As will be appreciated, an estimate of a user's handstate may be used to determine a gesture being performed by the user and/or to predict a gesture that the user will perform.

According to some embodiments, musculoskeletal representations (e.g., hand-rendering) may include actual visual representations of biomimetic (realistic) hands, synthetic (robotic) hands, as well as abstract "internal representations" that serve as input for gesture control (e.g., to other applications, systems, etc.). That is, the hand's position and/or force may be provided to downstream algorithms (e.g., control algorithms in an XR system) but may not be directly rendered. In some embodiments, camera data may be used to assist in creating actual visual representations (e.g., improving an XR version of a user's hands based on the camera data).

According to some embodiments, information received in an EMG context (e.g., force) may be used to control modes of a computer system (e.g., an XR system). For instance, a detection of force (e.g., beyond a threshold amount, such as applied by a finger or a hand) may be used to control the XR system, such as to, for example, open a help dialog interface, open a global system properties menu, or perform a mode switching function. Such dual-mode inputs may also include, for example, submitting a "wake" signal to an XR system or other type of system having heavy computing costs (e.g., high usage of electrical power) because the system wakes or is responsive to the user engaging the system with a position-, force-, or gesture-related event (e.g., the user clenching his or her first results in a wake signal being sent to the XR system). In another implementation, any number of combinations of neuromuscular signals may be used in conjunction with camera data to control a computer system. For instance, in a scenario where a user is selecting an object in an XR environment, the camera data may be used to determine the user's posture, and an EMG signal may be used to inform the XR system that the object has been selected for action (e.g., by detecting a force applied through the EMG signal). It should be appreciated that any combination of modes of control using different types of input data may be performed.

Some embodiments are directed to coupling a system that senses neuromuscular signals with a system that performs XR functions (e.g., AR functions, VR functions, etc.). In particular, a system that senses neuromuscular signals for the purpose of determining a position of a body part (e.g., a hand, an arm, etc.) may be used in conjunction with an XR system to provide an improved XR experience for a user. For instance, information gained within both systems may be used to improve the overall XR experience. In one example, a camera in an AR system may capture data that is used to improve the accuracy of a model of a musculoskeletal representation, used to calibrate the model and/or to control the system(s) using any combination of camera and neuromuscular signals. Further, in another implementation, muscle activation data may be visualized and displayed to a user in an XR environment. In yet another example, display information in the XR environment may be used as feedback to the user to permit the user to more accurately control their musculoskeletal input to the system. Further, control features may be provided that permit neuromuscular signals to control XR system elements.

As discussed above, according to some embodiments of the present technology, a system is configured to use camera information to improve interpretation of neuromuscular signals and their relationship to movement, position, and force generation. As will be appreciated, the camera information may be, for example, an image signal corresponding to at least one image captured by a camera; thus, as used herein, an image from a camera may be understood to refer to an image signal from a camera. The camera may be a still camera, a video camera, an infrared camera, and the like, which is able to capture or record an image of a user. One or more filters may be used on the camera, so that the camera may capture images only within a particular range of wavelengths of light. As will be appreciated, the image may be a still image, a sequence of still images (or image sequence), a moving image (or video sequence), and the like, which may be captured and recorded as a signal. The terms "camera information," "camera data," and "camera signal," may be used herein to represent information about the user that may be captured by a camera. It should be understood that although various embodiments may refer to "a" camera or "the" camera, such embodiments may utilize two or more cameras instead of one camera. Further, the camera information may relate to any one or any combination of: an image produced by visible light, an image produced by non-visible (e.g., infrared) light, an image produced by light of a predetermined range of wavelengths, and an image produced by light of two or more different predetermined ranges of wavelengths. For example, non-visible light may be used to capture an image that shows heat distribution in the user's body, which may provide an indication of blood flow within the user, which in turn may be used to infer a condition of the user (e.g., a force being exerted by a finger of the user may have a different blood-flow pattern than a finger that is not exerting force).

A camera may be mounted on the user (e.g., on an head-mounted display worn by the user, or on a glove worn on the user's hand) or may be mounted external to the user to capture the user and/or the user's environment. When a camera is mounted on the user, the camera may be used to capture the user's environment and/or portions of the user's body (e.g., a hand-mounted camera may be used to capture an image of the user's other hand).

Signals sensed and recorded by wearable sensors placed at locations on the user's body may be provided as input to an inference model trained to generate spatial information for rigid segments of a multi-segment articulated rigid body model of a human body. The spatial information may include, for example, position information of one or more segments, orientation information of one or more segments, joint angles between segments, and the like. As a result of the training, the inference model may implicitly represent inferred motion of the articulated rigid body under defined movement constraints. The trained inference model may output data useable for applications such as rendering a representation of the user's body in a virtual environment, in which the user interacts with physical or virtual objects, and monitoring the user's movements as the user performs a physical activity to assess, for example, whether the user is performing the physical activity in a desired manner. As will be appreciated, the output data from the trained inference model may be used for applications other than those specifically identified herein.

For instance, movement data obtained by a single movement sensor positioned on a user (e.g., on a user's wrist or arm) may be provided as input data to a trained inference model. Corresponding output data generated by the trained inference model may be used to determine spatial information for one or more segments of a multi-segment articulated rigid body model for the user. For example, the output data may be used to determine the position and/or the orientation of one or more segments in the multi-segment articulated rigid body model. In another example, the output data may be used to determine angles between connected segments in the multi-segment articulated rigid body model.

Different types of sensors may be used to provide input data to a trained inference model, as discussed below.

As described herein, in some embodiments, various muscular activation states may be identified directly from recorded sensor data. In other embodiments, handstates, gestures, postures, and the like (collectively referred to as muscular activation states) may be identified based, at least in part, on the output of a trained inference model. In some embodiments, the trained inference model may output motor unit or muscle activations and/or position, orientation, and/or force estimates for segments of a computer-generated musculoskeletal model. In one example, all or portions of a human musculoskeletal system can be modeled as a multi-segment articulated rigid body system, with joints forming the interfaces between the different segments, and with joint angles defining the spatial relationships between connected segments in the model.

Constraints on the movement at a joint are governed by the type of joint connecting the segments and the biological structures (e.g., muscles, tendons, ligaments) that may restrict the range of movement at the joint. For example, a shoulder joint connecting an upper arm to a torso of a body of a human subject, and a hip joint connecting an upper leg to the torso, are ball and socket joints that permit extension and flexion movements as well as rotational movements. By contrast, an elbow joint connecting an upper arm and a lower arm (or forearm), and a knee joint connecting the upper leg and a lower leg for the human subject, allow for a more limited range of motion. In this example, a multi-segment articulated rigid body system may be used to model portions of the human musculoskeletal system. However, it should be appreciated that although some segments of the human musculoskeletal system (e.g., the forearm) may be approximated as a rigid body in the articulated rigid body system, such segments may each include multiple rigid structures (e.g., the forearm may include ulna and radius bones), which enable for more complex movements within the segment that is not explicitly considered by the rigid body model. Accordingly, a model of an articulated rigid body system for use with some embodiments of the technology described herein may include segments that represent a combination of body parts that are not strictly rigid bodies. It will be appreciated that physical models other than the multi-segment articulated rigid body system may be used to model portions of the human musculoskeletal system without departing from the scope of this disclosure.

Continuing with the example above, in kinematics, rigid bodies are objects that exhibit various attributes of motion (e.g., position, orientation, angular velocity, acceleration). Knowing the motion attributes of one segment of a rigid body enables the motion attributes for other segments of the rigid body to be determined based on constraints in how the segments are connected. For example, the hand may be modeled as a multi-segment articulated body, with joints in the wrist and each finger forming interfaces between the multiple segments in the model. In some embodiments, movements of the segments in the rigid body model can be simulated as an articulated rigid body system in which position (e.g., actual position, relative position, or orientation) information of a segment relative to other segments in the model are predicted using a trained inference model, as described in more detail below.

The portion of the human body approximated by a musculoskeletal representation, as described herein as one non-limiting example, is a hand or a combination of a hand with one or more arm segments. The information used to describe a current state of the positional relationships between segments, force relationships for individual segments or combinations of segments, and muscle and motor-unit activation relationships between segments, in the musculoskeletal representation is referred to herein as the handstate of the musculoskeletal representation. It should be appreciated, however, that the techniques described herein are also applicable to musculoskeletal representations of portions of the body other than the hand, including, but not limited to, an arm, a leg, a foot, a torso, a neck, or any combination of the foregoing.

In addition to spatial (e.g., position and/or orientation) information, some embodiments enable a prediction of force information associated with one or more segments of the musculoskeletal representation. For example, linear forces or rotational (torque) forces exerted by one or more segments may be estimated. Examples of linear forces include, but are not limited to, the force of a finger or hand pressing on a solid object such as a table, and a force exerted when two segments (e.g., two fingers) are pinched together. Examples of rotational forces include, but are not limited to, rotational forces created when a segment, such as the wrist or a finger, is twisted or flexed relative to another segment. In some embodiments, the force information determined as a portion of a current handstate estimate includes one or more of: pinching force information, grasping force information, and information about co-contraction forces between muscles represented by the musculoskeletal representation.

Turning now to the figures, FIG. 1 schematically illustrates a system 100, for example, a neuromuscular activity system, in accordance with some embodiments of the technology described herein. The system 100 includes a plurality of sensors 110 (e.g., neuromuscular sensors) configured to sense and record signals arising from neuromuscular activity in skeletal muscle of a human body. The term "neuromuscular activity" as used herein refers to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type able to detect neuromuscular signals. In some embodiments, the plurality of neuromuscular sensors may be arranged relative to the human body and used to sense muscular activity related to a movement of the part of the body controlled by muscles from which the muscular activity is sensed by the neuromuscular sensors. Spatial information (e.g., position and/or orientation information) and force information describing the movement may be predicted based on the sensed neuromuscular signals as the user moves over time.

As the tension of a muscle increases during performance of a motor task, the firing rates of active neurons increases and additional neurons may become active, which is a process referred to as motor unit recruitment. The pattern by which neurons become active and increase their firing rate is stereotyped, such that expected motor unit recruitment patterns may define an activity manifold associated with standard or normal movement. Some embodiments may record activation of a single motor unit or a group of motor units that are "off-manifold," in that the pattern of motor-unit activation is different than an expected or typical motor-unit recruitment pattern. Such off-manifold activation may be referred to herein as, "sub-muscular activation" or "activation of a sub-muscular structure," where a sub-muscular structure refers to the single motor unit or the group of motor units associated with the off-manifold activation. Examples of off-manifold motor-unit recruitment patterns include, but are not limited to, selectively activating a higher-threshold motor unit without activating a lower-threshold motor unit that would normally be activated earlier in the recruitment order and modulating the firing rate of a motor unit across a substantial range without modulating the activity of other neurons that would normally be co-modulated in typical motor-unit recruitment patterns. In some embodiments, the plurality of neuromuscular sensors may be arranged relative to the human body and used to sense sub-muscular activation without observable movement, i.e., without a corresponding movement of the human body that can be readily observed. Sub-muscular activation may be used, at least in part, to control an augmented reality system in accordance with some embodiments of the technology described herein.

The sensors 110 may include one or more Inertial Measurement Units (IMUs), which measure a combination of physical aspects of motion, using, for example, an accelerometer, a gyroscope, a magnetometer, or any combination of one or more accelerometers, gyroscopes, and magnetometers. In some embodiments, IMUs may be used to sense information about the movement of the part of the body on which the IMU is attached, and information derived from the sensed data (e.g., position and/or orientation information) may be tracked as the user moves over time. For example, one or more IMUs may be used to track movements of portions (e.g., arms, legs) of a user's body proximal to the user's torso relative to the IMU(s) as the user moves over time.

In embodiments that include at least one IMU and a plurality of neuromuscular sensors, the IMU(s) and the neuromuscular sensors may be arranged to detect movement of different parts of a human body. For example, the IMU(s) may be arranged to detect movements of one or more body segments proximal to the torso (e.g., movements of an upper arm), whereas the neuromuscular sensors may be arranged to detect movements of one or more body segments distal to the torso (e.g., movements of a lower arm (forearm) or a wrist). (The terms "lower arm" and "forearm" may be used interchangeably herein.) It should be appreciated, however, that the sensors (i.e., the IMU(s) and the neuromuscular sensors) may be arranged in any suitable way, and embodiments of the technology described herein are not limited based on the particular sensor arrangement. For example, in some embodiments, at least one IMU and a plurality of neuromuscular sensors may be co-located on a body segment to track movements of the body segment using different types of measurements. In one implementation described in more detail below, an IMU and a plurality of EMG sensors are arranged on a wearable device structured to be worn around the lower arm or the wrist of a user. In such an arrangement, the IMU may be configured to track, over time, movement information (e.g., positioning and/or orientation) associated with one or more arm segments, to determine, for example, whether the user has raised or lowered his/her arm, whereas the EMG sensors may be configured to determine movement information associated with wrist and/or hand segments to determine, for example, whether the user has an open or a closed hand configuration, or to determine sub-muscular information associated with activation of sub-muscular structures in muscles of the wrist and/or the hand.

Some or all of the sensors 110 may include one or more sensing components configured to sense information about a user. In the case of IMUs, the sensing component(s) of an IMU may include one or more: accelerometers, gyroscopes, magnetometers, or any combination thereof, to measure or sense characteristics of body motion and/or characteristics related to body motion, examples of which include, but are not limited to, acceleration, angular velocity, and a magnetic field around the body during the body motion. In the case of neuromuscular sensors, the sensing component(s) may include, but are not limited to, one or more: electrodes that detect electric potentials on the surface of the body (e.g., for EMG sensors), vibration sensors that measure skin surface vibrations (e.g., for MMG sensors), acoustic sensing components that measure ultrasound signals (e.g., for SMG sensors) arising from muscle activity.

In some embodiments, at least some of the plurality of sensors 110 may be arranged as a portion of a wearable device structured to be worn on or around a part of a user's body. For example, in one non-limiting example, an IMU and a plurality of neuromuscular sensors may be arranged circumferentially on an adjustable and/or elastic band, such as a wristband or an armband configured to be worn around a user's wrist or arm. Alternatively, at least some of the sensors 110 may be arranged on a wearable patch structured to be affixed to a portion of the user's body. In some embodiments, multiple wearable devices, each having one or more IMUs and/or neuromuscular sensors included thereon may be used to generate control information based on activation from sub-muscular structures and/or based on movement that involves multiple parts of the body.

Figure 12:
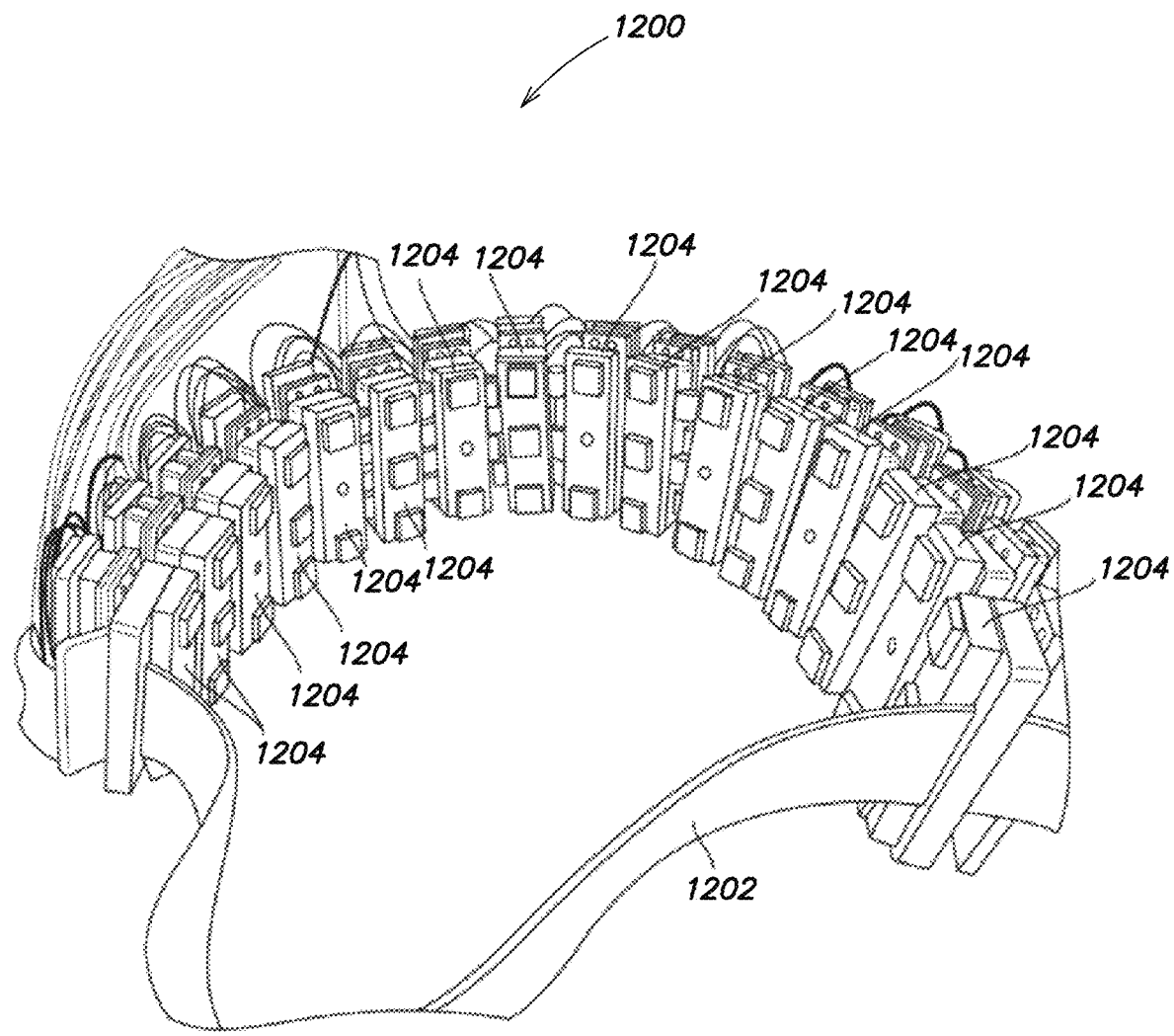
FIG. 12 illustrates a wristband having EMG sensors arranged circumferentially thereon, in accordance with some embodiments of the technology described herein.

In one implementation, the sensors 110 may include sixteen neuromuscular sensors arranged circumferentially around a band (e.g., an elastic band) structured to be worn around a user's lower arm (e.g., encircling the user's forearm). For example, FIG. 12 shows an embodiment of a wearable system in which neuromuscular sensors 1204 (e.g., EMG sensors) are arranged circumferentially around an elastic band 1202. It should be appreciated that any suitable number of neuromuscular sensors may be used and the number and arrangement of neuromuscular sensors used may depend on the particular application for which the wearable system is used. For example, a wearable armband or wristband may be used to generate control information for controlling an augmented reality system, controlling a robot, controlling a vehicle, scrolling through text, controlling a virtual avatar, or any other suitable control task. In some embodiments, the elastic band 1202 may also include one or more IMUs (not shown), configured to sense and record movement information, as discussed above.

Figure 13A:
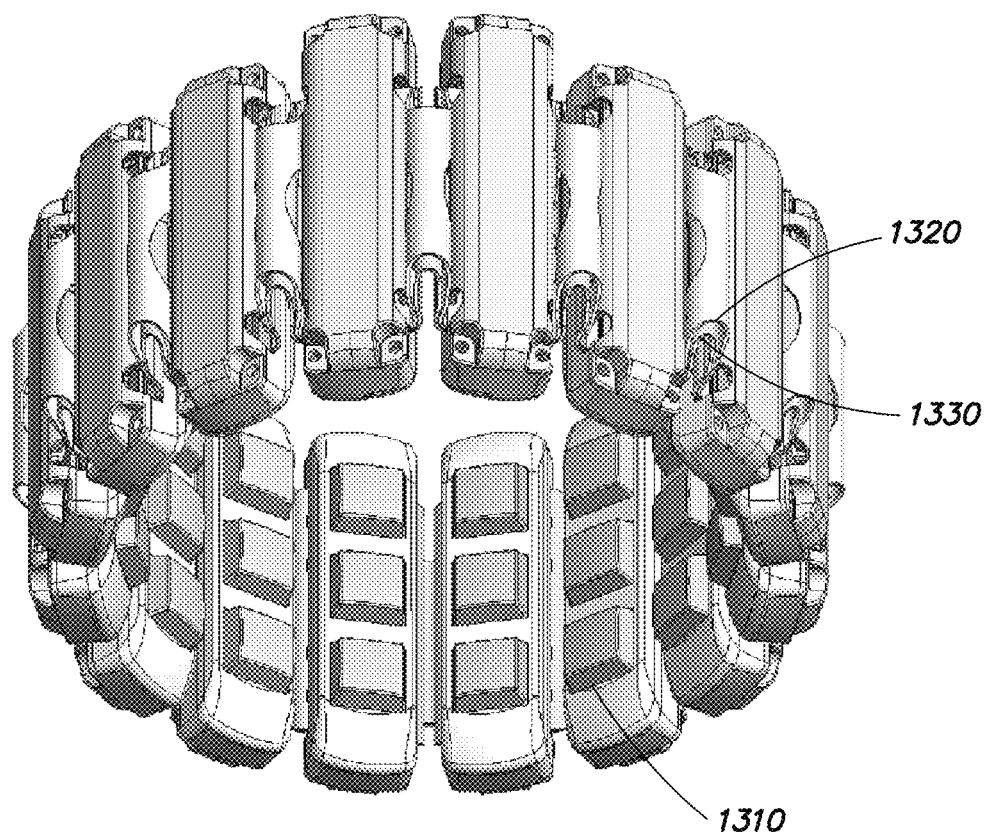
FIG. 13A illustrates a wearable system with sixteen EMG sensors arranged circumferentially around a band configured to be worn around a user's lower arm or wrist, in accordance with some embodiments of the technology described herein.

FIGS. 13A-13B and 14A-14B show other embodiments of a wearable system of the present technology. In particular, FIG. 13A illustrates a wearable system with a plurality of sensors 1310 arranged circumferentially around an elastic band 1320 structured to be worn around a user's lower arm or wrist. The sensors 1310 may be neuromuscular sensors (e.g., EMG sensors). As shown, there may be sixteen sensors 1310 arranged circumferentially around the elastic band 1320 at a regular spacing. It should be appreciated that any suitable number of sensors 1310 may be used, and the spacing need not be regular. The number and arrangement of the sensors 1310 may depend on the particular application for which the wearable system is used. For instance, the number and arrangement of the sensors 1310 may differ when the wearable system is to be worn on a wrist in comparison with a thigh. A wearable system (e.g., armband, wristband, thighband, etc.) can be used to generate control information for controlling an augmented reality system, controlling a robot, controlling a vehicle, scrolling through text, controlling a virtual avatar, and/or performing any other suitable control task.

Figure 13B:
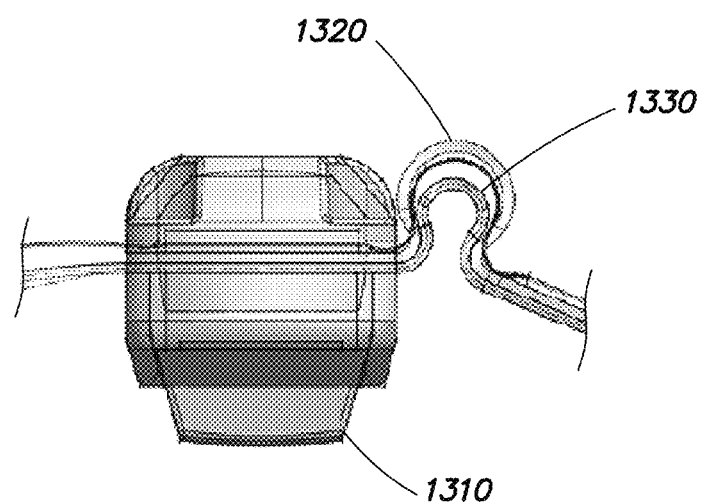
FIG. 13B is a cross-sectional view through one of the sixteen EMG sensors illustrated in FIG. 13A.

In some embodiments, the sensors 1310 may include only a set of neuromuscular sensors (e.g., EMG sensors). In other embodiments, the sensors 1310 may include a set of neuromuscular sensors and at least one auxiliary device. The auxiliary device(s) may be configured to continuously sense and record one or a plurality of auxiliary signal(s). Examples of auxiliary devices include, but are not limited to, IMUs, microphones, imaging devices (e.g., cameras), radiation-based sensors for use with a radiation-generation device (e.g., a laser-scanning device), heart-rate monitors, and other types of devices, which may capture a user's condition or other characteristics of the user. As shown in FIG. 13A, the sensors 1310 may be coupled together using flexible electronics 1330 incorporated into the wearable system. FIG. 13B illustrates a cross-sectional view through one of the sensors 1310 of the wearable system shown in FIG. 13A.

In some embodiments, the output(s) of one or more of sensing component(s) of the sensors 1310 can be optionally processed using hardware signal-processing circuitry (e.g., to perform amplification, filtering, and/or rectification). In other embodiments, at least some signal processing of the output(s) of the sensing component(s) can be performed using software. Thus, signal processing of signals sampled by the sensors 1310 can be performed by hardware or by software, or by any suitable combination of hardware and software, as aspects of the technology described herein are not limited in this respect. A non-limiting example of a signal-processing procedure used to process recorded data from the sensors 1310 is discussed in more detail below in connection with FIGS. 14A and 14B.

FIGS. 14A and 14B illustrate a schematic diagram with internal components of a wearable system with sixteen sensors (e.g., EMG sensors), in accordance with some embodiments of the technology described herein. As shown, the wearable system includes a wearable portion 1410 (FIG. 14A) and a dongle portion 1420 (FIG. 14B). Although not illustrated, the dongle portion 1420 is in communication with the wearable portion 1410 (e.g., via Bluetooth or another suitable short range wireless communication technology). As shown in FIG. 14A, the wearable portion 1410 includes the sensors 1310, examples of which are described above in connection with FIGS. 13A and 13B. The sensors 1310 provide output (e.g., recorded signals) to an analog front end 1430, which performs analog processing (e.g., noise reduction, filtering, etc.) on the recorded signals. Processed analog signals produced by the analog front end 1430 are then provided to an analog-to-digital converter 1432, which converts the processed analog signals to digital signals that can be processed by one or more computer processors. An example of a computer processor that may be used in accordance with some embodiments is a microcontroller (MCU) 1434. As shown in FIG. 14A, the MCU 1434 may also receive inputs from other sensors (e.g., an IMU 1440) and from a power and battery module 1442. As will be appreciated, the MCU 1434 may receive data from other devices not specifically shown. A processing output by the MCU 1434 may be provided to an antenna 1450 for transmission to the dongle portion 1420, shown in FIG. 14B.

The dongle portion 1420 includes an antenna 1452 that communicates with the antenna 1450 of the wearable portion 1410. Communication between the antennas 1450 and 1452 may occur using any suitable wireless technology and protocol, non-limiting examples of which include radiofrequency signaling and Bluetooth. As shown, the signals received by the antenna 1452 of the dongle portion 1420 may be provided to a host computer for further processing, for display, and/or for effecting control of a particular physical or virtual object or objects (e.g., to perform a control operation in an AR or VR environment)

Although the examples provided with reference to FIGS. 13A, 13B, 14A, and 14B are discussed in the context of interfaces with EMG sensors, it is to be understood that the wearable systems described herein can also be implemented with other types of sensors, including, but not limited to, mechanomyography (MMG) sensors, sonomyography (SMG) sensors, and electrical impedance tomography (EIT) sensors.

Returning to FIG. 1, in some embodiments, sensor data recorded by the sensors 110 may be optionally processed to compute additional derived measurements, which may then be provided as input to an inference model, as described in more detail below. For example, recorded signals from an IMU may be processed to derive an orientation signal that specifies the orientation of a segment of a rigid body over time. The sensors 110 may implement signal processing using components integrated with the sensing components of the sensors 110, or at least a portion of the signal processing may be performed by one or more components in communication with, but not directly integrated with, the sensing components of the sensors 110.

The system 100 also includes one or more computer processors 112 programmed to communicate with sensors 110. For example, signals recorded by one or more of the sensors 110 may be output from the sensor(s) 110 and provided to the processor(s) 112, which may be programmed to execute one or more machine-learning algorithms to process the signals output by the sensor(s) 110. The algorithm(s) may process the signals to train (or retrain) one or more inference models 114, and the resulting trained (or retrained) inference model(s) 114 may be stored for later use in generating control signals and controlling an XR system, as described in more detail below.

In some embodiments, the inference model(s) 114 may include a neural network and, for example, may be a recurrent neural network. In some embodiments, the recurrent neural network may be a long short-term memory (LSTM) neural network. It should be appreciated, however, that the recurrent neural network is not limited to being an LSTM neural network and may have any other suitable architecture. For example, in some embodiments, the recurrent neural network may be any one or any combination of: a fully recurrent neural network, a gated recurrent neural network, a recursive neural network, a Hopfield neural network, an associative memory neural network, an Elman neural network, a Jordan neural network, an echo state neural network, and a second-order recurrent neural network, and/or any other suitable type of recurrent neural network. In other embodiments, neural networks that are not recurrent neural networks may be used. For example, deep neural networks, convolutional neural networks, and/or feedforward neural networks may be used.

In some embodiments, the inference model(s) 114 may produce discrete outputs. Discrete outputs (e.g., discrete classifications) may be used, for example, when a desired output is to know whether a particular pattern of activation (including individual neural spiking events) is currently being performed by a user. For example, the inference model(s) 114 may be trained to estimate whether the user is activating a particular motor unit, activating a particular motor unit with a particular timing, activating a particular motor unit with a particular firing pattern, or activating a particular combination of motor units. On a shorter time scale, a discrete classification may be used in some embodiments to estimate whether a particular motor unit fired an action potential within a given amount of time. In such a scenario, these estimates may then be accumulated to obtain an estimated firing rate for that motor unit.

In embodiments in which an inference model is implemented as a neural network configured to output a discrete output, the neural network may include an output layer that is a softmax layer, such that outputs of the inference model add up to one and may be interpreted as probabilities. For instance, the outputs of the softmax layer may be a set of values corresponding to a respective set of control signals, with each value indicating a probability that the user wants to perform a particular control action. As one non-limiting example, the outputs of the softmax layer may be a set of three probabilities (e.g., 0.92, 0.05, and 0.03) indicating the respective probabilities that a detected pattern of activity is one of three known patterns.

It should be appreciated that when an inference model is a neural network configured to output a discrete output (e.g., a discrete signal), the neural network is not required to produce outputs that add up to one. For example, for some embodiments, instead of a softmax layer, the output layer of the neural network may be a sigmoid layer, which does not restrict the outputs to probabilities that add up to one. In such embodiments, the neural network may be trained with a sigmoid cross-entropy cost. Such an implementation may be advantageous in cases where multiple different control actions may occur within a threshold amount of time and it is not important to distinguish an order in which these control actions occur (e.g., a user may activate two patterns of neural activity within the threshold amount of time). In some embodiments, any other suitable non-probabilistic multi-class classifier may be used, as aspects of the technology described herein are not limited in this respect.

In some embodiments, an output of the inference model(s) 114 may be a continuous signal rather than a discrete signal. For example, the model(s) 114 may output an estimate of a firing rate of each motor unit, or the model(s) 114 may output a time-series electrical signal corresponding to each motor unit or sub-muscular structure.

It should be appreciated that aspects of the technology described herein are not limited to using neural networks, as other types of inference models may be employed in some embodiments. For example, in some embodiments, the inference model(s) 114 may comprise a hidden Markov model (HMM), a switching HMM in which switching allows for toggling among different dynamic systems, dynamic Bayesian networks, and/or any other suitable graphical model having a temporal component. Any such inference model may be trained using recorded sensor signals.

As another example, in some embodiments, the inference model(s) 114 may be a classifier that takes, as input, features derived from the recorded sensor signals. In such embodiments, the classifier may be trained using features extracted from the sensor signals. The classifier may be, e.g., a support vector machine, a Gaussian mixture model, a regression based classifier, a decision tree classifier, a Bayesian classifier, and/or any other suitable classifier, as aspects of the technology described herein are not limited in this respect. Input features to be provided to the classifier may be derived from the sensor signals in any suitable way. For example, the sensor signals may be analyzed as time-series data using wavelet analysis techniques (e.g., continuous wavelet transform, discrete-time wavelet transform, etc.), Fourier-analytic techniques (e.g., short-time Fourier transform, Fourier transform, etc.), and/or any other suitable type of time-frequency analysis technique. As one non-limiting example, the sensor signals may be transformed using a wavelet transform and the resulting wavelet coefficients may be provided as inputs to the classifier.

In some embodiments, values for parameters of the inference model(s) 114 may be estimated from training data. For example, when the inference model(s) 114 is a neural network, parameters of the neural network (e.g., weights) may be estimated from the training data. In some embodiments, parameters of the inference model(s) 114 may be estimated using gradient descent, stochastic gradient descent, and/or any other suitable iterative optimization technique. In embodiments where the inference model(s) 114 is a recurrent neural network (e.g., an LSTM), the inference model(s) 114 may be trained using stochastic gradient descent and backpropagation through time. The training may employ a squared error or cross-entropy loss function and/or any other suitable loss function, as aspects of the technology described herein are not limited in this respect.

The system 100 also may optionally include one or more controller(s) 116. For example, the controller(s) 116 may include a display controller configured to display a visual representation (e.g., a representation of a hand). As discussed in more detail below, the one or more computer processors 112 may implement one or more trained inference models that receive, as input, signals sensed and recorded by the sensors 110 and that provide, as output, information (e.g., predicted handstate information) that may be used to generate control signals and control an augmented reality system.

The system 100 also may optionally include a user interface 118. Feedback determined based on the signals recorded by the sensors 110 and processed by the processor(s) 112 may be provided via the user interface 118 to facilitate a user's understanding of how the system 100 is interpreting the user's intended activation. The user interface 118 may be implemented in any suitable way, including, but not limited to, an audio interface, a video interface, a tactile interface, and electrical stimulation interface, or any combination of the foregoing.

In some embodiments, a computer application that simulates a virtual reality (VR) or augmented reality (AR) environment may be instructed to provide a visual representation by displaying a visual character, such as an avatar (e.g., via the controller(s) 116). Positioning, movement, and/or forces applied by portions of the visual character within the virtual reality environment may be displayed based on an output of the trained inference model(s) 114. The visual representation may be dynamically updated as continuous signals are sensed and recorded by the sensors 110 and processed by the trained inference model(s) 114 to provide a computer-generated visual representation of the character's movement that is updated in real-time.

Information generated in either system (AR camera inputs, sensor inputs) can be used to improve user experience, accuracy, feedback, inference models, calibration functions, and other aspects in the overall system. To this end, in an AR environment for example, the system 100 may include an AR system that includes one or more processors, a camera, and a display (e.g., the user interface 118, or other interface via AR glasses or other viewing device) that provides AR information within a view of the user. The system 100 may also include system elements that couple the AR system with a computer-based system that generates the musculoskeletal representation based on sensor data. For example, the systems may be coupled via a special-purpose or other type of computer system that receives inputs from the AR and system that generates the computer-based musculoskeletal representation. Such a system may include a gaming system, robotic control system, personal computer, or other system that is capable of interpreting AR and musculoskeletal information. The AR system and the system that generates the computer-based musculoskeletal representation may also be programmed to communicate directly. Such information may be communicated using any number of interfaces, protocols, or media.

As discussed above, some embodiments are directed to using an inference model for predicting musculoskeletal information based on signals sensed and recorded by wearable sensors. As discussed briefly above in the example where portions of the human musculoskeletal system can be modeled as a multi-segment articulated rigid body system, the types of joints between segments in a multi-segment articulated rigid body model may serve as constraints that constrain movement of the rigid body. Additionally, different human individuals may move in characteristic ways when performing a task that can be captured in statistical patterns that may be generally applicable to individual user behavior. At least some of these constraints on human body movement may be explicitly incorporated into inference models used for prediction of user movement, in accordance with some embodiments. Additionally or alternatively, the constraints may be learned by the inference model though training based on recorded sensor data, as discussed briefly above.

As discussed above, some embodiments are directed to using an inference model for predicting handstate information to enable generation of a computer-based musculoskeletal representation and/or a real-time update of a computer-based musculoskeletal representation. The inference model may be used to predict the handstate information based on IMU signals, neuromuscular signals (e.g., EMG, MMG, and/or SMG signals), external device signals (e.g., camera or laser-scanning signals), or a combination of IMU signals, neuromuscular signals, and external device signals detected as a user performs one or more movements. For instance, as discussed above, a camera associated with an AR system may be used to capture data of an actual position of a human subject of the computer-based musculoskeletal representation, and such actual-position information may be used to improve the accuracy of the representation. Further, outputs of the inference model may be used to generate a visual representation of the computer-based musculoskeletal representation in an XR environment. For example, a visual representation of muscle groups firing, force being applied, text being entered via movement, or other information produced by the computer-based musculoskeletal representation may be rendered in a visual display of an XR system. In some embodiments, other input/output devices (e.g., auditory inputs/outputs, haptic devices, etc.) may be used to further improve the accuracy of the overall system and/or to improve user experience.

Some embodiments of the technology described herein are directed to using an inference model, at least in part, to map muscular-activation state information, which is information identified from neuromuscular signals sensed and recorded by neuromuscular sensors, to control signals. The inference model may receive as input IMU signals, neuromuscular signals (e.g., EMG, MMG, and/or SMG signals), external device signals (e.g., camera or laser-scanning signals), or a combination of IMU signals, neuromuscular signals, and external device signals detected as a user performs one or more sub-muscular activations, one or more movements, and/or one or more gestures. The inference model may be used to predict control information without the user having to make perceptible movements.

Figure 2:
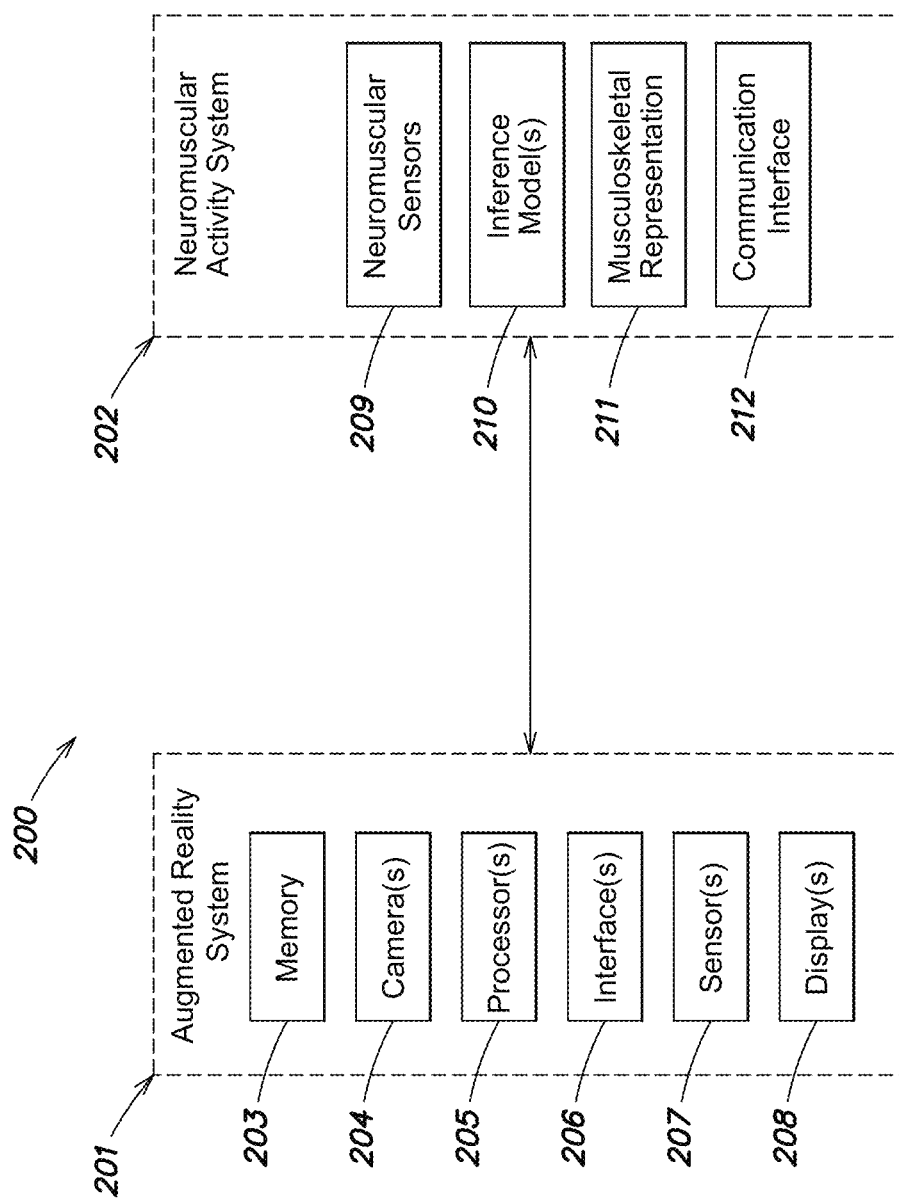
FIG. 2 is a schematic diagram of a distributed computer-based system that integrates an augmented reality (AR) system with a neuromuscular activity system, in accordance with some embodiments of the technology described herein.

FIG. 2 illustrates a schematic diagram of an AR-based system 200, which may be a distributed computer-based system that integrates an augmented reality (AR) system 201 with a neuromuscular activity system 202. The neuromuscular activity system 202 is similar to the system 100 described above with respect to FIG. 1.

Generally, an augmented reality, such as the AR system 201, may take the form of a pair of goggles or glasses, or eyewear, or other type of display device that shows display elements to a user that may be superimposed on the user's "reality." This reality in some cases could be the user's view of the environment (e.g., as viewed through the user's eyes), or a captured version (e.g., by camera(s)) of the user's view of the environment. In some embodiments, the AR system 201 may include one or more cameras (e.g., camera(s) 204), which may be mounted within a device worn by a user, that captures one or more views experienced by the user in the user's environment. The system 201 may have one or more processor(s) 205 operating within the device worn by the user and/or within a peripheral device or computer system, and such processor(s) 205 may be capable of transmitting and receiving video information and other types of data (e.g., sensor data).

The AR system 201 may also include one or more sensor(s) 207, such as microphones, GPS elements, accelerometers, infrared detectors, haptic feedback elements, or any other type of sensor, or any combination thereof. In some embodiments, the AR system 201 may be an audio-based or auditory AR system and the one or more sensor(s) 207 may also include one or more headphones or speakers. Further, the AR system 201 may also have one or more display(s) 208 that permit the AR system 201 to overlay and/or display information to the user in addition to providing the user with a view of the user's environment as presented by the AR system 201. The AR system 201 may also include one or more communication interface(s) 206, which enable information to be communicated to one or more computer systems (e.g., a gaming system or other system capable of rendering or receiving AR data). AR systems can take many forms and are available from a number of different manufacturers. For example, various embodiments may be implemented in association with one or more types of AR systems, such as HoloLens holographic reality glasses available from the Microsoft Corporation (Redmond, Wash., USA), Lightwear AR headset from Magic Leap (Plantation, Fla., USA), Google Glass AR glasses available from Alphabet (Mountain View, Calif., USA), R-7 Smartglasses System available from Osterhout Design Group (also known as ODG; San Francisco, Calif., USA), or any other type of AR and/or VR device. Although discussed by way of example, it should be appreciated that one or more embodiments may be implemented within a VR system.

The AR system 201 may be operatively coupled to the neuromuscular activity system 202 through one or more communication schemes or methodologies, including but not limited to, Bluetooth protocol, Wi-Fi, Ethernet-like protocols, or any number of connection types, wireless and/or wired. It should be appreciated that, for example, the systems 201 and 202 may be directly connected or coupled through one or more intermediate computer systems or network elements. The double-headed arrow in FIG. 2 represents the communicative coupling between the systems 201 and 202.

As mentioned earlier, the neuromuscular activity system 202 may be similar in structure and function to the system 100 described above with reference to FIG. 1. In particular, the system 202 may include one or more neuromuscular sensor(s) 209, one or more inference model(s) 210, and may create, maintain, and store a musculoskeletal representation 211. In an example embodiment, similar to one discussed above, the system 202 may include or may be implemented as a wearable device, such as a band that can be worn by a user, in order to collect and analyze neuromuscular signals from the user. Further, the system 202 may include one or more communication interface(s) 212 that permit the system 202 to communicate with the AR system 201, such as by Bluetooth, Wi-Fi, or other communication method. Notably, the AR system 201 and the neuromuscular activity system 202 may communicate information that can be used to enhance user experience and/or allow the AR system 201 to function more accurately and effectively.

While FIG. 2 shows a distributed computer-based system 200 that integrates the AR system 201 with the neuromuscular activity system 202, it will be understood integration of these systems 201 and 201 may be non-distributed in nature. In some embodiments, the neuromuscular activity system 202 may be integrated into the AR system 201 such that the various components of the neuromuscular activity system 202 may be considered as part of the AR system 201. For example, inputs from the neuromuscular sensor(s) 209 may be treated as another of the inputs (e.g., from the camera(s) 204, from the sensor(s) 207) to the AR system 201. In addition, processing of the inputs (e.g., sensor signals) obtained from the neuromuscular sensors 209 may be integrated into the AR system 201.

Figure 3:
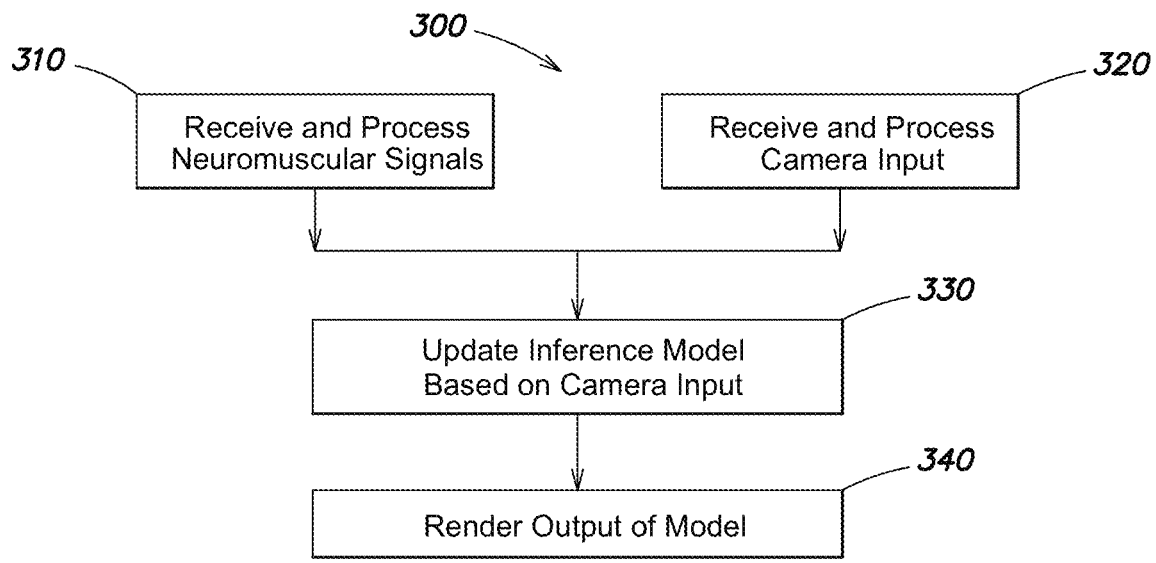
FIG. 3 is a flowchart of a process for processing neuromuscular signals and camera data in accordance with some embodiments of the technology described herein.

FIG. 3 shows a flowchart of a process 300 for processing neuromuscular signals and camera or signals inputs in accordance with some embodiments of the technology described herein. The process 300 may be implemented on a system such as, for example, the AR-based system 200, the AR system 201, the neuromuscular activity system 202, and/or a separate computer system to which the systems 201, 202 provide signal inputs. In one implementation, the process 300 may be performed by the neuromuscular activity system 202. In act 310, sensor signals may be sensed and recorded by one or more sensor(s) (also referred to herein as "raw sensor signals") of the neuromuscular activity system 202. In some embodiments, the sensor(s) may include a plurality of neuromuscular sensors 209 (e.g., EMG sensors) arranged on a wearable device worn by a user. For example, the sensors 209 may be EMG sensors arranged on an elastic band configured to be worn around a wrist or a forearm of a user to record neuromuscular signals from the user as the user performs various movements or gestures. In some embodiments, the EMG sensors may be the sensors 1204 arranged on the band 1202, as shown in FIG. 12; in some embodiments, the EMG sensors may be the sensors 1310 arranged on the elastic band 1320, as shown in FIG. 13A. The gestures performed by the user may include static gestures, such as placing the user's hand palm down on a table; dynamic gestures, such as waving a finger back and forth; and covert gestures that are imperceptible to another person, such as slightly tensing a joint by co-contracting opposing muscles, pressing on an object or surface, or using sub-muscular activations. The gestures performed by the user may include symbolic gestures (e.g., gestures mapped to other gestures, interactions, or commands, for example, based on a gesture vocabulary that specifies the mapping).

In addition to a plurality of neuromuscular sensors, some embodiments of the technology described herein may include one or more auxiliary sensor(s) configured to record auxiliary signals that may also be provided as input to the one or more trained inference model(s), as discussed above.

Examples of auxiliary sensors include IMUs, imaging devices, radiation detection devices (e.g., laser scanning devices), heart rate monitors, or any other type of biosensor configured to sense and record biophysical information from a user during performance of one or more movements or gestures. According to one embodiment, as shown in the process 300 of FIG. 3 at act 320, the system receives and processes one or more camera inputs. Such inputs may include one or more raw signals, such as signals of images, video, stream, etc., or signals of one or more pre-processed forms, such as signals of a representation of a detected object, a 3D model, etc., and/or other information, such as information reflecting a state of the camera inputs. Further, it should be appreciated that some embodiments may be implemented using camera-based systems that perform skeletal tracking, such as, for example, the Kinect system available from the Microsoft Corporation (Redmond, Wash., USA) and the LeapMotion system available from Leap Motion, Inc. (San Francisco, Calif., USA). It should be appreciated that any combination of hardware and/or software may be used to implement various embodiments described herein.

The acts 310 and 320 may also include processing acts themselves, where raw sensor signals, which may include the signals sensed and recorded by the one or more sensor(s) (e.g., EMG sensors, IMUs) and/or the camera input signals from the one more camera(s), are optionally processed. In some embodiments, the raw sensor signals may be processed using hardware signal-processing circuitry (e.g., to perform amplification, filtering, and/or rectification). In other embodiments, at least some signal processing of the raw sensor signals may be performed using software. Accordingly, signal processing of the raw sensor signals, sensed and recorded by the one or more sensor(s) and/or obtained from the one or more camera(s), may be performed using hardware, or software, or any suitable combination of hardware and software. In some implementations, the raw sensor signals may be processed to derive other signal data. For example, accelerometer data recorded by one or more IMU(s) may be integrated and/or filtered to determine derived signal data associated with one or more muscles during activation of a muscle or performance of a gesture.

The process 300 then proceeds to act 330, where the raw sensor signals (e.g., the neuromuscular signals and the camera input signals) or the processed versions of the raw sensor signals are optionally provided as input to the trained inference model(s), which is or are configured to produce user-movement information, such as handstate information, as described above.

The process 300 then proceeds to act 340, where outputs of the trained inference model(s) are provided. For instance, in some embodiments, control outputs of the system are provided based on the raw sensor signals, the processed sensor signals, and/or the outputs of the trained inference model(s) (e.g., handstate information and/or other rendered output of the trained inference model(s), etc.). For example, in some embodiments, the AR system 201 may receive a rendered output that the AR system 210 (or other system display) can display as a rendered gesture.

According to some embodiments, one or more computer processors (e.g., the processor(s) 112 of the system 100, or the processor(s) 205 of the AR-based system 200) may be programmed to identify one or more muscular activation states of a user from raw sensor signals (e.g., signals sensed and recorded by the sensor(s) discussed above and/or camera input signals) and/or information based on these signals. The information based on the signals the raw sensor signals may include information associated with processed sensor signals (e.g., processed EMG signals) and/or information associated with outputs of the trained inference model(s) (e.g., handstate information). The one or more muscular activation states of the user may include a static gesture performed by the user, a dynamic gesture performed by the user, a sub-muscular activation state of the user, and/or a muscular tensing performing by the user. The one or more muscular activation states of the user may be defined by one or more pattern(s) of muscle activity and/or one or more motor unit activation(s) detected in the raw sensor signals and/or information based on the raw sensor signals, associated with various movements or gestures performed by the user.

Figure 4:
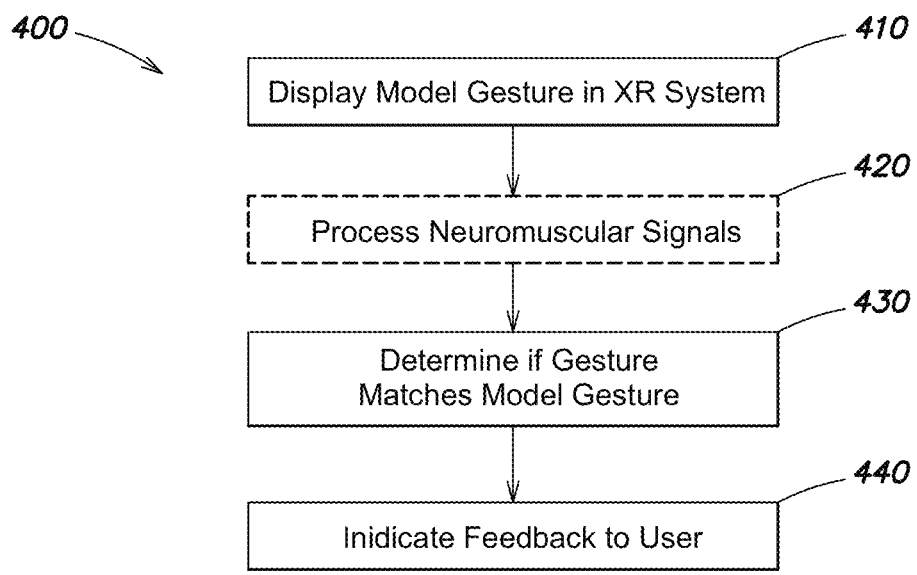
FIG. 4 is a flowchart of a process for processing gesture information in an XR system in accordance with some embodiments of the technology described herein.

FIG. 4 is a flowchart of a process 400 for processing gesture information in an AR-based system in accordance with some embodiments of the technology described herein. In particular, there may be a number of different use scenarios wherein an AR system may be used in association with a neuromuscular activity system for providing a user experience. As shown in FIG. 4, according to the process 400, at act 410, the AR-based system may be configured to display a model gesture to a user within a display of the AR-based system. For example, the AR-based system may be adapted to display a throwing motion or other gesture type that the user would like to mimic or learn. To this end, the AR-based system may display an example of a gesture to the user while the user tries to emulate that particular gesture. At act 420, a neuromuscular activity system processes neuromuscular signals produced by the user while emulating that gesture. At act 430, the neuromuscular activity system determines whether the emulated gesture matches a model of that gesture. Such a determination may be made, for example, using one or more 3D reference model(s) and comparing outputs of an inference model that measures or compares the user's emulated gesture versus a reference model of the gesture. Acceptable matches may occur within certain predefined ranges or error levels between two or more reference models. It should be appreciated that camera data (e.g., input signals from a camera) may also be used (either alone or in combination with the neuromuscular signals) to determine whether a match occurs. For instance, in such cases where neuromuscular signals (e.g., EMG signals) are not available, a match may be detected exclusively using camera data.

Further, the inference model may also be trained to provide an indication of a match between models. At act 440, feedback may be provided to the user (discussed in more detail below in connection with FIG. 5), such as a display indication within an AR display (e.g., a light or other indicator identifying that the gesture was matched or was not matched); an audio output (e.g., an audio signal for spoken words such as "great job", "match", etc.); haptic feedback; electrical stimulation; and/or other output perceivable by the user. It should be appreciated that one aspect of such a comparison may include a prediction as to whether the gesture will be completed correctly (or incorrectly). For example, hardware and/or software in the AR-based system may perform a routine for a predictive measure that is capable of determining whether the user is likely to successfully complete the gesture. In one example implementation, an audio output may be presented to the user when the predictive measure indicates that the user will be unsuccessful.

As will be appreciated, the feedback to the user may relate to a user's position relative to a camera. For example, if the user is wholly or partially occluded from the camera's field of view, the feedback may inform the user when a relevant part of the user's body is in view.

It should be appreciated that, in some embodiments, some outputs may be delivered to the user before completion of the gesture, based on a prediction of the gesture (e.g., the user may receive an electric stimulus indicating that the user's attempt at performing the gesture will be unsuccessful before the user completes the gesture). Also, it should be appreciated that although a matching operation may be performed for purposes of training an inference model, calibration of the AR-based system, and/or training of the user in an AR context, data that pairs, e.g., EMG signals and joint angles may be used to train and/or correct a musculo-skeletal inference model in real time to create more accurate joint-angle predictions. However, for a gesture classifier, it may be desirable to determine specifically whether the user is performing a given gesture. In such a case, one or more camera(s) (e.g., the camera(s) 204) may be used to obtain information usable to provide training and/or classification data, such as gesture labels, by detecting matches or targeting joint angles against which to regress the model.

Figure 5:
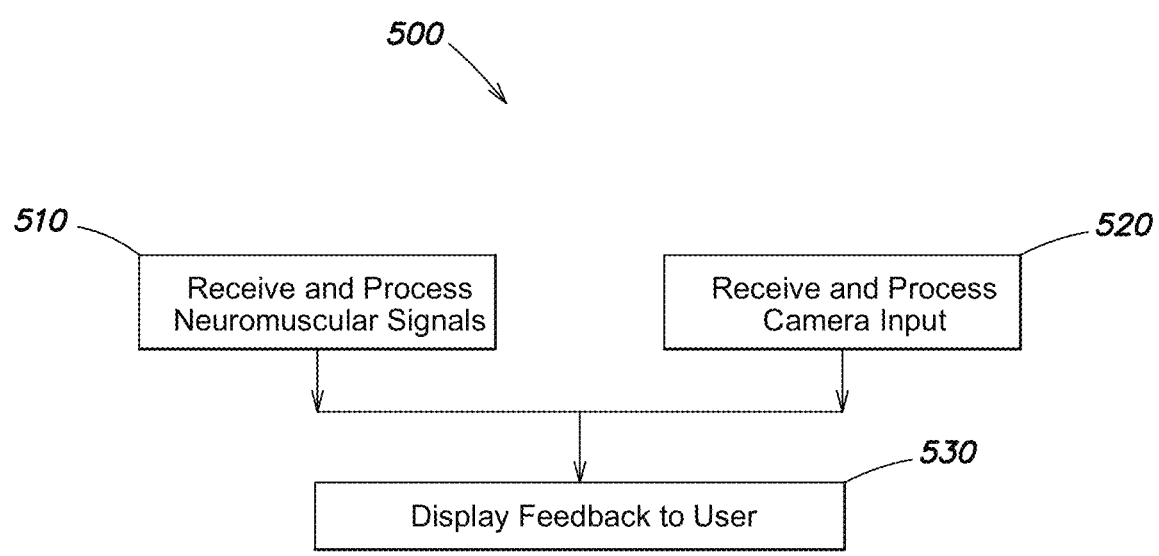
FIG. 5 is a flowchart of a process for integrating neuromuscular signals and camera data and providing feedback to a user in accordance with some embodiments of the technology described herein.

FIG. 5 is a flowchart of a process 500 for integrating neuromuscular signals and camera input signals, and providing feedback to a user, in accordance with some embodiments of the technology described herein. The process 500 may be performed by the AR-based system 200 of FIG. 2. At act 510, the neuromuscular activity system 202 receives and processes signals in a similar manner as discussed above with reference to FIG. 3. Further, at act 520, the system 200 receives and processes camera input in a manner similar to that discussed above with reference to FIG. 3 (e.g., at the act 320). At act 530, the system 200 displays feedback to the user (e.g., within one or more of the display(s) 208 of the AR-based system 200). Alternatively, the system 200 may provide feedback in any number of different ways, such as audio feedback, haptic feedback, or other output perceivable by the user. To this end, the neuromuscular activity system 202 may be capable of providing output to other parts of the AR-based system 200 for the purpose of displaying or generating feedback output. In some implementations, the AR-based system 200 may have one or more audio outputs, displays, indicators and/or other type of output device capable of providing or rendering feedback to the user. Alternatively, the system 200 may be configured to provide or render an output signal (e.g., a control signal) to one or more third-party systems (e.g., a manager system, monitor system, supervisor system, or other type of third-party system).

Figure 6:
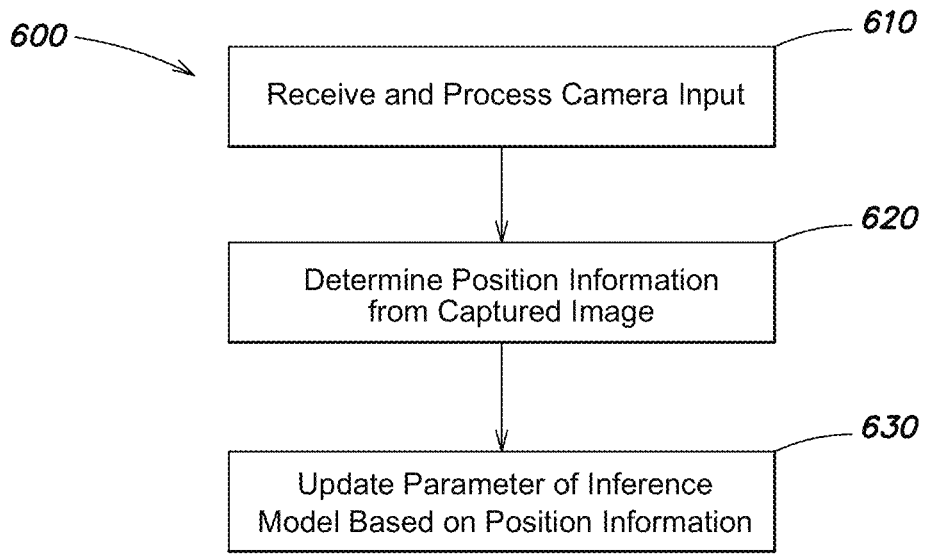
FIG. 6 is a flowchart of a process for updating an inference model based on camera data in accordance with some embodiments of the technology described herein.

FIG. 6 is a flowchart of a process 600 for updating an inference model based on camera data in accordance with some embodiments of the technology described herein. The process 600 may be performed by the AR-based system 200 of FIG. 2. At act 610, the system 200 receives and processes camera input (e.g., an input signal of a captured image). In one embodiment, at act 620, the system 200 determines position information from the captured image or from other input (e.g., neuromuscular data). At act 630, the system 200 may update a parameter of the inference model based on the determined position information. For example, in a situation where the neuromuscular activity system 202 determines a hand position and/or an arm position, camera input data (e.g., an image of the hand and/or the arm) may be used to correct position information for that particular inference model in a calibration action, i.e., to calibrate the inference model. In cases where there are two or more sources of data (e.g., camera data and EMG data), the inference model may require that the data from the sources be simultaneously acquired. For instance, there may be error or drift within a signal corresponding to EMG-based position information, and a ground truth position determined from a camera input signal may be used to adjust a parameter of an EMG-based inference model. In this way, accuracy of the EMG-based inference model may be improved by use of both the EMG and camera input signals to calibrate the EMG-based inference model. Such a process may be used as part of a calibration operation where a user performs discrete gestures and/or performs gestures in real time in a "normal" operation, and an inference model for the gestures needs to be adjusted based on ground truth data generated by a signal source other than the source providing the neuromuscular signals for the model; the other signal source may, for example be a camera. In some embodiments, camera data may be used to estimate continuous joint angles (e.g., for a regression model) or to identify discrete gestures (e.g., for a classifier).

Figure 7:
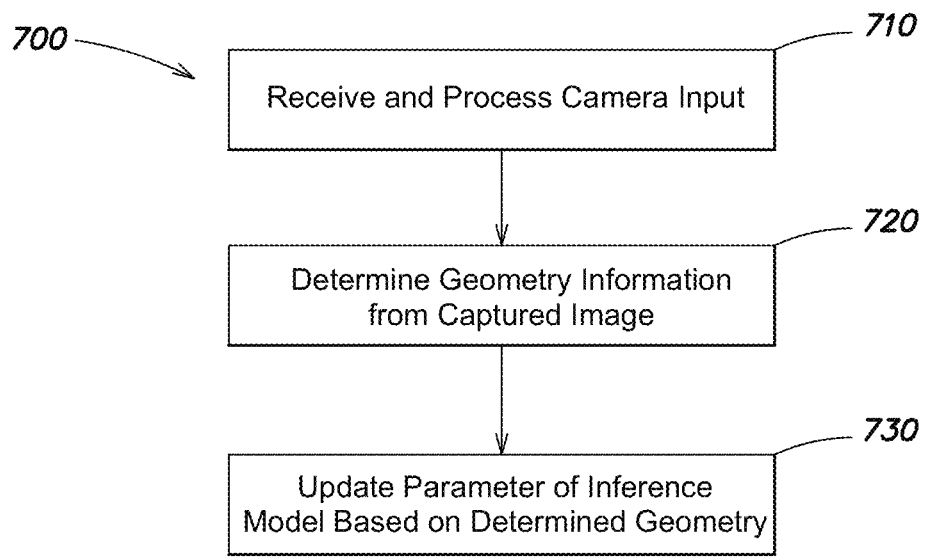
FIG. 7 is a flowchart of a process for updating an inference model based on camera data in accordance with some embodiments of the technology described herein.

FIG. 7 is a flowchart of a process 700 for updating an inference model based on camera data in accordance with some embodiments of the technology described herein. The process 700 may be performed by the AR-based system 200 of FIG. 2. Similar to the act 610 of FIG. 6, at act 710, the system 200 receives and processes camera input (e.g., an input signal of a captured image). At act 720, the system 200 determines geometry information from the captured image. For instance, when capturing an image of a hand, geometrical information such as segment lengths, joint positions, and other geometrical relations of a hand may be captured. At act 730, such geometrical information may be used to update one or more parameters of an inference model. In one example implementation, the system 200 may correct a geometry used by an EMG model of a hand. It is appreciated, for example, that an image captured by a camera may more accurately portray a geometry of a hand of the user than an image generated using EMG-based signals. For instance, an image of a segment length of a finger as captured by a camera may be used to update an EMG-based inference model of hand geometry. This may be especially pertinent when the EMG-based inference model is corrected or updated for use with that particular user.

Figure 8:
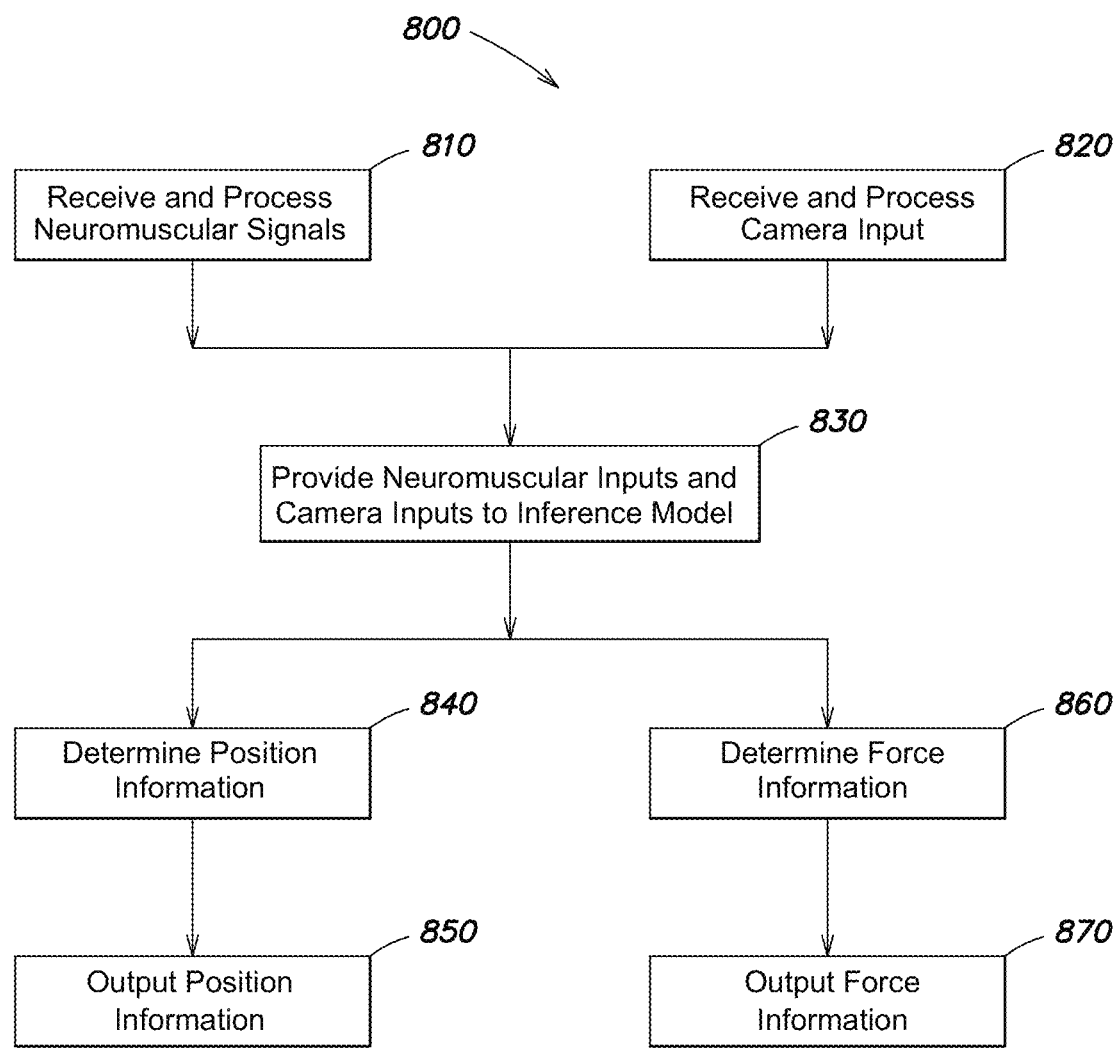
FIG. 8 is a flowchart of a process for determining position information and force information, in accordance with some embodiments of the technology described herein.

FIG. 8 is a flowchart 800 of a process for determining position information and force information in accordance with some embodiments of the technology described herein. In particular, as discussed above, it may be beneficial to use both neuromuscular signals and camera input signals to more accurately determine position and force information within an AR environment. The process 800 may be performed by the AR-based system 200 of FIG. 2. At act 810, the neuromuscular activity system 202 receives and processes neuromuscular input signals. Further, at act 820, the AR system 201 receives and processes at least one camera input signal. At act 830, the neuromuscular input signals and the camera input signal(s) are provided to an inference model. Based on both inputs, the system 200 may determine position information (e.g., at act 840), and may determine force information (e.g., at act 860). The position information and the force information may be used, for example, to render a representation of a user's hand within an AR display. For example, the representation may indicate a more accurate position of the user's hand and finger appendages as well as any forces that may be applied to any of the hand and/or the finger appendages. In one specific example, the system 200 may more accurately render the user's hand position where the user's thumb is pressing on the index finger of the same hand. The camera input may be particularly useful, as it may provide a visual indication that the index finger and the thumb are in contact, while the neuromuscular signals may indicate that forces are being applied by the index finger and the thumb at some relative level (e.g., the index finger and the thumb are being pressed together with a light amount of force). In this way, the system 200 may more accurately represent handstate information of the user's hand. Optionally, the system 200 may provide position information and force information as outputs, at acts 850 and 870, respectively. Such outputs may be used by one or more other systems to provide indications, render outputs or other representations, and/or control other systems.

In some implementations, the camera input signals may be processed to determine whether one or more fingers are in contact with the user's thumb and, if so, which fingers are in contact with the thumb. In one embodiment, if there is contact, a magnitude of the force between the thumb and the contacting fingers then may be estimated as an affine transformation as a function of the logarithm of a signal power recorded from the neuromuscular sensors that provided the neuromuscular input signals (e.g., EMG signal power) or with another signal processing technique for inferring a magnitude of force. Coefficients of the affine transformation function can be determined by a calibration stage in which the user first lightly touches the fingers and then later produces a maximum voluntary contraction corresponding to a pinch force between the fingers. In this implementation, the inference model may output a force in units of a fraction of the maximum voluntary contraction. In some implementations, the coefficients of the affine transformation function can be specific to the set of fingers contacting the thumb. Similarly, affine transformation functions of EMG signal power can be calibrated for cases where the user is applying forces against objects or surfaces.

Figure 9:
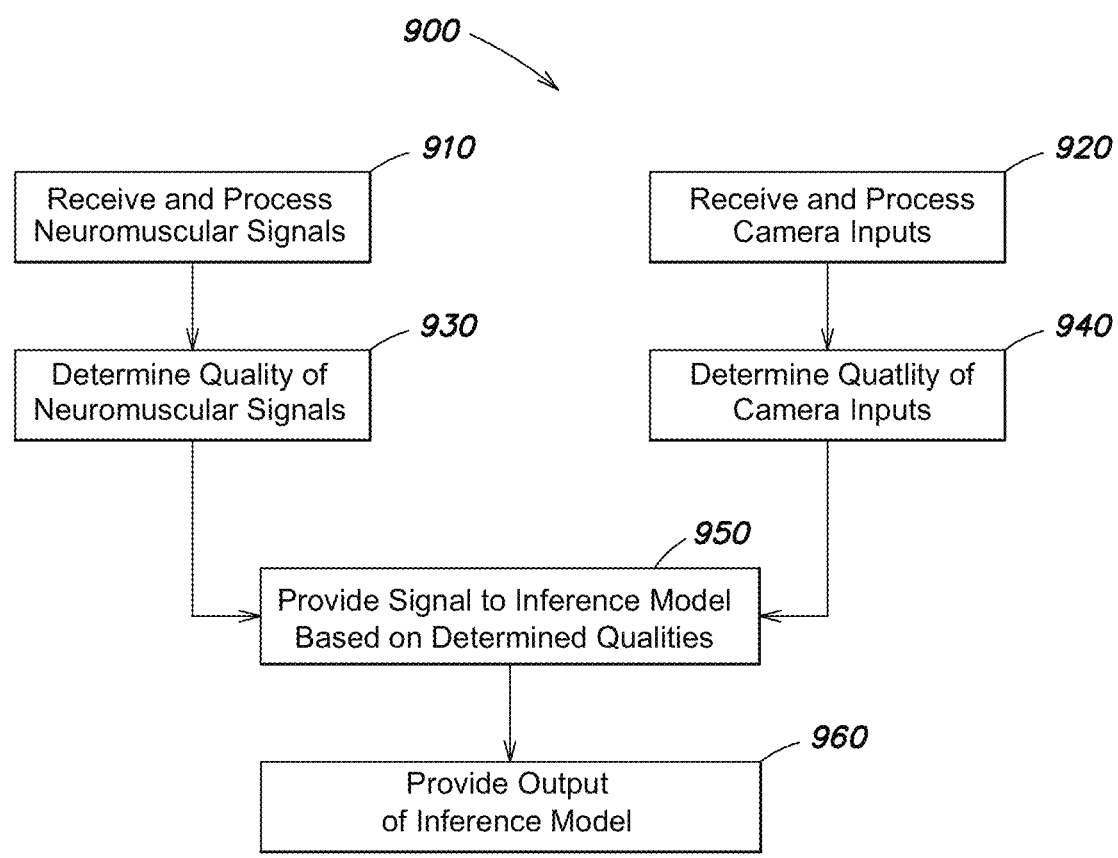
FIG. 9 is a flowchart of a process for determining qualities of input signals and performing model functions based on those qualities, in accordance with some embodiments of the technology described herein.

FIG. 9 is a flowchart of a process 900 for determining qualities of input signals and performing model functions based on those qualities, in accordance with some embodiments of the technology described herein. The process 900 may be performed by the AR-based system 200 of FIG. 2. For example, it is appreciated that certain input signals may be more reliable than others in certain situations. For example, a camera input signal may be less reliable for information when an object to be modeled is occluded from view or not within the camera's view at all. Similarly, neuromuscular signals may include errors generated by varying physical conditions, noise, or other interference. Therefore, it may be beneficial for a system to adaptively determine the qualities of particular input signals so that a model may be properly updated.

At act 910, the system 200 receives and processes neuromuscular signals (e.g. as received by the neuromuscular activity system 202). At act 920, the AR system 201 receives and processes one or more camera input signal(s). At act 930, the system 200 determines a quality of the neuromuscular signals. For instance, the neuromuscular activity system 202 or another suitable system may determine whether the neuromuscular signals should be used and, if so, to what level. For instance, certain portions of the neuromuscular signals may be accurate (e.g., a force measurement) but other portions of the neuromuscular signals may not (e.g., absolute forearm position). Certain portions of the neuromuscular signals may be reliable within certain time frames, and under varying conditions. For example, EMG signals having a substantial power (e.g., power above a predetermined threshold) at low (e.g., less than 20 Hz) or high (e.g., greater than 500 Hz) frequencies may indicate a low quality of the EMG signals.

At act 940, the system 200 may determine a quality of the camera input signals. As discussed above, a camera signal may be determined to be of a particular quality level when certain objects are within a field of view, and a camera signal may be determined to be at a lower quality level when objects are occluded or not within the field of view. At act 950, the system 200 may provide a signal to an inference model based on the determined qualities of the camera input signal(s) and the neuromuscular signals. For example, one or more camera input signal(s) or neuromuscular signals may be filtered or deprecated prior to being input into the inference model. In another implementation, the inference model may be trained under varying conditions and may be trained to be responsive to signals of different quality. In another implementation, separate Bayesian predictions and confidences may be determined from each of the two types of input, and Bayesian approaches may be used to combine the two predictions (e.g., by taking a weighted average). At act 960 the system 200 provides an output of the inference model.

Figure 10:
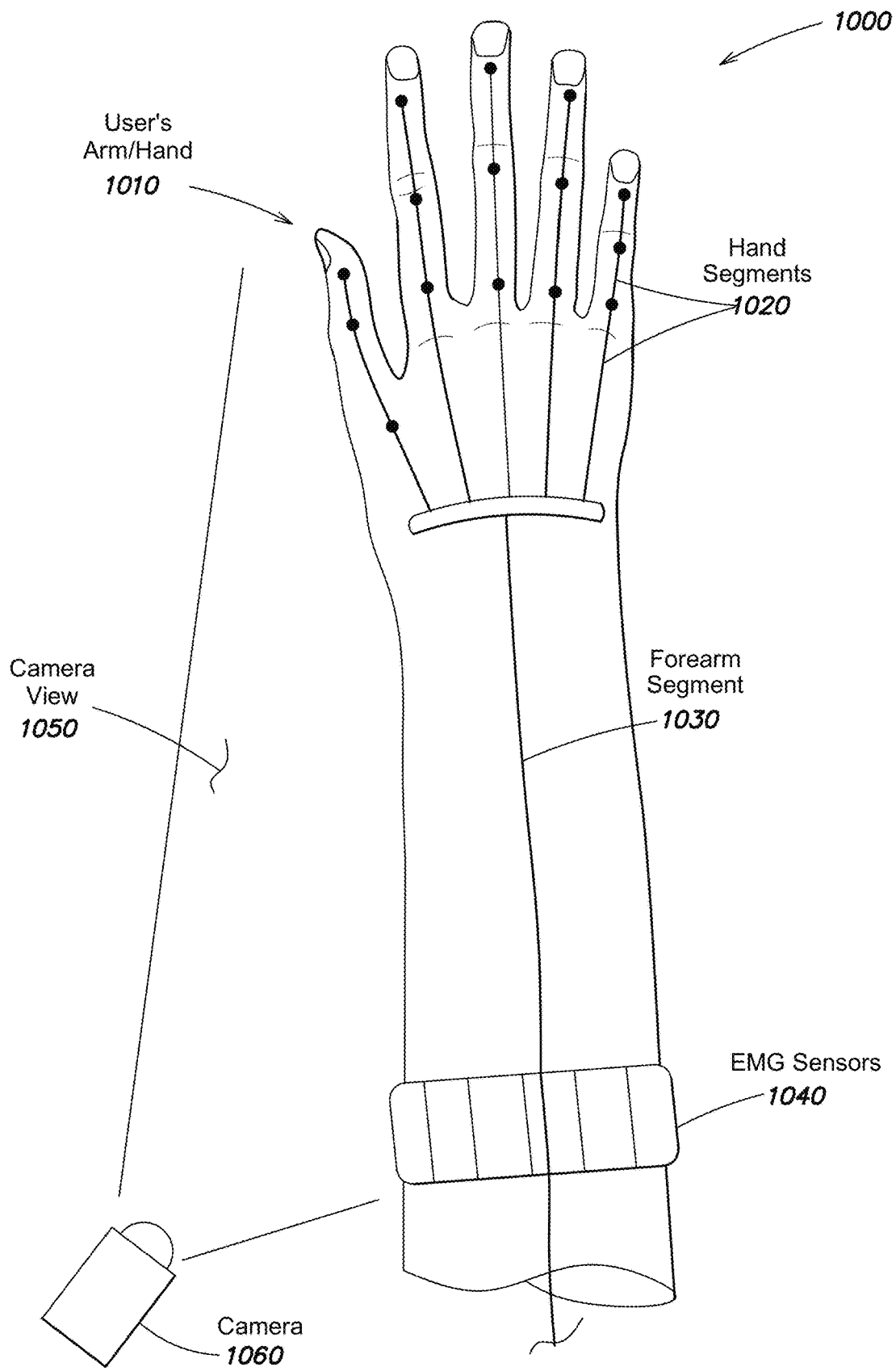
FIG. 10 is a diagram showing an example implementation using EMG sensors and a camera, in accordance with some embodiments of the technology described herein.

FIG. 10 is a diagram showing an example implementation of a system 1000 that utilizes one or more EMG sensor(s) 1040 and a camera 1060, in accordance with some embodiments of the technology described herein. For example, FIG. 10 shows a user's arm and an attached hand ("arm/hand") 1010, which is made up of one or more joints and segments, and which can be depicted as a musculoskeletal representation. More particularly, the user's hand segments 1020 are connected by joints. The arm and hand positions and segment lengths of the arm and the hand can be determined by the system 1000 and positioned within a three-dimensional space of a model musculoskeletal representation. Further, the user's hand may also include an interpolated forearm segment 1030. As discussed above, a neuromuscular activity system may be used to determine one or more representations of a user's hand/arm positions. To this end, the user may wear a band comprising the one or more EMG sensor(s) 1040, which sense and record neuromuscular signals that are used to determine a musculoskeletal skeletal representation. Concurrently with the EMG sensor(s) 1040 sensing and recording the neuromuscular signals, a camera 1060 may be used to capture objects within the camera's field of view 1050. For example, in FIG. 10, the camera's field of view 1050 include the user's arm/hand 1010. Camera data in addition to the neuromuscular activity signals determined by the EMG sensors 1040 may be used to reconstruct positions, geometries, and forces being applied by the user's arm/hand 1010. Further, outputs from the system 1000 can be provided that allow the system 1000 to render a representation of the user's arm/hand 1010, such as within an AR display or other type of system.

Figure 11:
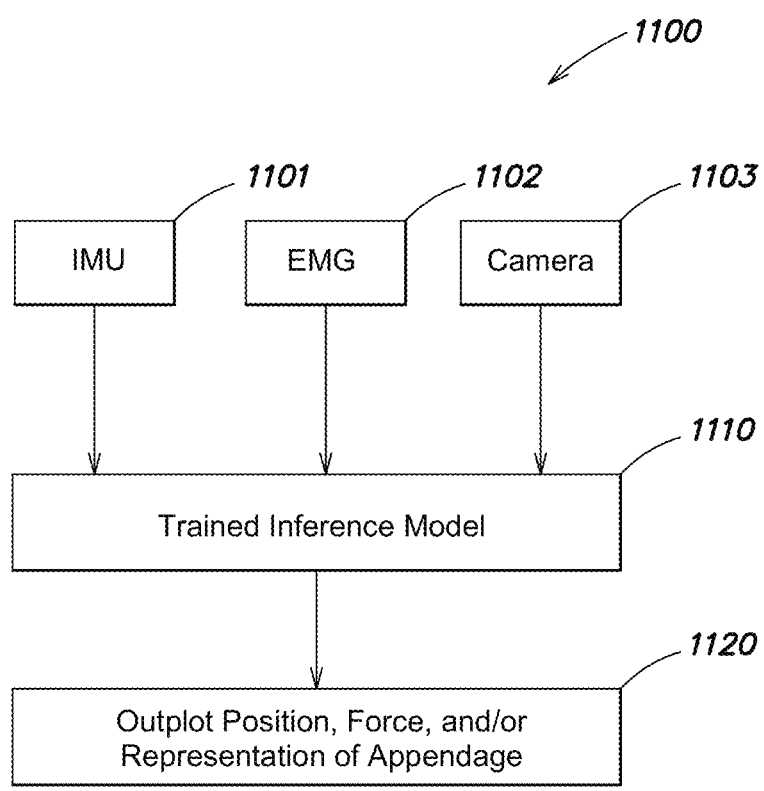
FIG. 11 is a diagram showing a trained inference model with representative inputs and outputs, in accordance with some embodiments of the technology described herein.

FIG. 11 is a diagram showing a process 1100 of processing inputs to a trained inference model in accordance with some embodiments of the technology described herein. For example, it is appreciated that a more accurate representation of a musculoskeletal representation may be obtained by using IMU inputs (1101), EMG inputs (1102), and camera inputs (1103). Each of these inputs 1101, 1102, 1103 may be provided to a trained inference model 1110. The inference model 1110 may be structured to provide one or more outputs, such as position, force, and/or a representation of a musculoskeletal state. Such outputs may be provided to one or more system(s), such as an AR system for indication or display, as discussed above, or for providing feedback to a user. It should be appreciated that any of the inputs 1101, 1102, 1103 may be used in any combination with any other input to derive an output from the trained inference model.

For instance, forearm positional information may be derived based on a combination of the IMU input 1101 and the camera input 1103. In one implementation, an estimate of forearm position may be generated based on the IMU input 1101 and adjusted based on ground truth data obtained from the camera input 1103. Also, forearm position and/or forearm orientation may be derived using the camera input 1103 alone without the IMU input 1101. In another scenario, the EMG input 1102 (e.g., EMG signals) may be used to derive force-only information to augment posture-only information provided by a camera-model system. Other combinations of inputs may be used to obtain a desired output and are within the scope of various embodiments descried herein.

It should also be appreciated that such outputs may be derived with or without generating any musculoskeletal representation. It should also be appreciated that one or more outputs may be used as control inputs to any other system, such as an output of an EMG-based control signal that is used as a control input signal provided to an AR system.

It is appreciated that any embodiment described herein may be use alone or in any combination with any other embodiment described herein. Further, portions of an embodiment described herein may be combined with portions of one or more other embodiments described herein. Additionally, embodiments described herein may be used in whole or in part with embodiments described in U.S. patent application Ser. No. 16/257,979, filed Jan. 25, 2019, entitled "CALIBRATION TECHNIQUES FOR HANDSTATE REPRESENTATION MODELING USING NEUROMUSCULAR SIGNALS," which is incorporated by reference herein, and U.S. patent application Ser. No. 15/659,504, filed Jul. 25, 2017, entitled "SYSTEM AND METHOD FOR MEASURING THE MOVEMENTS OF ARTICULATED RIGID BODIES," which is incorporated by reference herein.

The above-described embodiments can be implemented in any of numerous ways. For example, the embodiments may be implemented using hardware, software or a combination thereof. When implemented using software, code comprising the software can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the technologies described herein. The computer-readable storage medium can be transportable such that the program stored thereon can be loaded onto any computer resource to implement the aspects of the present invention discussed herein. In addition, it should be appreciated that reference to a computer program that, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

Various aspects of the technology presented herein may be used alone, in combination, or in a variety of arrangements not specifically discussed in the embodiments described above and therefore are not limited in their application to the details and arrangements of components set forth in the foregoing description and/or in the drawings.

Also, some of the embodiments described above may be implemented as one or more method(s), of which some examples have been provided. The acts performed as part of the method(s) may be ordered in any suitable way. Accordingly, embodiments may be constructed in which acts are performed in an order different than illustrated or described herein, which may include performing some acts simultaneously, even though shown as sequential acts in illustrative embodiments. The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

The foregoing features may be used, separately or together in any combination, in any of the embodiments discussed herein.

Further, although advantages of the present invention may be indicated, it should be appreciated that not every embodiment of the invention will include every described advantage. Some embodiments may not implement any features described as advantageous herein. Accordingly, the foregoing description and attached drawings are by way of example only.

Variations on the disclosed embodiment are possible. For example, various aspects of the present technology may be used alone, in combination, or in a variety of arrangements not specifically discussed in the embodiments described in the foregoing, and therefore they are not limited in application to the details and arrangements of components set forth in the foregoing description or illustrated in the drawings. Aspects described in one embodiment may be combined in any manner with aspects described in other embodiments.

Use of ordinal terms such as "first," "second," "third," etc., in the description and/or the claims to modify an element does not by itself connote any priority, precedence, or order of one element over another, or the temporal order in which acts of a method are performed, but are used merely as labels to distinguish one element or act having a certain name from another element or act having a same name (but for use of the ordinal term) to distinguish the elements or acts.

The indefinite articles "a" and "an," as used herein in the specification and in the claims, unless clearly indicated to the contrary, should be understood to mean "at least one."

Any use of the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Any use of the phrase "equal" or "the same" in reference to two values (e.g., distances, widths, etc.) means that two values are the same within manufacturing tolerances. Thus, two values being equal, or the same, may mean that the two values are different from one another by ±5%.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

Also, the phraseology and terminology used herein is for the purpose of description and should not be regarded as limiting. Use of terms such as "including," "comprising," "comprised of," "having," "containing," and "involving," and variations thereof herein, is meant to encompass the items listed thereafter and equivalents thereof as well as additional items.

The terms "approximately" and "about" if used herein may be construed to mean within ±20% of a target value in some embodiments, within ±10% of a target value in some embodiments, within ±5% of a target value in some embodiments, and within ±2% of a target value in some embodiments. The terms "approximately" and "about" may equal the target value.

The term "substantially" if used herein may be construed to mean within 95% of a target value in some embodiments, within 98% of a target value in some embodiments, within 99% of a target value in some embodiments, and within 99.5% of a target value in some embodiments. In some embodiments, the term "substantially" may equal 100% of the target value.

What is claimed is:

1. A computerized system for training one or more inference models used to generate a musculoskeletal representation, the system comprising:
   one or more neuromuscular sensors configured to obtain one or more neuromuscular signals from a user, wherein the one or more neuromuscular sensors are arranged on one or more wearable devices;
   at least one camera configured to capture one or more images while the one or more neuromuscular signals are obtained; and
   at least one computer processor programmed to:
      determine image-based position information describing a spatial relationship between two or more connected musculoskeletal segments of the user based on the one or more images;
      determine neuromuscular-based position and/or force information for the two or more connected musculoskeletal segments of the user based on the neuromuscular signals;
      associate the image-based position information with the neuromuscular-based position and/or force information for the two or more connected musculoskeletal segments of the user; and
      train the one or more inference models to output the musculoskeletal representation based on the image-based position information and the neuromuscular-based position and/or force information when one or more additional neuromuscular signals obtained from the user have at least one predetermined characteristic.

2. The computerized system of claim 1, wherein the at least one computer processor provides as an output the musculoskeletal representation based on the image-based position information and the neuromuscular-based position and/or force information.

3. The computerized system of claim 1, wherein the one or more images comprise a series of time-sequenced images forming a video.

4. The computerized system of claim 1, wherein the musculoskeletal representation corresponds to any one or any combination of:
   a muscular activation state;
   a forearm or hand motion;
   a posture;
   a static gesture;
   a handstate;
   a pose; and
   a dynamic gesture.

5. The computerized system of claim 1, wherein the one or more images includes any one or any combination of:
   an image produced by visible light;
   an image produced by infrared light;
   an image produced by light of a predetermined range of wavelengths; and
   an image produced by light of two or more different predetermined ranges of wavelengths.

6. The computerized system of claim 1, wherein the at least one computer processor is programmed to:
   determine a first quality of the one or more neuromuscular signals and/or a second quality of the one or more images; and
   weight the one or more neuromuscular signals and/or the one or more images based on the first quality and/or the second quality, respectively.

7. The computerized system of claim 6, wherein the first quality of the one or more neuromuscular signals is determined by determining whether at least one of the one or more neuromuscular signals includes at least one signal artifact.

8. The computerized system of claim 6, wherein the second quality of the one or more images is determined by determining whether a hand of the user is fully included in a field of view of the at least one camera or whether the hand is fully occluded from the field of view of the at least one camera, or whether at least a portion of the hand of the user is occluded from the field of view of the at least one camera.

9. The computerized system of claim 6, wherein the at least one computer processor is further programmed to determine the first quality in response to a determination that the second quality is greater than a threshold value.

10. The computerized system of claim 1, wherein the at least one predetermined characteristic comprises any one or any combination of:
  a presence of an artifact of the one or more additional neuromuscular signals;
  a presence of a plurality of artifacts of the one or more additional neuromuscular signals;
  a relative position of a plurality of artifacts of the one or more additional neuromuscular signals;
  a range of amplitudes of the one or more additional neuromuscular signals; and
  a periodic frequency of artifacts of the one or more additional neuromuscular signals.

11. The computerized system of claim 1, further comprising at least one inertial measurement unit (IMU) sensor, wherein the at least one computer processor is further programmed to determine IMU-based position information based, at least in part, on IMU signals output from the at least one IMU sensor, and the least at least one computer processor is programmed to associate the IMU-based position information with the image-based position information and the neuromuscular-based position and/or force information for the two or more connected musculoskeletal segments of the user.

12. The computerized system of claim 1, wherein:
  the one or more wearable devices includes at least one positional marker included thereon; and
  the image-based position information is determined based, at least in part, on the at least one positional marker captured in the one or more images.

13. A method of a computerized system for training one or more inference models used to generate a musculoskeletal representation, the method comprising:
  receiving, by at least one processor, one or more neuromuscular signals of a user, the one or more neuromuscular signals being obtained by one or more neuromuscular sensors arranged on one or more wearable devices worn by the user;
  receiving, by the at least one processor, one or more images captured by at least one camera while the one or more neuromuscular signals are obtained;
  determining, by the at least one processor based on information obtained from the one or more images, image-based position information describing a spatial relationship between two or more connected musculoskeletal segments of the user;
  determining, by the at least one processor based on the one or more neuromuscular signals, neuromuscular-based position and/or force information for the two or more connected musculoskeletal segments;
  associating, by the at least one processor, the image-based position information with the neuromuscular-based position and/or force information;

training, by the at least one processor, the one or more inference models to output the musculoskeletal representation based on the image-based position information and neuromuscular-based position and/or force information when one or more additional neuromuscular signals have at least one predetermined characteristic.

14. The method of claim 13, further comprising providing as output the musculoskeletal representation based on the image-based position information and the neuromuscular-based position and/or force information.

15. The method of claim 13, wherein the one or more images comprise a series of time-sequenced images forming a video.

16. The method of claim 13, wherein the musculoskeletal representation corresponds to any one or any combination of:
  a muscular activation state;
  a forearm or hand motion;
  a posture;
  a static gesture;
  a handstate;
  a still pose; and
  a dynamic gesture.

17. The method of claim 13, wherein the one or more images includes any one or any combination of:
  an image produced by visible light;
  an image produced by infrared light;
  an image produced by light of a predetermined range of wavelengths; and
  an image produced by light of two or more different predetermined ranges of wavelengths.

18. The method of claim 13, further comprising:
  determining, by the at least one processor, a first quality of the one or more neuromuscular signals and/or a second quality of the one or more images; and
  weighting, by the at least one processor, the one or more neuromuscular signals based on the first quality and/or weighting the one or more images based on the second quality, respectively.

19. The method of claim 18, wherein the first quality of the one or more neuromuscular signals is determined by determining whether at least one of the one or more neuromuscular signals includes at least one signal artifact.

20. The method of claim 18, wherein the second quality of the one or more images is determined by determining whether a hand of the user is fully included in a field of view of the at least one camera or whether the hand is fully occluded from the field of view of the at least one camera, or whether at least a portion of the hand of the user is occluded from the field of view of the at least one camera.

21. The method of claim 18, further comprising determining, by the at least one processor, the first quality in response to a determination that the second quality is greater than a threshold value.

22. The method of claim 13, wherein the at least one predetermined characteristic comprises any one or any combination of:
  a presence of an artifact of the one or more additional neuromuscular signals;
  a presence of a plurality of artifacts of the one or more additional neuromuscular signals;
  a relative position of a plurality of artifacts of the one or more additional neuromuscular signals;
  a range of amplitudes of the one or more additional neuromuscular signals; and a periodic frequency of artifacts of the one or more additional neuromuscular signals.

23. The method of claim 13, further comprising:
receiving, by the at least one processor, inertial measurement unit (IMU) signals output from at least one IMU sensor;
determining, by the at least one processor, IMU-based position information based, at least in part, on the IMU signals output from the at least one IMU sensor; and
associating the IMU-based position information with the image-based position information and the neuromuscular-based position and/or force information for the two or more connected musculoskeletal segments of the user.

24. The method of claim 13, wherein:
the one or more wearable devices includes at least one positional marker included thereon; and
the image-based position information is determined based, at least in part, on the at least one positional marker captured in the one or more images.

25. A non-transitory computer-readable storage medium storing code that, when executed by at least one computer, causes the at least one computer to perform a method for training one or more inference models used to generate a musculoskeletal representation, wherein the method comprises:
receiving one or more neuromuscular signals of a user, the one or more neuromuscular signals being obtained by one or more neuromuscular sensors arranged on one or more wearable devices worn by the user;
receiving one or more images captured by at least one camera while the one or more neuromuscular signals are obtained;
determining, based on information obtained from the one or more images, image-based position information describing a spatial relationship between two or more connected musculoskeletal segments of the user;
determining, based on the neuromuscular signals, neuromuscular-based position and/or force information for the two or more connected musculoskeletal segments;
associating the image-based position information with the neuromuscular-based position and/or force information; and
training the one or more inference models to provide as output the musculoskeletal representation based on the image-based position information and the neuromuscular-based position information and/or force information when one or more additional neuromuscular signals have at least one predetermined characteristic.

26. The storage medium of claim 25, wherein the method further comprises providing the musculoskeletal representation as an output based on the image-based position information and the neuromuscular-based position information and/or force information.

27. The storage medium of claim 25, wherein the method further comprises:
determining a first quality of the one or more neuromuscular signals and/or a second quality of the one or more images; and
weighting the one or more neuromuscular signals based on the first quality and/or weighting the one or more images based on the second quality, respectively.

28. The storage medium of claim 27, wherein the method further comprises determining the first quality in response to a determination that the second quality is greater than a threshold value.

29. The storage medium of claim 25, wherein the at least one predetermined characteristic comprises any one or any combination of:
a presence of an artifact of the one or more additional neuromuscular signals;
a presence of a plurality of artifacts of the one or more additional neuromuscular signals;
a relative position of a plurality of artifacts of the one or more additional neuromuscular signals;
a range of amplitudes of the one or more additional neuromuscular signals; and
a periodic frequency of artifacts of the one or more additional neuromuscular signals.

30. The storage medium of claim 25, wherein the method further comprises:
receiving inertial measurement unit (IMU) signals output from at least one IMU sensor;
determining IMU-based position information based, at least in part, on the IMU signals output from the at least one IMU sensor; and
associating the IMU-based position information with the image-based position information and the neuromuscular-based position and/or force information for the two or more connected musculoskeletal segments of the user.

* * * * *